US008343739B2

(12) United States Patent
Katz et al.

(10) Patent No.: US 8,343,739 B2
(45) Date of Patent: Jan. 1, 2013

(54) METABOLICALLY ENGINEERED CELLS FOR THE PRODUCTION OF PINOSYLVIN

(75) Inventors: Michael Katz, Malmö (SE); Jochen Förster, København (DK); Helga David, København (DK); Hans Peter Schmidt, Holte (DK); Malin Sendelius, Lund (SE); Sara Peterson Bjørn, Lyngby (DK); Thomas Thomasen Durhuus, København (DK)

(73) Assignee: Fluxome Sciences A/S, Lyngby (DK)

( * ) Notice: Subject to any disclaimer, the term of this patent is extended or adjusted under 35 U.S.C. 154(b) by 519 days.

(21) Appl. No.: 12/374,659

(22) PCT Filed: Jul. 19, 2007

(86) PCT No.: PCT/EP2007/057484
§ 371 (c)(1),
(2), (4) Date: Jun. 1, 2009

(87) PCT Pub. No.: WO2008/009728
PCT Pub. Date: Jan. 24, 2008

(65) Prior Publication Data
US 2009/0317881 A1    Dec. 24, 2009

(30) Foreign Application Priority Data
Jul. 20, 2006 (GB) .................................. 0614442.2

(51) Int. Cl.
*C12P 7/22* (2006.01)
(52) U.S. Cl. ...................................................... 435/156
(58) Field of Classification Search .................. None
See application file for complete search history.

(56) References Cited

U.S. PATENT DOCUMENTS

| | | | |
|---|---|---|---|
| 5,391,724 | A | 2/1995 | Kindl et al. |
| 5,500,367 | A | 3/1996 | Hain et al. |
| 5,973,230 | A | 10/1999 | Kindl et al. |
| 6,020,129 | A | 2/2000 | Schroder et al. |
| 7,604,968 | B2 | 10/2009 | Schmidt-Dannert et al. |

FOREIGN PATENT DOCUMENTS

| | | |
|---|---|---|
| JP | 2005-53862 | 3/2005 |
| KR | 2004-0105110 | 12/2004 |
| WO | WO 2006055322 | 8/2006 |
| WO | WO 2006089898 | 8/2006 |
| WO | WO 2006124999 | 11/2006 |
| WO | WO 2006125000 | 11/2006 |
| ZA | 20048194 | 10/2004 |

OTHER PUBLICATIONS

Serazetdinova et al., Journal of Plant Physiology, 162 (2005), pp. 985-1002.*
Sengottuvelan et al., British Journal of Nutrition, 2006, 96, 145-153.*
Roupe et al., Current Clinical Pharmacology, 2006, 1, 81-101.*
Sengottuvelan et al., British Journal of Nutrition (2006), 96, pp. 145-153.*
Roupe et al., Current Clinical Pharmacology, 2006, 1, pp. 81-101.*
Abe, I., Watanabe, T. and Noguchi, H. (2004). "Enzymatic formation of long-chain polyketide pyrones by plant type III polyketide synthases". *Phytochemistry.* 6, 2447-2453.
Aggarwal BB, Bhardwaj A, Aggarwal RS, Seeram NP, Shishodia S, Takada Y. (2004). "Role of resveratrol in prevention and therapy of cancer: preclinical and clinical studies". *Anticancer Res.* 24, 1-60 Review.
Allina, S.M., Pri-Hadash, A., Theilmann, D.A., Ellis, B.E. and Douglas, C.J. (1998) "4-coumarate: Coenzyme A ligase in hybrid poplar. Properties of enzymes, cDNA cloning, and analysis of recombinant clones". *Plant Physiol.* 116, 743-754.
Becker JV, Armstrong GO, van der Merwe MJ, Lambrechts MG, Vivier MA, Pretorius IS. (2003). "Metabolic engineering of *Saccharomyces cerevisiae* for the synthesis of the wine-related antioxidant resveratrol". *FEMS Yeast Res.* 4, 79-85.
Chen DC, Beckerich JM, Gaillardin C., "One-step transformation of the dimorphic yeast *Yarrowia lipolytica.*" *Appl Microbiol Biotechnol.* 1997:48:232-5.
Cochrane, F.C., Davin, L.B. and Lewis N.G. (2004). "The *Arabidopsis* phenylalanine ammonia lyase gene family: kinetic characterization of the four PAL isoforms". *Phytochemistry* 65, 1557-1564.
Cordero Otero R, Gaillardin C., "Efficient selection of hygromycin-B-resistant *Yarrowia lipolytica* transformants". *Appl Microbiol Biotechnol.* 1996:46:143-8.
Costa ML, Bedgar DL, Moinuddin SGA, Kim K, Cardenas CL, Cochrane FC, Shockey JM, Helms GL, Amakura Y, Takahashi H et al., "Characterization in vitro and in vivo of the putative multigene 4-coumarate:CoA ligase network in *Arabidopsis*: syringyl lignin and sinapate/sinapyl alcohol derivative formation", *Phytochemistry*, 2005:66:2072-2091.
Ehlting, J., Büttner, D., Wang, Q., Douglas, C.J., Somssich, I.E. and Kombrink, E. (1999). "Three 4-coumarate:coenzyme A ligases in *Arabidopsis thaliana* represents two evolutionary divergent classes in angiosperms". *The plant journal.* 19, 9-20.
Fickers P, Le Dall MT, Gaillardin C, Thonart P, Nicaud JM., "New disruption cassettes for rapid gene disruption and marker rescue in the yeast *Yarrowia lipolytica.*" *J Microbiol Methods.* 2003:55:727-37.
Gehlert, R., Schoppner, A. and Kindl, H. "Stilbene synthase from seedlings of *Pinus sylvestris*—purification and induction in response to fungal infection". *Mol. Plant-Microbe Interaction 3* (1990) 444-449.

(Continued)

*Primary Examiner* — Allison Ford
*Assistant Examiner* — Yvonne Pyla
(74) *Attorney, Agent, or Firm* — Iver P. Cooper

(57) ABSTRACT

A genetically engineered micro-organism having an operative metabolic pathway producing cinnamoyl-CoA and producing pinosylvin therefrom by the action of a stilbene synthase is used for pinosylvin production. Said cinnamic acid may be formed from L-phenylalanine by a L-phenylalanine ammonia lyase (PAL) which is one accepting phenylalanine as a substrate and producing cinammic acid therefrom, preferably such that if the PAL also accepts tyrosine as a substrate and forms coumaric acid therefrom, the ratio Km(phenylalanine)/Km(tyrosine) for said PAL is less than 1:1 and if said micro-organism produces a cinammate-4-hydroxylase enzyme (C4H), the ratio $K_{cat}(PAL)/K_{cat}(C4H)$ is at least 2:1.

27 Claims, 9 Drawing Sheets

OTHER PUBLICATIONS

Gems, D., Johnstone, I.L. and Clutterbuck, A.J. (1991). "An autonomously replicating plasmid transforms *Aspergillus nidulans* at high frequency". *Gene* 98, 61-67.

Hain, R., Reif, H.J., Krause, E., Langebartels, R., Kindl, H., Vornam, B., Wiese, W., Schmelzer, E., Schreier, P.H., Stocker, R.H. and Stenzel, K. (1993). „Disease resistance results from foreign phytoalexin expression in a novel plant. *Nature* 361, 153-156.

Hwang EL Kaneko M, Ohnishi Y, Horinouchi S. (2003). "Production of plant-specific flavanones by *Escherichia coli* containing an artificial gene cluster". *Appl. Environ. Microbiol.* 69, 2699-706.

Hamberger, B. and Hahlbrock, K. (2004). "The 4-coumarate:CoA ligase gene family in *Arabidopsis thaliana* comprises one rare, sinapate-activating and three commonly occurring isoenzymes". *Proc. Natl. Acad. Sci. USA*. 101, 2209-2214.

Hart, J. H. (1981), "Role of phytostilbenes in decay and disease resistance". *Annu. Rev. Phytopathology* 19, 437-458.

Hart, J. H., Shrimpton, D. M. (1979). "Role of stilbenes in resistance of wood to decay". *Phytopathology* 69, 1138-1143.

Hemingway R.W., McGraw, G.W. and Barras, S. J. (1977). "Polyphenols in *Ceratocystis minor* infected *Pinus taeda*: Fungal Metabolites, phloem and xylem phenols". *J. Agric. Food Chem.*, 25, 717-722.

Jeandet P et al, "Phyto alexins from the Vitaceae: biosynthesis . . . and metabolism", *Journal of Agricultural and food Chemistry*, 50, No. 10, 2731-2741.

Jiang H et al, "Metabolic engineering of the Phenylpropanoid pathway in *Saccharomyces cerevisiae*", *Applied and environmental Microbiology*, Jun. 2005, 2962-2969.

Juvvadi, P.R., Seshime, Y., Kitamoto, K. (2005). "Genomics reveals traces of fungal phenylpropanoid-flavonoid metabolic pathway in the filamentous fungus *Aspergillus oryzae*." *J Microbiol*. 43, 475-486.

Juretzek T, Le Dall M, Mauersberger S, Gaillardin C, Barth G, Nicaud J., "Vectors for gene expression and amplification in the yeast *Yarrowia lipolytica*", *Yeast*. 2001:18:97-113.

Kaneko, M., Ohnishi, Y. and Horinouchi, S., "Cinnamate:Coenzyine. A ligase from the Filamentous Bacteria *Streptomyces coelicolor* A3(2)", *J. Bact*. 185, 20-27. (2003).

Kindl, H. (1985) Biosynthesis of stilbenes. In Higuchi T, ed, Biosynthesis and Biodegradation of Wood Components. Academic Press, London, pp. 349-377.

Kodan, A., Kuroda, H. and Sakai, F. (2002). "A stilbene synthase from Japanese red pine (*Pinus densiflora*): Implications for phytoalexin accumulationand down-regulation of flavonoid biosynthesis". *Proc. Natl. Acad. Sci.* 99, 3335-3339.

Le Dall MT, Nicaud JM, Gaillardin C., "Multiple-copy integration in the yeast *Yarrowia lipolytica*". *Curr Genet*. 1994:26:38-44.

Lee S.K. et al., "Antibacterial and antifungal activity of pinosylvin, a constituent of pine", *Fitoterapia* 76 (2005) 258-260.

Lieutier, F., Sauvard, D., Brignolas, F., Picron, V., Yart, A., Bastien, C. and Jay-Allemand, C. (1996) "Changes in phenolic metabolites of Scots pine phloem induced by *Ophiostoma brunneo-ciliatum*, a bark beetle-associated fungus". *Eur. J.For Pathol*. 26, 145-158.

Lindberg LE, Willfor SM, Holmbom BR. (2004) "Antibacterial effects of knotwood extractives on paper mill bacteria". *J Ind Microbiol Biotechnol*. 31, 137-147.

Madzak C, Gaillardin C, Beckerich JM., "Heterologous protein expression and secretion in the non-conventional yeast *Yarrowia lipolytica*: a review". *J Biotechnol*. 2004:109:63-81.

Martin, V.J.J., Pitera, D.J., Withers, S.T., Newman, J.D. and Keasling, J.D. (2003). "Engineering a mevalonate pathway in *Escherichia coli* for production of terpenoids". *Nature biotechnology* 21, 796-802.

Melchior F, Kindl H (1991), "Coordinate and elicitor dependent expression of stilbene synthase and phenylalanine ammonialyase genes in *Vitis cv. Optima*." *Arch. Biochem. Biophys* 288, 552-557.

Mellanen, P., Petanen, T., Lehtimaki, J., Makela, S., Bylund, G., Holmbom, B., Mannila, E., Oikari, A. and Santti, R. (1996). "Wood-derived estrogens: studies in vitro with breast cancer cell lines and in vivo in trout". *Toxicol. App. Pharm*. 136, 381-388.

Merkulov S, van Assema F, Springer J, Fernandez Del Carmen A, Mooibroek H., Cloning and characterization of the *Yarrowia lipolytica* squalene synthase (SQS1) gene and functional complementation of the *Saccharomyces cerevisiae* erg9 mutation, *Yeast*. 2000:16:197-206.

Mizutani M and Ohta .D et al, 1998, "Two Isoforms of NADPH:Cytochrome P450 Reductase in *Arabidopsis thaliana*. Gene Structure, Heterologous Expression in Insect Cells, and Differential Regulation", *Plant Physiol*. 116, 357-367.

Morita, H., Noguchi, H., Schröder, J. and Abe, I. (2001). "Novel polyketides synthesized with a higher plant stilbene synthase". *Eur. J. Biochem*. 268, 3759-3766.

Müller S, Sandal T, Kamp-Hansen P, Dalbøge H., "Comparison of expression systems in the yeasts *Saccharomyces cerevisiae, Hansenula polymorpha, Klyveromyces lactis, Schizosaccharomyces pombe* and *Yarrowia lipolytica*. Cloning of two novel promoters from *Yarrowia lipolytica*". *Yeast*. 1998:14:1267-83.

Nicaud JM, Madzak C, van den Broek P, Gysler C, Duboc P, Niederberger P, Gaillardin C. "Protein expression and secretion in the yeast *Yarrowia lipolytica*". *FEMS Yeast Res*. 2002:2:371-9.

Pignède G, Wang HJ, Fudalej F, Seman M, Gaillardin C, Nicaud JM. "Autocloning and amplification of LIP2 in *Yarrowia lipolytica*." *Appl. Environ Microbiol*. 2000:66:3283-9.

Preisig-Muller, R., Sehwekendiek, A., Brehrn, I., Reif, H.J. and Kindl, H. (1999). "Characterization of a pine multigene family containing elicitor-responsive stilbene synthase genes". *Plant Mol. Biol*. 1999 39, 221-229.

Pacher T, Seger C, Engelmeier D, Vajrodaya S, Hofer O, Greger H. (2002). "Antifungal stilbenoids from *Stemona collinsae*." *J Nat Prod*. 65, 820-827.

Raiber S, Schröder G, Schröder J. (1995). "Molecular and enzymatic characterization of two stilbene synthases from Eastern white pine (*Pinus strobus*). A single Arg/His difference determines the activity and the pH dependence of the enzymes". *FEBS Lett*. 361, 299-302.

Richter, C., Wild, A. (1992). "Phenolic compounds in needles of Norway spruce trees in relation to novel forest decline: I. Studies on trees from site of the Northern Black Forest.", *Biochem. Biophys. Pflanz* 188, 305-320.

Ro D.K., Douglas C.J. (2004). "Reconstitution of the entry point of plant phenylpropanoid metabolism in yeast (*Saccharomyces cerevisiae*): implications for control of metabolic flux into the phenylpropanoid pathway". *J. Biol. Chem*. 279, 2600-2607.

Rosemann, D., Helier, W. and Sandermann, H.(1991). "Biochemical Plant Responses to Ozone. II. Induction of Stilbene Biosynthesis in Scots Pine (*Pinus sylvestris L.*) Seedlings. Jr." *Plant Physiol*. 97, 1280-1286.

Roupe, K.A., Remsberg, C.M., Yáñez. J.A. and Davies, N.M. (2006). "Pharmacometrics of Stilbenes: Seguing Towards the Clinic". *Curr. Clin. Pharmac*. 1, 81-101.

Samappito, S., Page, J.E., Schmidt, J., De-Eknamkul, W. and Kutchan, T.M. (2003). "Aromatic and pyrone polyketides synthesized by a stilbene synthase from *Rheum tataricum*". *Phytochemistry* 62, 313-323.

Schanz, S., Schröder, G. and Schröder, J. (1992). „Stilbene synthase from Scot's pine (*Pinus sylvestris*) *FEBS Lett*. 313, 71-74.

Schöppner, A. and Kindl, H. (1984) "Purification and properties of a stilbene synthase from induced cell suspension cultures of peanut". *J. Biol. Chem*. 259, 6806-6811.

Schröder G, Brown JWS, Schröder J. (1988). "Molecular analysis of resveratrol synthase. cDNA clones and relationship with chalcone synthase". *Eur J Biochem* 172, 161-169.

Seshime, Y., Juvvadi, P.R., Fujii, I. and Kitamoto, K. (2005). "Genomic evidences for the existence of a phenylpropanoid metabolic pathway in *Aspergillus oryzue*." *Biochem. Biophys. Res Commun*. 337, 747-51.

Skinnider, L. and Stoessl A. (1986). "The effect of the phytoalexins, lubimin, (-)-maackiain, pinosylvin, and the related compounds dehydroloroglossol and hordatine M on human lymphoblastoid cell lines". *Experientia* 42, 568-570.

Stojanovic, S., Sprinz, H. and Brede, O. (2001). "Efficiency and mechanism of the anti-oxidant action of trans-resveratrol and its analogues in the radical liposome oxidation". *Arch. Biochem. Biophys*. 391, 79-89.

Suga T., Ohta. S., Munesada K., Ide N., Kurokawa M., Shimizu M., Ohta E. (1993). "Endogenous pine wood nematicidal substances in pines, *Pinus massoniana, P. strobus and P. palustris.*" *Phytochemistry* 33, 1395-1401.

Tropf, S., Karcher, B., Schröder, G. and Schröder, J. (1995). "Reaction mechanisms of homodimeric plant polyketide synthase (stilbenes and chalcone synthase). A single active site for the condensing reaction is sufficient for synthesis of stilbenes, chalcones, and 6'-deoxychalcones". *J. Biol. Chem.* 270, 7922-7928.

Urban P, Wercek-Reichhart D, Teutsch HG, Durst F, Regnier S, Kazmaier M, Pompon D (1994). "Characterization of recombinant plant cinnarnate 4-hydroxylase produced in yeast. Kinetic and spectral properties of the major plant P450 of the phenylpropanoid pathway". *Eur J Biochem.* 222:843-50.

Verduyn C, Postma E, Scheffers WA, Van Dijken JP. (1992). "Effect of benzoic acid on metabolic fluxes in yeasts: a continuous-culture study on the regulation of respiration and alcoholic fermentation". *Yeast.* 8, 501-517.

Watts et al; Watts KT, Mijts BN, Lee PC, Manning AJ, Schmidt-Dannert C.(2006). "Discovery of a substrate selectivity switch in tyrosine ammonia-lyase, a member of the aromatic amino acid lyase family". *Chem Biol.* 13:1317-26.

Wiese W, Vornam B, Krause E, Kindl H (1994). „Structural organization and differential expression of three stilbene synthase genes located on a 13 kb grapevine DNA fragment. *Plant Mol Biol* 26, 667-677.

* cited by examiner

SEQUENCE LISTING

```
<160> NUMBER OF SEQ ID NOS: 30

<210> SEQ ID NO 1
<211> LENGTH: 2154
<212> TYPE: DNA
<213> ORGANISM: Arabidopsis thaliana

<400> SEQUENCE: 1
atggatcaaa tcgaagcaat gttgtgcggc ggaggagaga agacaaaagt ggcggttact      60
acgaagactt tggcagatcc attgaattgg ggtttagcag cggatcaaat gaaaggaagt     120
catttagatg aagtgaagaa gatggtcgaa gagtatcgta gaccagtcgt gaatcttggc     180
ggagaaacac tgacgatcgg acaagttgct gccatctcca ccgtaggagg cagcgttaag     240
```

```
gttgagttag cggagacttc aagagccggt gtgaaagcta gcagtgattg ggttatggag    300
agcatgaaca aggtactga cagttacgga gtcaccaccg ctttggtgc tacttctcac    360
cggagaacca aaacggcac cgcattacaa acagaactca ttagatttt gaacgccgga    420
atattcggaa acacgaagga gacatgtcac acactgccgc aatccgccac aagagccgcc    480
atgctcgtca gagtcaacac tcttctccaa ggatactccg ggatccgatt cgagatcctc    540
gaagcgatta caagtctcct caaccacaac atctctccgt cactacctct ccgtggaacc    600
attaccgcct ccggcgatct cgttcctctc tcttacatcg ccggacttct caccggccgt    660
cctaattcca aagccaccgg tcccgacggt gaatcgctaa ccgcgaaaga agcttttgag    720
aaagccggaa tcagtactgg attcttcgat ttacaaccta aggaaggttt agctctcgtt    780
aatggcacgg cggttggatc tggaatggcg tcgatggttc tattcgaagc gaatgtccaa    840
gcggtgttag cggaggtttt atcagcgatc ttcgcggagg ttatgagcgg gaaacctgag    900
tttaccgatc atctgactca tcgtttaaaa catcatcccg gacaaatcga agcggcggcg    960
ataatggagc acatactcga cggaagctca tacatgaaat tagctcaaaa ggttcacgag    1020
atggatccat tgcagaaacc aaaacaagat cgttacgctc ttcgtacatc tcctcaatgg    1080
ctaggtcctc aaattgaagt aatccgtcaa gctacgaaat cgatagagcg tgaaatcaac    1140
tccgttaacg ataatccgtt gatcgatgtt tcgaggaaca aggcgattca cggtggtaac    1200
ttccaaggaa caccaatcgg agtttctatg gataacacga gattggcgat gctgcgatt    1260
gggaagctaa tgtttgctca attctctgag cttgttaatg atttctacaa caatggactt    1320
ccttcgaatc taactgcttc gagtaatcca agtttggatt atggattcaa aggagcagag    1380
attgctatgg cttcttattg ttctgagctt caatacttgg ctaatccagt cacaagccat    1440
gttcaatcag ctgagcaaca taatcaagat gtgaactctc ttggtttgat ctcgtctcgt    1500
aaaacatctg aagctgtgga tattcttaag ctaatgtcaa caacgttcct tgtggggata    1560
tgtcaagctg ttgatttgag acatttggag gagaatctga cacaactgt gaagaacaca    1620
gtttctcaag ttgctaagaa agtgttaacc actggaatca acggtgagtt acatccgtca    1680
aggttttgcg agaaggactt gcttaaggtt gttgatcgtg agcaagtgtt cacgtatgtg    1740
gatgatcctt gtagcgctac gtacccgttg atgcagagac taagacaagt tattgttgat    1800
cacgctttgt ccaacggtga gactgagaag aatgcagtga cttcgatctt tcaaaagatt    1860
ggagctttg aagaggagct taaggctgtg cttccaaagg aagttgaagc ggctagagcg    1920
gcttatggga tggaactgc gccgattcct aaccggatta ggaatgtag gtcgtatccg    1980
ttgtataggt tcgtgaggga agagcttgga acgaagttgt tgactggaga aaaggttgtg    2040
tctccgggag aggagtttga taaggtcttc actgctatgt gtgaaggtaa acttattgat    2100
ccgttgatgg attgtctcaa ggaatggaac ggagctccga ttccgatttg ctaa          2154
```

<210> SEQ ID NO 2
<211> LENGTH: 717
<212> TYPE: PRT
<213> ORGANISM: Arabidopsis thaliana

<400> SEQUENCE: 2

Met Asp Gln Ile Glu Ala Met Leu Cys Gly Gly Gly Glu Lys Thr Lys
1               5                   10                  15

Val Ala Val Thr Thr Lys Thr Leu Ala Asp Pro Leu Asn Trp Gly Leu
                20                  25                  30

Ala Ala Asp Gln Met Lys Gly Ser His Leu Asp Glu Val Lys Lys Met
            35                  40                  45

-continued

```
Val Glu Glu Tyr Arg Arg Pro Val Val Asn Leu Gly Gly Glu Thr Leu
 50                  55                  60

Thr Ile Gly Gln Val Ala Ala Ile Ser Thr Val Gly Gly Ser Val Lys
 65                  70                  75                  80

Val Glu Leu Ala Glu Thr Ser Arg Ala Gly Val Lys Ala Ser Ser Asp
                 85                  90                  95

Trp Val Met Glu Ser Met Asn Lys Gly Thr Asp Ser Tyr Gly Val Thr
                100                 105                 110

Thr Gly Phe Gly Ala Thr Ser His Arg Arg Thr Lys Asn Gly Thr Ala
            115                 120                 125

Leu Gln Thr Glu Leu Ile Arg Phe Leu Asn Ala Gly Ile Phe Gly Asn
            130                 135                 140

Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
                165                 170                 175

Phe Glu Ile Leu Glu Ala Ile Thr Ser Leu Leu Asn His Asn Ile Ser
                180                 185                 190

Pro Ser Leu Pro Leu Arg Gly Thr Ile Thr Ala Ser Gly Asp Leu Val
            195                 200                 205

Pro Leu Ser Tyr Ile Ala Gly Leu Leu Thr Gly Arg Pro Asn Ser Lys
210                 215                 220

Ala Thr Gly Pro Asp Gly Glu Ser Leu Thr Ala Lys Glu Ala Phe Glu
225                 230                 235                 240

Lys Ala Gly Ile Ser Thr Gly Phe Phe Asp Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
            275                 280                 285

Ala Ile Phe Ala Glu Val Met Ser Gly Lys Pro Glu Phe Thr Asp His
290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
                325                 330                 335

Lys Val His Glu Met Asp Pro Leu Gln Lys Pro Lys Gln Asp Arg Tyr
            340                 345                 350

Ala Leu Arg Thr Ser Pro Gln Trp Leu Gly Pro Gln Ile Glu Val Ile
            355                 360                 365

Arg Gln Ala Thr Lys Ser Ile Glu Arg Glu Ile Asn Ser Val Asn Asp
370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
                405                 410                 415

Ile Ala Ala Ile Gly Lys Leu Met Phe Ala Gln Phe Ser Glu Leu Val
            420                 425                 430

Asn Asp Phe Tyr Asn Asn Gly Leu Pro Ser Asn Leu Thr Ala Ser Ser
            435                 440                 445

Asn Pro Ser Leu Asp Tyr Gly Phe Lys Gly Ala Glu Ile Ala Met Ala
450                 455                 460

Ser Tyr Cys Ser Glu Leu Gln Tyr Leu Ala Asn Pro Val Thr Ser His
```

| | | | | | | | | 465 | | | | 470 | | | | 475 | | | | 480 |
|---|---|---|---|---|---|---|---|---|---|---|---|---|---|---|---|---|---|---|---|---|

Val Gln Ser Ala Glu Gln His Asn Gln Asp Val Asn Ser Leu Gly Leu
                                      485                          490                          495

Ile Ser Ser Arg Lys Thr Ser Glu Ala Val Asp Ile Leu Lys Leu Met
                  500                          505                          510

Ser Thr Thr Phe Leu Val Gly Ile Cys Gln Ala Val Asp Leu Arg His
            515                          520                          525

Leu Glu Glu Asn Leu Arg Gln Thr Val Lys Asn Thr Val Ser Gln Val
        530                          535                          540

Ala Lys Lys Val Leu Thr Thr Gly Ile Asn Gly Glu Leu His Pro Ser
545                  550                          555                        560

Arg Phe Cys Glu Lys Asp Leu Leu Lys Val Val Asp Arg Glu Gln Val
                  565                          570                          575

Phe Thr Tyr Val Asp Asp Pro Cys Ser Ala Thr Tyr Pro Leu Met Gln
            580                          585                          590

Arg Leu Arg Gln Val Ile Val Asp His Ala Leu Ser Asn Gly Glu Thr
        595                          600                          605

Glu Lys Asn Ala Val Thr Ser Ile Phe Gln Lys Ile Gly Ala Phe Glu
        610                          615                          620

Glu Glu Leu Lys Ala Val Leu Pro Lys Glu Val Glu Ala Ala Arg Ala
625                  630                          635                        640

Ala Tyr Gly Asn Gly Thr Ala Pro Ile Pro Asn Arg Ile Lys Glu Cys
                  645                          650                        655

Arg Ser Tyr Pro Leu Tyr Arg Phe Val Arg Glu Glu Leu Gly Thr Lys
            660                          665                          670

Leu Leu Thr Gly Glu Lys Val Val Ser Pro Gly Glu Glu Phe Asp Lys
        675                          680                          685

Val Phe Thr Ala Met Cys Glu Gly Lys Leu Ile Asp Pro Leu Met Asp
        690                          695                          700

Cys Leu Lys Glu Trp Asn Gly Ala Pro Ile Pro Ile Cys
705                  710                          715

<210> SEQ ID NO 3
<211> LENGTH: 1686
<212> TYPE: DNA
<213> ORGANISM: Arabidopsis thaliana

<400> SEQUENCE: 3

| | |
|---|---|
| atggcgccac aagaacaagc agtttctcag gtgatggaga aacagagcaa caacaacaac | 60 |
| agtgacgtca ttttccgatc aaagttaccg gatatttaca tcccgaacca cctatctctc | 120 |
| cacgactaca tcttccaaaa catctccgaa ttcgccacta gccttgcct aatcaacgga | 180 |
| ccaaccggcc acgtgtacac ttactccgac gtccacgtca tctcccgcca aatcgccgcc | 240 |
| aattttcaca actcggcgt taaccaaaac gacgtcgtca tgctcctcct cccaaactgt | 300 |
| cccgaattcg tcctctcttt cctcgccgcc tccttccgcg gcgcaaccgc caccgccgca | 360 |
| aaccctttct tcactccggc ggagatagct aaacaagcca agcctccaa caccaaactc | 420 |
| ataatcaccg aagctcgtta cgtcgacaaa atcaaaccac ttcaaaacga cgacggagta | 480 |
| gtcatcgtct gcatcgacga caacgaatcc gtgccaatcc tgaaggctg cctccgcttc | 540 |
| accgagttga ctcagtcgac aaccgaggca tcagaagtca tcgactcggt ggagatttca | 600 |
| ccggacgacg tggtggcact accttactcc tctggcacga cgggattacc aaaaggagtg | 660 |
| atgctgactc acaagggact agtcacgagc gttgctcagc aagtcgacgg cgagaacccg | 720 |
| aatctttatt tccacagcga tgacgtcata ctctgtgttt tgcccatgtt tcatatctac | 780 |

```
gctttgaact cgatcatgtt gtgtggtctt agagttggtg cggcgattct gataatgccg    840
aagtttgaga tcaatctgct attggagctg atccagaggt gtaaagtgac ggtggctccg    900
atggttccgc cgattgtgtt ggccattgcg aagtcttcgg agacggagaa gtatgatttg    960
agctcgataa gagtggtgaa atctggtgct gctcctcttg gtaaagaact tgaagatgcc   1020
gttaatgcca agtttcctaa tgccaaactc ggtcagggat acggaatgac ggaagcaggt   1080
ccagtgctag caatgtcgtt aggttttgca aaggaacctt ttccggttaa gtcaggagct   1140
tgtggtactg ttgtaagaaa tgctgagatg aaaatagttg atccagacac cggagattct   1200
ctttcgagga atcaacccgg tgagatttgt attcgtggtc accagatcat gaaaggttac   1260
ctcaacaatc cggcagctac agcagagacc attgataaag acggttggct tcatactgga   1320
gatattggat tgatcgatga cgatgacgag cttttcatcg ttgatcgatt gaagaacttt   1380
atcaagtata aggttttca ggtagctccg gctgagctag aggctttgct catcggtcat   1440
cctgacatta ctgatgttgc tgttgtcgca atgaaagaag aagcagctgg tgaagttcct   1500
gttgcatttg tggtgaaatc gaaggattcg gagttatcag aagatgatgt gaagcaattc   1560
gtgtcgaaac aggttgtgtt ttacaagaga atcaacaaag tgttcttcac tgaatccatt   1620
cctaaagctc catcagggaa gatattgagg aaagatctga gggcaaaact agcaaatgga   1680
ttgtga                                                              1686

<210> SEQ ID NO 4
<211> LENGTH: 561
<212> TYPE: PRT
<213> ORGANISM: Arabidopsis thaliana

<400> SEQUENCE: 4

Met Ala Pro Gln Glu Gln Ala Val Ser Gln Val Met Glu Lys Gln Ser
1               5                   10                  15

Asn Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
            100                 105                 110

Arg Gly Ala Thr Ala Thr Ala Ala Asn Pro Phe Phe Thr Pro Ala Glu
        115                 120                 125

Ile Ala Lys Gln Ala Lys Ala Ser Asn Thr Lys Leu Ile Ile Thr Glu
    130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Asp Val Val Ala Leu Pro
        195                 200                 205
```

| | | | | | | | | | | | |
|---|---|---|---|---|---|---|---|---|---|---|---|
|Tyr|Ser|Ser|Gly|Thr|Thr|Gly|Leu|Pro|Lys|Gly|Val|Met|Leu|Thr|His|
| |210| | | |215| | | |220| | |

Tyr Ser Ser Gly Thr Thr Gly Leu Pro Lys Gly Val Met Leu Thr His
    210                 215                 220

Lys Gly Leu Val Thr Ser Val Ala Gln Gln Val Asp Gly Glu Asn Pro
225                 230                 235                 240

Asn Leu Tyr Phe His Ser Asp Asp Val Ile Leu Cys Val Leu Pro Met
                245                 250                 255

Phe His Ile Tyr Ala Leu Asn Ser Ile Met Leu Cys Gly Leu Arg Val
            260                 265                 270

Gly Ala Ala Ile Leu Ile Met Pro Lys Phe Glu Ile Asn Leu Leu Leu
        275                 280                 285

Glu Leu Ile Gln Arg Cys Lys Val Thr Val Ala Pro Met Val Pro Pro
    290                 295                 300

Ile Val Leu Ala Ile Ala Lys Ser Ser Glu Thr Glu Lys Tyr Asp Leu
305                 310                 315                 320

Ser Ser Ile Arg Val Val Lys Ser Gly Ala Ala Pro Leu Gly Lys Glu
                325                 330                 335

Leu Glu Asp Ala Val Asn Ala Lys Phe Pro Asn Ala Lys Leu Gly Gln
            340                 345                 350

Gly Tyr Gly Met Thr Glu Ala Gly Pro Val Leu Ala Met Ser Leu Gly
        355                 360                 365

Phe Ala Lys Glu Pro Phe Pro Val Lys Ser Gly Ala Cys Gly Thr Val
    370                 375                 380

Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
                405                 410                 415

Met Lys Gly Tyr Leu Asn Asn Pro Ala Ala Thr Ala Glu Thr Ile Asp
            420                 425                 430

Lys Asp Gly Trp Leu His Thr Gly Asp Ile Gly Leu Ile Asp Asp Asp
        435                 440                 445

Asp Glu Leu Phe Ile Val Asp Arg Leu Lys Glu Leu Ile Lys Tyr Lys
    450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
                485                 490                 495

Gly Glu Val Pro Val Ala Phe Val Val Lys Ser Lys Asp Ser Glu Leu
            500                 505                 510

Ser Glu Asp Asp Val Lys Gln Phe Val Ser Lys Gln Val Val Phe Tyr
        515                 520                 525

Lys Arg Ile Asn Lys Val Phe Phe Thr Glu Ser Ile Pro Lys Ala Pro
    530                 535                 540

Ser Gly Lys Ile Leu Arg Lys Asp Leu Arg Ala Lys Leu Ala Asn Gly
545                 550                 555                 560

Leu

<210> SEQ ID NO 5
<211> LENGTH: 1176
<212> TYPE: DNA
<213> ORGANISM: Rheum tataricum

<400> SEQUENCE: 5
atggcaccgg aggagtccag gcatgctgaa actgcagtta acagagccgc caccgtcctg     60
gccatcggca ctgccaaccc gccaaactgc tactatcaag cggactttcc tgacttctac    120

-continued

```
ttccgtgcca ccaacagcga ccacctcacg cacctcaagc aaaaatttaa gcgcatttgt    180
gagaaatcga tgattgaaaa acgttatctc catttgacgg aagaaattct caaggagaat    240
ccaaatattg cttccttcga ggcgccatca ttggatgtaa acataacat tcaagtgaaa    300
gaagtggtgc tgctcggaaa agaggcagct ttgaaggcca tcaatgagtg gggccaaccc    360
aagtcaaaga tcacgcgcct cattgtgtgt tgtattgccg gcgttgacat gcccggcgca    420
gactatcaac tcactaaact ccttggctta caactttctg ttaagcgatt tatgttttac    480
cacctaggat gctatgccgg tggcaccgtc cttcgccttg cgaaggacat agcagaaaac    540
aacaaggaag ctcgtgttct catcgttcgc tctgagatga cgccaatctg tttccgtggg    600
ccatccgaaa cccacataga ctccatggta gggcaagcaa tatttggtga cggtgctgcg    660
gctgttatag ttggtgcaaa tcccgaccta tccatcgaaa ggccgatttt cgagttgatt    720
tctacatccc aaactatcat acctgaatcc gatggtgcga ttgagggaca tttgcttgaa    780
gttggactca gtttccaact ctaccagact gttccctcat taatctctaa ttgtatcgaa    840
acttgtcttt caaaggcttt cacacctctt aacattagtg attggaactc actattctgg    900
attgcacacc ctggtggccg tgctatcctt gacgatatcg aggctactgt tggtctcaag    960
aaggagaaac ttaaggcaac aagacaagtt ttgaacgact atgggaacat gtcaagtgct   1020
tgcgtatttt tcatcatgga tgagatgagg aagaagtcgc tcgcaaacgg tcaagtaacc   1080
actgagaag gactcaagtg gggtgttctt tttgggttcg ggccaggtgt tactgtgaa    1140
actgtggttc taagcagtgt gccgctaatt acctga                             1176
```

<210> SEQ ID NO 6
<211> LENGTH: 391
<212> TYPE: PRT
<213> ORGANISM: Rheum tataricum

<400> SEQUENCE: 6

```
Met Ala Pro Glu Glu Ser Arg His Ala Glu Thr Ala Val Asn Arg Ala
1               5                   10                  15

Ala Thr Val Leu Ala Ile Gly Thr Ala Asn Pro Pro Asn Cys Tyr Tyr
            20                  25                  30

Gln Ala Asp Phe Pro Asp Phe Tyr Phe Arg Ala Thr Asn Ser Asp His
        35                  40                  45

Leu Thr His Leu Lys Gln Lys Phe Lys Arg Ile Cys Glu Lys Ser Met
    50                  55                  60

Ile Glu Lys Arg Tyr Leu His Leu Thr Glu Glu Ile Leu Lys Glu Asn
65                  70                  75                  80

Pro Asn Ile Ala Ser Phe Glu Ala Pro Ser Leu Asp Val Arg His Asn
                85                  90                  95

Ile Gln Val Lys Glu Val Val Leu Leu Gly Lys Glu Ala Ala Leu Lys
            100                 105                 110

Ala Ile Asn Glu Trp Gly Gln Pro Lys Ser Lys Ile Thr Arg Leu Ile
        115                 120                 125

Val Cys Cys Ile Ala Gly Val Asp Met Pro Gly Ala Asp Tyr Gln Leu
    130                 135                 140

Thr Lys Leu Leu Gly Leu Gln Leu Ser Val Lys Arg Phe Met Phe Tyr
145                 150                 155                 160

His Leu Gly Cys Tyr Ala Gly Gly Thr Val Leu Arg Leu Ala Lys Asp
                165                 170                 175

Ile Ala Glu Asn Asn Lys Glu Ala Arg Val Leu Ile Val Arg Ser Glu
            180                 185                 190
```

```
Met Thr Pro Ile Cys Phe Arg Gly Pro Ser Glu Thr His Ile Asp Ser
        195                 200                 205
Met Val Gly Gln Ala Ile Phe Gly Asp Gly Ala Ala Val Ile Val
    210                 215                 220
Gly Ala Asn Pro Asp Leu Ser Ile Glu Arg Pro Ile Phe Glu Leu Ile
225                 230                 235                 240
Ser Thr Ser Gln Thr Ile Ile Pro Glu Ser Asp Gly Ala Ile Glu Gly
                245                 250                 255
His Leu Leu Glu Val Gly Leu Ser Phe Gln Leu Tyr Gln Thr Val Pro
            260                 265                 270
Ser Leu Ile Ser Asn Cys Ile Glu Thr Cys Leu Ser Lys Ala Phe Thr
        275                 280                 285
Pro Leu Asn Ile Ser Asp Trp Asn Ser Leu Phe Trp Ile Ala His Pro
    290                 295                 300
Gly Gly Arg Ala Ile Leu Asp Asp Ile Glu Ala Thr Val Gly Leu Lys
305                 310                 315                 320
Lys Glu Lys Leu Lys Ala Thr Arg Gln Val Leu Asn Asp Tyr Gly Asn
                325                 330                 335
Met Ser Ser Ala Cys Val Phe Phe Ile Met Asp Glu Met Arg Lys Lys
            340                 345                 350
Ser Leu Ala Asn Gly Gln Val Thr Thr Gly Glu Gly Leu Lys Trp Gly
        355                 360                 365
Val Leu Phe Gly Phe Gly Pro Gly Val Thr Val Glu Thr Val Val Leu
    370                 375                 380
Ser Ser Val Pro Leu Ile Thr
385                 390

<210> SEQ ID NO 7
<211> LENGTH: 1176
<212> TYPE: DNA
<213> ORGANISM: Rheum tataricum

<400> SEQUENCE: 7
atggccccag aagagagcag gcacgcagaa acggccgtta acagagctgc aactgttttg      60
gctattggta cggccaatcc acccaattgt tactatcaag ctgactttcc tgatttttat     120
ttcagagcca caaatagcga tcatttgact catcttaagc aaaaatttaa aaggatatgc     180
gagaagtcca tgattgaaaa gagatacttg caccttaccg aagagatctt aaaagaaaac     240
ccaaatatag cttcttttga agctccctcc ttagatgtac gtcacaacat tcaagtcaag     300
gaggtggttt tacttggtaa ggaagccgca ttgaaagcta taaacgaatg gggacagcct     360
aaaagtaaga taaccagatt gatcgtatgt tgcatagctg gcgttgacat gcctggtgca     420
gattatcaac taacaaaatt gctgggtcta caattatccg taaaaggtt atgttctac     480 catttaggct gttacgctgg tggcacagtt ttaagactgg ctaaggatat agcagaaaat     540
aacaaggagg ctagagtctt aatagtgcgt agtgaaatga ctcctatttg ctttagaggt     600
ccatcagaaa cacatatcga cagcatggta ggtcaggcaa ttttcggtga tggtgctgca     660
gccgtaattg tgggagctaa tcctgattta agtatcgaaa gacctatttt tgaacttatt     720
tctacttcgc aaaccattat ccccgaatca gatggtgcaa ttgaaggcca tttattggag     780
gttggtttgt cctttcaatt gtatcagaca gtgccatctt taatttcaaa ctgtatagaa     840
acctgtctaa gtaaagcatt tacaccatta acatttctg actggaattc tttgttctgg     900
attgctcatc caggtggaag agccatctta gatgacatcg aagctactgt gggactgaaa     960
aaggaaaaac taaaagctac tagacaagtt ttaaatgact acggtaatat gtcatctgct    1020
```
tgtgtatttt tcattatgga tgagatgaga aaaaagtcac ttgcaaatgg ccaggtcacg    1080
acaggtgagg gtctaaaatg gggagtccta ttcggattcg ccccaggtgt cactgttgaa    1140
accgttgtcc tgtcttcggt tccattgatc acttaa                              1176

<210> SEQ ID NO 8
<211> LENGTH: 391
<212> TYPE: PRT
<213> ORGANISM: Rheum tataricum

<400> SEQUENCE: 8

Met Ala Pro Glu Glu Ser Arg His Ala Glu Thr Ala Val Asn Arg Ala
1               5                   10                  15

Ala Thr Val Leu Ala Ile Gly Thr Ala Asn Pro Pro Asn Cys Tyr Tyr
            20                  25                  30

Gln Ala Asp Phe Pro Asp Phe Tyr Phe Arg Ala Thr Asn Ser Asp His
        35                  40                  45

Leu Thr His Leu Lys Gln Lys Phe Lys Arg Ile Cys Glu Lys Ser Met
    50                  55                  60

Ile Glu Lys Arg Tyr Leu His Leu Thr Glu Glu Ile Leu Lys Glu Asn
65                  70                  75                  80

Pro Asn Ile Ala Ser Phe Glu Ala Pro Ser Leu Asp Val Arg His Asn
                85                  90                  95

Ile Gln Val Lys Glu Val Val Leu Leu Gly Lys Glu Ala Ala Leu Lys
            100                 105                 110

Ala Ile Asn Glu Trp Gly Gln Pro Lys Ser Lys Ile Thr Arg Leu Ile
        115                 120                 125

Val Cys Cys Ile Ala Gly Val Asp Met Pro Gly Ala Asp Tyr Gln Leu
    130                 135                 140

Thr Lys Leu Leu Gly Leu Gln Leu Ser Val Lys Arg Phe Met Phe Tyr
145                 150                 155                 160

His Leu Gly Cys Tyr Ala Gly Gly Thr Val Leu Arg Leu Ala Lys Asp
                165                 170                 175

Ile Ala Glu Asn Asn Lys Glu Ala Arg Val Leu Ile Val Arg Ser Glu
            180                 185                 190

Met Thr Pro Ile Cys Phe Arg Gly Pro Ser Glu Thr His Ile Asp Ser
        195                 200                 205

Met Val Gly Gln Ala Ile Phe Gly Asp Gly Ala Ala Ala Val Ile Val
    210                 215                 220

Gly Ala Asn Pro Asp Leu Ser Ile Glu Arg Pro Ile Phe Glu Leu Ile
225                 230                 235                 240

Ser Thr Ser Gln Thr Ile Ile Pro Glu Ser Asp Gly Ala Ile Glu Gly
                245                 250                 255

His Leu Leu Glu Val Gly Leu Ser Phe Gln Leu Tyr Gln Thr Val Pro
            260                 265                 270

Ser Leu Ile Ser Asn Cys Ile Glu Thr Cys Leu Ser Lys Ala Phe Thr
        275                 280                 285

Pro Leu Asn Ile Ser Asp Trp Asn Ser Leu Phe Trp Ile Ala His Pro
    290                 295                 300

Gly Gly Arg Ala Ile Leu Asp Asp Ile Glu Ala Thr Val Gly Leu Lys
305                 310                 315                 320

Lys Glu Lys Leu Lys Ala Thr Arg Gln Val Leu Asn Asp Tyr Gly Asn
                325                 330                 335

Met Ser Ser Ala Cys Val Phe Phe Ile Met Asp Glu Met Arg Lys Lys
            340                 345                 350

Ser Leu Ala Asn Gly Gln Val Thr Thr Gly Glu Gly Leu Lys Trp Gly
        355                 360                 365

Val Leu Phe Gly Phe Gly Pro Gly Val Thr Val Glu Thr Val Val Leu
    370                 375                 380

Ser Ser Val Pro Leu Ile Thr
385                 390

<210> SEQ ID NO 9
<211> LENGTH: 1182
<212> TYPE: DNA
<213> ORGANISM: Vitis vinifera

<400> SEQUENCE: 9
atggcatccg tagaggagtt cagaaatgca cagagggcaa aaggtccagc aaccatattg      60
gctattggaa cagccacccc tgatcactgt gtttatcaat ctgattacgc tgattactat     120
ttcagagtaa ctaaaagtga acatatgaca gaacttaaga aaaagtttaa tagaatttgt     180
gataaatcta tgataaagaa aagatacata catctaactg aagaaatgtt agaggaacat     240
ccaaatatag gtgcatatat ggcaccatct ttgaatatta caagaaaat cataacagcc      300
gaggtaccta gactaggtag agacgcagcc ttgaaagctt taaggaatg gggacaacca      360
aaatctaaga ttacacattt ggttttctgt acaacttccg gtgtcgaaat gccaggtgct     420
gattataaac tagcaaacct attgggatta gagacctctg ttagaagagt tatgttgtat     480
catcaaggtt gttacgccgg aggtacagtg cttagaactg ctaaggattt ggcagaaaat     540
aacgccggtg ctagggtttt agtcgtctgc agtgaaatca ctgtcgtaac tttcagaggt     600
ccatcagaag atgctctaga cagtttggtc ggacaagcat tgtttggcga tggatcttcc     660
gccgtaattg taggcagcga tcctgatgtg tccattgaaa gaccactatt tcaattagtt     720
tctgctgctc aaacttttat tccaaattcc gccggtgcca tagcaggaaa cttgagagaa     780
gttggtttga ctttcatttt gtggcctaat gtcccaacct taatttcaga aacatcgaa      840
aaatgcttaa ctcaagcctt tgacccattg gcataagcg actggaactc attgttttgg     900
attgctcatc aggtggtccc agcaattta gacgcagtgg aggcaaaact aaacttagag      960
aagaaaaagt tggaagctac aagacacgtt ctatcagagt atggcaacat gagctctgcc    1020
tgcgtttat tcattctaga tgagatgagg aagaagtctt taaagggtga aaagccaca     1080
accggagaag gtttagattg gggtgttcta tttggtttcg gtcctggctt aacaattgag    1140
acagtggtgt tacactctgt tccaactgtc actaactaat ga                       1182

<210> SEQ ID NO 10
<211> LENGTH: 392
<212> TYPE: PRT
<213> ORGANISM: Vitis vinifera

<400> SEQUENCE: 10

Met Ala Ser Val Glu Glu Phe Arg Asn Ala Gln Arg Ala Lys Gly Pro
1               5                   10                  15

Ala Thr Ile Leu Ala Ile Gly Thr Ala Thr Pro Asp His Cys Val Tyr
            20                  25                  30

Gln Ser Asp Tyr Ala Asp Tyr Tyr Phe Arg Val Thr Lys Ser Glu His
        35                  40                  45

Met Thr Glu Leu Lys Lys Lys Phe Asn Arg Ile Cys Asp Lys Ser Met
    50                  55                  60

Ile Lys Lys Arg Tyr Ile His Leu Thr Glu Glu Met Leu Glu Glu His
65                  70                  75                  80

```
Pro Asn Ile Gly Ala Tyr Met Ala Pro Ser Leu Asn Ile Arg Gln Glu
                85                  90                  95
Ile Ile Thr Ala Glu Val Pro Arg Leu Gly Arg Asp Ala Ala Leu Lys
            100                 105                 110
Ala Leu Lys Glu Trp Gly Gln Pro Lys Ser Lys Ile Thr His Leu Val
        115                 120                 125
Phe Cys Thr Thr Ser Gly Val Glu Met Pro Gly Ala Asp Tyr Lys Leu
130                 135                 140
Ala Asn Leu Leu Gly Leu Glu Thr Ser Val Arg Arg Val Met Leu Tyr
145                 150                 155                 160
His Gln Gly Cys Tyr Ala Gly Gly Thr Val Leu Arg Thr Ala Lys Asp
                165                 170                 175
Leu Ala Glu Asn Asn Ala Gly Ala Arg Val Leu Val Val Cys Ser Glu
            180                 185                 190
Ile Thr Val Val Thr Phe Arg Gly Pro Ser Glu Asp Ala Leu Asp Ser
        195                 200                 205
Leu Val Gly Gln Ala Leu Phe Gly Asp Gly Ser Ser Ala Val Ile Val
210                 215                 220
Gly Ser Asp Pro Asp Val Ser Ile Glu Arg Pro Leu Phe Gln Leu Val
225                 230                 235                 240
Ser Ala Ala Gln Thr Phe Ile Pro Asn Ser Ala Gly Ala Ile Ala Gly
                245                 250                 255
Asn Leu Arg Glu Val Gly Leu Thr Phe His Leu Trp Pro Asn Val Pro
            260                 265                 270
Thr Leu Ile Ser Glu Asn Ile Glu Lys Cys Leu Thr Gln Ala Phe Asp
        275                 280                 285
Pro Leu Gly Ile Ser Asp Trp Asn Ser Leu Phe Trp Ile Ala His Pro
290                 295                 300
Gly Gly Pro Ala Ile Leu Asp Ala Val Glu Ala Lys Leu Asn Leu Glu
305                 310                 315                 320
Lys Lys Lys Leu Glu Ala Thr Arg His Val Leu Ser Glu Tyr Gly Asn
                325                 330                 335
Met Ser Ser Ala Cys Val Leu Phe Ile Leu Asp Glu Met Arg Lys Lys
            340                 345                 350
Ser Leu Lys Gly Glu Lys Ala Thr Thr Gly Glu Gly Leu Asp Trp Gly
        355                 360                 365
Val Leu Phe Gly Phe Gly Pro Gly Leu Thr Ile Glu Thr Val Val Leu
370                 375                 380
His Ser Val Pro Thr Val Thr Asn
385                 390

<210> SEQ ID NO 11
<211> LENGTH: 33
<212> TYPE: DNA
<213> ORGANISM: Arabidopsis thaliana

<400> SEQUENCE: 11
cggaattctc atggatcaaa tcgaagcaat gtt                                  33

<210> SEQ ID NO 12
<211> LENGTH: 29
<212> TYPE: DNA
<213> ORGANISM: Arabidopsis thaliana

<400> SEQUENCE: 12
cgactagttt agcaaatcgg aatcggagc                                       29
```

```
<210> SEQ ID NO 13
<211> LENGTH: 36
<212> TYPE: DNA
<213> ORGANISM: Arabidopsis thaliana

<400> SEQUENCE: 13
gctctagacc tatggcgcca caagaacaag cagttt                                    36

<210> SEQ ID NO 14
<211> LENGTH: 36
<212> TYPE: DNA
<213> ORGANISM: Arabidopsis thaliana

<400> SEQUENCE: 14
gcggatcccc ttcacaatcc atttgctagt tttgcc                                    36

<210> SEQ ID NO 15
<211> LENGTH: 31
<212> TYPE: DNA
<213> ORGANISM: Rheum tartaricum

<400> SEQUENCE: 15
ccggatccaa atggccccag aagagagcag g                                         31

<210> SEQ ID NO 16
<211> LENGTH: 35
<212> TYPE: DNA
<213> ORGANISM: Rheum tartaricum

<400> SEQUENCE: 16
cgctcgagtt aagtgatcaa tggaaccgaa gacag                                     35

<210> SEQ ID NO 17
<211> LENGTH: 32
<212> TYPE: DNA
<213> ORGANISM: Aspergillus nidulans

<400> SEQUENCE: 17
cggaattcat acgcggtttt ttggggtagt ca                                        32

<210> SEQ ID NO 18
<211> LENGTH: 32
<212> TYPE: DNA
<213> ORGANISM: Aspergillus nidulans

<400> SEQUENCE: 18
cgcccgggta tgccacctac agccattgcg aa                                        32

<210> SEQ ID NO 19
<211> LENGTH: 32
<212> TYPE: DNA
<213> ORGANISM: Aspergillus nidulans

<400> SEQUENCE: 19
gcggatccat agggcgctta cacagtacac ga                                        32

<210> SEQ ID NO 20
<211> LENGTH: 48
<212> TYPE: DNA
<213> ORGANISM: Aspergillus nidulans

<400> SEQUENCE: 20
cggagagggc gcgcccgtgg cggccgcgga tccacttaac gttactga                       48
```

<210> SEQ ID NO 21
<211> LENGTH: 48
<212> TYPE: DNA
<213> ORGANISM: Aspergillus nidulans

<400> SEQUENCE: 21
gcggccgcca cgggcgcgcc ctctccggcg gtagtgatgt ctgctcaa            48

<210> SEQ ID NO 22
<211> LENGTH: 32
<212> TYPE: DNA
<213> ORGANISM: Aspergillus nidulans

<400> SEQUENCE: 22
cgaagcttta taattcccctt gtatctctac ac                            32

<210> SEQ ID NO 23
<211> LENGTH: 32
<212> TYPE: DNA
<213> ORGANISM: Artificial
<220> FEATURE:
<223> OTHER INFORMATION: Plasmid based pcr primer for gene C4H

<400> SEQUENCE: 23
cggcgcgcat aatggacctc ctcttgctgg ag                             32

<210> SEQ ID NO 24
<211> LENGTH: 38
<212> TYPE: DNA
<213> ORGANISM: Artificial
<220> FEATURE:
<223> OTHER INFORMATION: Plasmid based PCR primer for gene C4H

<400> SEQUENCE: 24
gggcggccgc ttattaacag ttccttggtt tcataacg                       38

<210> SEQ ID NO 25
<211> LENGTH: 56
<212> TYPE: DNA
<213> ORGANISM: Aspergillus fumigatus

<400> SEQUENCE: 25
cgtgtacaat attaattaac gagagcgatc gcaataaccg tattaccgcc tttgag   56

<210> SEQ ID NO 26
<211> LENGTH: 32
<212> TYPE: DNA
<213> ORGANISM: Aspergillus fumigatus

<400> SEQUENCE: 26
cgacatgtat tcccgggaag atctcatggt ca                             32

<210> SEQ ID NO 27
<211> LENGTH: 35
<212> TYPE: DNA
<213> ORGANISM: Artificial
<220> FEATURE:
<223> OTHER INFORMATION: Plasmid based PCR primer for gene VST1

<400> SEQUENCE: 27
gcggagaggg cgcgatggcg ccacaagaac aagca                          35

<210> SEQ ID NO 28
<211> LENGTH: 39

```
<212> TYPE: DNA
<213> ORGANISM: Artificial
<220> FEATURE:
<223> OTHER INFORMATION: Plasmid based primer for gene VST1

<400> SEQUENCE: 28
tggatccgcg gccgctcaca atccatttgc tagttttgc                    39

<210> SEQ ID NO 29
<211> LENGTH: 32
<212> TYPE: DNA
<213> ORGANISM: Artificial
<220> FEATURE:
<223> OTHER INFORMATION: Plasmid based PCR primer sequence for gene VST1

<400> SEQUENCE: 29
cggcgcgcat aatggcatcc gtagaggagt tc                           32

<210> SEQ ID NO 30
<211> LENGTH: 36
<212> TYPE: DNA
<213> ORGANISM: Artificial
<220> FEATURE:
<223> OTHER INFORMATION: Plasmid based PCR primer sequence for gene VST1

<400> SEQUENCE: 30
gggcggccgc ttatcattag ttagtgacag ttggaa                       36
```

METABOLICALLY ENGINEERED CELLS FOR THE PRODUCTION OF PINOSYLVIN

FIELD OF THE INVENTION

This invention relates generally to the production of the polyphenol pinosylvin. Furthermore, it relates to the use of naturally occurring or recombinant micro-organisms that produce pinosylvin for production of food, feed and beverages.

BACKGROUND OF THE INVENTION

Production of chemicals from micro-organisms has been an important application of biotechnology. Typically, the steps in developing such a bio-production method may include 1) selection of a proper micro-organism host, 2) elimination of metabolic pathways leading to by-products, 3) deregulation of desired pathways at both enzyme activity level and the transcriptional level, and 4) overexpression of appropriate enzymes in the desired pathways. In preferred aspects, the present invention has employed combinations of the steps above to redirect carbon flow from phenylalanine through enzymes of the plant phenylpropanoid pathway which supplies the necessary precursor for the desired biosynthesis of pinosylvin.

Pinosylvin (or pinosylvine or 3,5-dihydroxy-trans-stilbene) is a phytophenol belonging to the group of stilbene phytoalexins, which are low-molecular-mass secondary metabolites that constitute the active defence mechanism in plants in response to infections or other stress-related events. Stilbene phytoalexins contain the stilbene skeleton (trans-1,2-diphenylethylene) as their common basic structure: that may be supplemented by addition of other groups as well (Hart and Shrimpton, 1979, Hart, 1981). Stilbenes have been found in certain trees (angio-sperms, gymnosperms), but also in some herbaceous plants (in species of the Myrtaceae, Vitaceae and Leguminosae families). Said compounds are toxic to pests, especially to fungi, bacteria and insects. Only few plants have the ability to synthesize stilbenes, or to produce them in an amount that provides them sufficient resistance to pests.

The synthesis of the basic stilbene skeleton is pursued by stilbene syntheses, which comprises a small gene family in most species examined (Kodan et al. 2002). Stilbene syntheses appear to have evolved from chalcone syntheses, and belong to a polyketide synthase (PKS) superfamily that share more than 65% amino acid homology. Unlike the bacterial PKSs, both stilbene- and chalcone syntheses function as unimodular PKSs with a single active site, forming relatively small homodimers (Tropf et al., 1995). Stilbene- and chalcone syntheses use common substrates, three malonyl-CoAs and one cinnamoyl-CoA/p-coumaroyl-CoA, forming their products with similar reaction mechanisms (Kindl, 1985). Stilbene syntheses can be classified into either a 4-coumaroyl-CoA-specific type that has its highest activity with 4-coumaroyl-CoA as substrate, such as resveratrol synthase (EC 2.3.1.95), or a cinnamoyl-CoA-specific type that has its highest activity with cinnamoyl-CoA as substrate, such as pinosylvin synthase (EC 2.3.1.146). Genes encoding resveratrol syntheses have been described earlier for peanut (*Arachis hypogaea*) (Schöppner and Kindl, 1984; Schröder et al., 1988) and grapevine (*Vitis vinifera*) (Melchior and Kindl, 1991; Wiese et al., 1994) whereas genes encoding pinosylvin synthase have been mostly described for pine (*Pinus sylvestris* and *-strobus*) (Schanz et al., 1992; Raiber et al., 1995; Kodan et al., 2002; Hemingway et al., 1977).

Pinosylvin is present in the wood pulp of eucalyptus-, spruce- and pine trees such as *Pinus sylvestris, -densiflora, -taeda* and *-strobus*. In pine species, the constitutive pinosylvin occurs exclusively in the heartwood (Kindl, 1985). However, the compound is induced in the sapwood, phloem, and needles as a response to wounding, fungal attack or environmental stress such as UV-radiation and ozone exposure (Hart, 1981; Kindl, 1985; Richter and Wild, 1992; Lieutier et al., 1996; Rosemann et al., 1991). The compound possesses potent anti-fungal activity against a wide assortment of fungi (Lindberg et al., 2004; Pacher et al., 2002).

Pinosylvin (FIG. 1 trans-form) consists of two closely connected phenol rings and belongs therefore to the polyphenols. Unlike most other hydroxystilbenes, pinosylvin lacks a hydroxyl group in ring B (FIG. 1) and originates by condensation of unsubstituted cinnamoyl-CoA with three molecules of malonyl-CoA. That said, pinosylvin is structurally similar to the tri-hydroxystilbene resveratrol, which is found in red wine (Aggarwal et al., 2004). Much data has been generated demonstrating the health benefits of resveratrol. For instance resveratrol's potent anticancer activity across many cancer cell lines has well been established (Aggarwal et al., 2004). Given the similarity in structure with resveratrol, it is anticipated that pinosylvin possesses potent health benefits as well. Indeed pinosylvin's effect on various cancers, including colorectal- and liver cancers, has been studied, and has indicated it's chemopreventative- and anti-leukemic activity (Skinnider and Stoessl, 1986; Mellanen et al., 1996; Roupe et al., 2005 and 2006). Moreover, pinosylvin has anti-oxidant capacity as well, though to a lesser extent than, for instance, resveratrol (Stojanovic et al., 2001).

Presently, pinosylvin is mostly obtained in a mixture of various flavonoids that is extracted from the bark of pine. Said extraction is a labour intensive process with a low yield. In preferred aspects, the present invention provides novel, more efficient and high-yielding production processes.

In plants, the phenylpropanoid pathway is responsible for the synthesis of a wide variety of secondary metabolic compounds, including lignins, salicylates, coumarins, hydroxycinnamic amides, pigments, flavonoids and phytoalexins. Indeed formation of stilbenes in plants proceeds through the phenylpropanoid pathway. The amino acid L-phenylalanine is converted into trans-cinnamic acid through the non-oxidative deamination by L-phenylalanine ammonia lyase (PAL) (FIG. 2). From trans-cinnamic acid the pathway can branch into a resveratrol-forming route or into a pinosylvin forming route. In the first route trans-cinnamic acid is hydroxylated at the para-position to 4-coumaric acid (4-hydroxycinnamic acid) by cinnamate-4-hydroxylase (C4H), a cytochrome P450 monooxygenase enzyme, in conjunction with NADPH: cytochrome P450 reductase (CPR). Subsequently, 4-coumaric acid, is then activated to 4-coumaroyl-CoA by the action of 4-coumarate-CoA ligase (4CL). A resveratrol synthase (VST1), can then catalyze the condensation of a phenylpropane unit of 4-coumaroyl-CoA with malonyl CoA, resulting in formation of resveratrol. In the latter route trans-cinnamic acid is directly activated to cinnamoyl-CoA by the action of 4CL where a pinosylvin synthase (PST) subsequently catalyzes the condensation of a phenylpropane unit of cinnamoyl-CoA with malonyl CoA, resulting in formation of pinosylvin.

Stilbene synthases are rather promiscuous enzymes that can accept a variety of physiological and non-physiological substrates. For instance, addition of various phenylpropanoid CoA starter esters led to formation of several products in vitro (Ikuro et al., 2004; Morita et al., 2001). Likewise it has been shown that resveratrol synthase from rhubarb (*Rheum tartari-*

*cum*) indeed synthesized a small amount of pinosylvin when cinnamoyl-CoA was used as substrate instead of coumaroyl-CoA (Samappito et al., 2003).

Similarly, coumaroyl-CoA ligase can accept both coumaric acid and cinnamic acid as substrate, albeit with a catalytic efficiency ($K_m/K_{cat}$) that is 100 times less for cinnamic acid compared to coumaric acid (Allina et al., 1998; Ehlting et al., 1999). We deduced from the above that it would be possible to produce pinsosylvin in a pathway that would consist of a 4CL and a stilbene synthase, even one that is designated as a classical resveratrol synthase.

Recently, a yeast was disclosed that could produce resveratrol from coumaric acid that is found in small quantities in grape must (Becker et al. 2003, ZA200408194). The production of 4-coumaroyl-CoA from exogenous 4-coumaric acid, and concomitant resveratrol, in laboratory strains of *S. cerevisiae*, was achieved by co-expressing a heterologous coenzyme-A ligase gene, from hybrid poplar, together with the grapevine resveratrol synthase gene (VST1). The other substrate for resveratrol synthase, malonyl-CoA, is already endogenously produced in yeast and is involved in de novo fatty-acid biosynthesis. The study showed that cells of *S. cerevisiae* could produce minute amounts of resveratrol, either in the free form or in the glucoside-bound form, when cultured in synthetic media that was supplemented with 4-coumaric acid.

Given the promiscuity of the resveratrol synthase, it may be that said yeast could produce pinosylvin as well when fed with substantial amounts of cinnamic acid. However, commercial application of such a yeast would be hampered by the probable low pinosylvin yield, and the need for addition of cinnamic acid, which is not abundantly present in industrial media. Hence, to accelerate and broaden the application of pinosylvin as both a pharmaceutical and neutraceutical, it is highly desirable to provide a yeast or other micro-organism that can produce pinosylvin directly from glucose, without addition of cinnamic acid or any downstream cinnamic acid derivative such as cinnamoyl-CoA.

A recent study (Ro and Douglas, 2004) describes the reconstitution of the entry point of the phenylpropanoid pathway in *S. cerevisiae* by introducing PAL, C4H and CPR from Poplar. The purpose was to evaluate whether multienzyme complexes (MECs) containing PAL and C4H are functionally important at this entry point into phenylpropanoid metabolism. By feeding the recombinant yeast with [3H]-phenylalanine it was found that the majority of metabolized [3H]-phenylalanine was incorporated into 4-[3H]-coumaric acid, and that phenylalanine metabolism was highly reduced by inhibiting C4H activity. Moreover, PAL-alone expressers metabolized very little phenylalanine into cinnamic acid. When feeding [3H]-phenylalanine and [14C]-trans-cinnamic acid simultaneously to the triple expressers, no evidence was found for channeling of the endogenously synthesized [3H]-trans-cinnamic acid into 4-coumaric acid. Therefore, efficient carbon flux from phenylalanine to 4-coumaric acid via reactions catalyzed by PAL and C4H does not appear to require channeling through a MEC in yeast, and sheer biochemical coupling of PAL and C4H seems to be sufficient to drive carbon flux into the phenylpropanoid pathway. In yet another study (Hwang et al., 2003) production of plant-specific flavanones by *Escherichia coli* was achieved through expression of an artificial gene cluster that contained three genes of a phenyl propanoid pathway of various heterologous origins; PAL from the yeast *Rhodotorula rubra*, 4CL from the actinomycete *Streptomyces coelicolor*, and chalcone synthase (CHS) from the licorice plant *Glycyrrhiza echinata*. These pathways bypassed C4H, because the bacterial 4CL enzyme ligated coenzyme A to both trans-cinnamic acid and 4-coumaric acid. In addition, the PAL from *Rhodotorula rubra* uses both phenylalanine and tyrosine as the substrates. Therefore, *E. coli* cells containing the gene clusters and grown on glucose, produced small amounts of two flavanones, pinocembrin (0.29 g/l) from phenylalanine and naringenin (0.17 g/l) from tyrosine. In addition, large amounts of their precursors, 4-coumaric acid and trans-cinnamic acid (0.47 and 1.23 mg/liter respectively), were accumulated. Moreover, the yields of these compounds could be increased by addition of phenylalanine and tyrosine.

Also described are studies in which the enzyme properties of pinosylvin syntheses are studied by first cloning the genes into *Escherichia coli*. For instance, Raiber et al., 1995 report on stilbenes from *Pinus strobus* (Eastern white pine) that were investigated after heterologous expression in *Escherichia coli*. For this a *P. strobus* cDNA library was screened with a stilbene synthase (STS) probe from *Pinus sylvestris* and amongst the isolated cDNAs two closely related STS genes, STS1 and STS2, were found with five amino acid differences in the proteins. The genes were cloned on a plasmid and expressed into *E. coli*, and cell extracts were subjected to enzyme assays. It appeared that both proteins accepted cinnamoyl-CoA as a substrate and thus were considered as pinosylvin syntheses, however they revealed large differences. STSI had only 3-5% of the activity of STS2, and its pH optimum was shifted to lower values (pH 6), and it synthesized with cinnamoyl-CoA a second unknown product. Site-directed mutagenesis demonstrated that a single Arg-to-His exchange in STS1 was responsible for all of the differences. In another study three STS cDNAs (PDSTS1, PDSTS2, and PDSTS3) from *Pinus densiflora* were isolated and the cDNAs were heterologously expressed in *E. coli* to characterize their enzymatic properties (Kodan et al., 2002). PDSTS3 appeared to be an unusual STS isozyme that showed the highest pinosylvin-forming activity among the STSs tested. Furthermore, PDSTS3 was insensitive to product inhibition unlike PDSTS1 and PDSTS2. The unusual characteristics of PDSTS3 could be ascribed to a lack of a C-terminal extension that normally is common to stilbene syntheses, which was caused by a frame-shift mutation. In yet another study a genomic DNA library was screened with pinosylvin synthase cDNA pSP-54 as a probe (Müller et al., 1999). After subcloning, four different members were characterized by sequencing. The amino acid sequences deduced from genes PST-1, PST-2, PST-3 and PST-5 shared an overall identity of more than 95%.

Differences in promoter strength were then analysed by transient expression in tobacco protoplasts. Constructs used contained the bacterial-glucuronidase under the control of the promoters of pine genes PST-1, PST-2 and PST-3. Upon treatment with UV light or fungal elicitor, the promoter of PST-1 showed highest responsiveness and led to tissue-specific expression in vascular bundles. The data suggest that in pine the gene product of PST-1 is responsible for both the stress response in seedlings and pinosylvin formation in the heartwood.

A further study showed that a stilbene synthase cloned from Scots pine (*Pinus sylvestris*) was earlier abortively assigned as a dihydropinosylvin synthase, while it showed to be a pinosylvin synthase. The previous mis-interpretation was caused by the influence of bacterial factors on the substrate preference and the activity of the plant-specific protein that was expressed in *E. coli*. After improvement of the expression system, the subsequent kinetic analysis revealed that cinnamoyl-CoA rather than phenylpropionyl-CoA was the preferred substrate of the cloned stilbene synthase. Furthermore, extracts from *P. sylvestris* contained factor(s) that selectively influenced the substrate preference, i.e. the activity was reduced with phenylpropionyl-CoA, but not with cinnamoyl-CoA. This explained the apparent differences between plant extracts and the cloned enzyme expressed in *E. coli* and cautions that factors in the natural and the new hosts may complicate the functional identification of cloned sequences.

Furthermore, vectors are described with stilbene synthase genes, which can mean resveratrol synthase and pinosylvin synthase, for the transformation of organisms and plants to confer enhanced resistance against pests and wounding (EP0309862 and EP0464461).

Also, further vectors are described that contain DNA sequences that will hybridise to pinosylvin synthase of *Pinus sylvestris* (U.S. Pat. No. 5,391,724) and said vectors to be used for expression in a plant (U.S. Pat. No. 5,973,230). The incorporation of PAL and 4CL together with a stilbene synthase for the production of pinosylvin in a organism is not however disclosed. Nor are any pinosylvin producing microorganisms.

Recently, evidence was shown that the filamentous fungi *A. oryzae* contained the enzyme chalcone synthase (CHS) that is normally involved in the biosynthesis of flavonoids, such as naringenin, in plants (Juvvadi et al., 2005; Seshime et al., 2005). Indeed it was also shown that *A. oryzae* contained the major set of genes responsible for phenylpropanoid-flavonoid metabolism, i.e PAL, C4H and 4CL. However, there is no evidence that *A. oryzae* contains a stilbene synthase.

Our co-pending application WO2006/089898 describes resveratrol producing micro-organisms, especially yeasts.

SUMMARY OF THE INVENTION

The present invention now provides a micro-organism having an operative metabolic pathway comprising at least one enzyme activity producing pinosylvin from cinnamic acid. In preferred micro-organisms said pathway produces cinnamic acid and produces pinosylvin therefrom. Especially, the invention provides the use of such micro-organisms in producing pinosylvin. Such a micro-organism may be naturally occurring and may be isolated by suitable screening procedures such as degenerate PCR, Southern blotting and in silico homology searches, but more preferably is genetically engineered.

The invention includes methods of producing pinosylvin from such micro-organisms, and optionally isolating or purifying pinosylvin thereby produced. The culturing is preferably conducted in the substantial absence of an external source of cinnamic acid. This implies also, the substantial absence of an external source of derivatives of cinnamic acid formed therefrom in the phenylpropanoid pathway such as cinnamoyl-CoA.

DETAILED DESCRIPTION OF PREFERRED EMBODIMENTS

Preferably, said pinosylvin or derivative is produced in a reaction catalysed by an enzyme in which endogenous malonyl-CoA is a substrate, and preferably said pinosylvin is produced from cinnamoyl-CoA.

Said pinosylvin or derivative is preferably produced from cinnamoyl-CoA, preferably by a stilbene synthase synthase which preferably is expressed in said micro-organism from nucleic acid coding for said enzyme which is not native to the micro-organism.

Generally herein, unless the context implies otherwise, references to pinosylvin include reference to oligomeric or glycosidically bound derivatives thereof.

Thus, in certain preferred embodiments, said stilbene synthase is a resveratrol synthase (EC 2.3.1.95) from a plant belonging to the genus of *Arachis*, e.g. *A. glabatra*, *A. hypogaea*, a plant belonging to the genus of *Rheum*, e.g. *R. tataricum*, a plant belonging to the genus of *Vitus*, e.g. *V. labrusca*, *V. riparaia*, *V. vinifera*, or any one of the genera *Pinus*, *Piceea*, *Lilium*, *Eucalyptus*, *Parthenocissus*, *Cissus*, *Calochortus*, *Polygonum*, *Gnetum*, *Artocarpus*, *Nothofagus*, *Phoenix*, *Festuca*, *Carex*, *Veratrum*, *Bauhinia* or *Pterolobium*.

The stilbene synthase may be one which exhibits a higher turnover rate with cinnamoyl-CoA as a substrate than it does with 4-coumaroyl-CoA as a substrate, e.g. by a factor of at least 1.5 or at least 2. Thus, in further preferred embodiments, said stilbene synthase is a pinosylvin synthase, suitably from a tree species such as a species of *Pinus*, *Eucalyptus*, *Picea* or *Maclura*. In particular, the stilbene synthase may be a pinosylvin synthase (EC 2.3.1.146) from a plant belonging to the genus of *Pinus*, e.g. *P. sylvestris*, *P. strobes*, *P. densiflora*, *P. taeda*, a plant belonging to the genus of *Picea*, or any one of the genus *Eucalyptus*.

Preferably, said cinnamic acid may be produced from L-phenylalanine in a reaction catalysed by an enzyme in which ammonia is produced and suitably said cinnamic acid is formed from L-phenylalanine by a phenylalanine ammonia lyase.

In certain preferred embodiments, said L-phenylalanine ammonia lyase is a L-phenylalanine ammonia lyase (EC 4.3.1.5) from a plant or a micro-organism. The plant may belong to the genus of *Arabidopsis*, e.g. *A. thaliana*, a plant belonging to the genus of *Brassica*, e.g. *B. napus*, *B. rapa*, a plant belonging to the genus of *Citrus*, e.g. *C. reticulate*, *C. clementinus*, *C. limon*, a plant belonging to the genus of *Phaseolus*, e.g. *P. coccineus*, *P. vulgaris*, a plant belonging to the genus of *Pinus*, e.g. *P. banksiana*, *P. monticola*, *P. pinaster*, *P. sylvestris*, *P. taeda*, a plant belonging to the genus of *Populus*, e.g. *P. balsamifera*, *P. deltoides*, *P. Canadensis*, *P. kitakamiensis*, *P. tremuloides*, a plant belonging to the genus of *Solanum*, e.g. *S. tuberosum*, a plant belonging to the genus of *Prunus*, e.g. *P. avium*, *P. persica*, a plant belonging to the genus of *Vitus*, e.g. *Vitus vinifera*, a plant belonging to the genus of *Zea*, e.g. *Z. mays* or other plant genera e.g. *Agastache*, *Ananas*, *Asparagus*, *Bromheadia*, *Bambusa*, *Beta*, *Betula*, *Cucumis*, *Camellia*, *Capsicum*, *Cassia*, *Catharanthus*, *Cicer*, *Citrullus*, *Coffea*, *Cucurbita*, *Cynodon*, *Daucus*, *Dendrobium*, *Dianthus*, *Digitalis*, *Dioscorea*, *Eucalyptus*, *Gallus*, *Ginkgo*, *Glycine*, *Hordeum*, *Helianthus*, *Ipomoea*, *Lactuca*, *Lithospermum*, *Lotus*, *Lycopersicon*, *Medicago*, *Malus*, *Manihot*, *Medicago*, *Mesembryanthemum*, *Nicotiana*, *Olea*, *Oryza*, *Pisum*, *Persea*, *Petroselinum*, *Phalaenopsis*, *Phyllostachys*, *Physcomitrella*, *Picea*, *Pyrus*, *Quercus*, *Raphanus*, *Rehmannia*, *Rubus*, *Sorghum*, *Sphenostylis*, *Stellaria*, *Stylosanthes*, *Triticum*, *Trifolium*, *Triticum*, *Vaccinium*, *Vigna*, *Zinnia*. The micro-organism might be a fungus belonging to the genus *Agaricus*, e.g. *A. bisporus*, a fungus belonging to the genus *Aspergillus*, e.g. *A. oryzae*, *A. nidulans*, *A. fumigatus*, a fungus belonging to the genus *Ustilago*, e.g. *U. maydis*, a bacterium belonging to the genus *Rhodobacter*, e.g. *R. capsulatus*, a bacterium belonging to the genus *Streptomyces*, e.g. *S. maritimus*, a bacterium belonging to the genus *Photorhabdus*, e.g. *P. luminescens*, a yeast belonging to the genus *Rhodotorula*, e.g. *R. rubra*.

Because, as described above, for the production of pinosylvin we require production of cinnamic acid by a PAL enzyme and also its conversion on to pinosylvin rather than either the production of coumaric acid from tyrosine by a substrate promiscuous PAL or by conversion of cinnamic acid by a C4H enzyme, micro-organisms for use in the invention preferably have a PAL which favours phenylalanine as a substrate (thus producing cinnamic acid) over tyrosine (from which it would produce coumaric acid). Preferably, therefore, the ratio $K_m$(phenylalanine)/$K_m$(tyrosine) for the PAL is less than 1:1, preferably less 1:5, e.g. less than 1:10. As usual, $K_m$ is the molar concentration of the substrate (phenylalanine or tyrosine respectively) that produces half the maximal rate of product formation ($V_{max}$).

The presence of C4H is not helpful to the production of pinosylvin, but need not be forbidden provided that the diversion of cinnamic acid away from pinosylvin production toward formation of resveratrol via coumaric acid is not excessive. Therefore, preferably C4H production is either absent or such that $K_{cat}$(PAL)/$K_{cat}$(C4H) is greater than 2, preferably greater than 4. As usual, in each case, $K_{cat}$ is $V_{max}$/[Enzyme], where [Enzyme] is the concentration of the relevant enzyme.

By way of illustration, typical Km values for *A. thaliana* phenylalanine ammonia lyase PAL2 and its homologue PALL are around 60 µM with phenylalanine as substrate (Cochrane et al, 2004) and more than 1000 µM when using tyrosine as substrate (Watts et al, 2006). The catalytic turnover rate $K_{cat}$ for *A. thaliana* PAL2 is 192 mol cinnamic acid/mole enzyme PAL2 when converting phenylalanine to cinnamic acid (Cochrane et al, 2004) but $K_{cat}$ is minute for the conversion of tyrosine to coumaric acid. A PAL with the above kinetic properties is specific for phenylalanine as substrate and gives exclusively cinnamic acid formation from phenylalanine and undetectable levels of coumaric acid from tyrosine.

The typical turnover rate for the hydroxylase reaction catalyzed by C4H is 25 moles coumaric acid product/mole enzyme/minute when native yeast CPR activity supports the reaction (Urban et al, 1994). The activity of C4H may be limited by NADPH availability and this may be increased if the enzyme cytochrome P450 hydroxylase (CPR) is overexpressed. If CPR is overexpressed as exemplified in the literature by 5 to 20 times (Mizutani et al, 1998, Urban et al, 1994) the catalytic turnover rates for the C4H reaction converting cinnamic acid to coumaric acid increases to 125 mole coumaric acid product/mole enzyme/minute and 530 mole coumaric acid product/mole enzyme/minute, respectively.

The outcome of the combined reaction PAL-C4H-CPR will depend on the catalytic numbers and the amount of each enzyme present, especially the amount of CPR supporting the electron donation, NADPH, for the C4H. An efficient PAL will give ca 192 moles cinnamic acid/mole PAL/minute and the C4H enzyme following in the sequence will convert ca 25 moles of this cinnamic acid/mole C4H/minute into coumaric acid with native CPR activity. Thus the dominant product from the combined reaction PAL-C4H-CPR will be cinnamic acid (167 moles cinnamic acid/mole PAL enzyme/minute and 25 moles coumaric acid/mole enzyme C4H/minute with native CPR activity. Higher CPR activity will lead to more C4H activity per mole C4H enzyme and ultimately to pure coumaric acid if overexpressed at high levels. A CPR overexpressed only five times as in the Mizutani paper (Mizutani et al, 1998) would result in 125 moles coumaric acid/mole C4H/minute and only 67 moles cinnamic acid would be the result from the PAL per minute. Thus the CPR must at least be overexpressed ca 8 times for (undesired) pure coumaric acid production.

In the case of a recombinant or natural organism with several PALs/TALs and C4H one can prepare a cell extract and measure the apparent catalytic turnover rates and Km values as a sum total (or aggregated enzyme) apparent enzyme PAL, TAL or C4H. From these estimated sum properties it will be possible to determine if the organism will produce mainly coumaric acid or cinnamic acid and thus which product resveratrol or pinosylvin would be the outcome when 4CL and VST are expressed in this organism. The turnover rate will now be expressed as moles product/(mole total protein/time) instead of when using pure enzymes moles product/(mol pure enzyme/time). Therefore, the preferred ratio $K_m$(phenylalanine)/$K_m$(tyrosine) for the PAL less than 1:1 can be applied to the aggregate PAL activity where more than one PAL is present and the preferred ratio $K_{cat}$(PAL)/$K_{cat}$(C4H) greater than 2 can be applied to the aggregate of the PAL and/or C4H activity (as modulated by CPR) where more than one PAL and/or C4H activity is present.

Preferably, the micro-organism has no exogenous C4H, i.e. has not been genetically modified to provide expression of a C4H enzyme. Any C4H production there may then be will be native to the organism. Optionally, the micro-organism without exogenous C4H may also lack endogenous C4H. Lack of endogenous C4H may be due to a native C4H capability having been deleted by genetic engineering or gene silencing methods or simply because the organism naturally lacks the C4H genes, since the enzyme is not part of its metabolism.

Also, as seen above, the presence of CPR is not helpful to the production of pinosylvin and its overexpression, while not forbidden is not generally desirable. Accordingly, the micro-organism preferably has no endogenous CPR, no exogenous CPR or has no overexpression of native CPR, or may have reduced expression of native CPR.

Suitably, said L-phenylalanine ammonia lyase is expressed in said micro-organism from nucleic acid coding for said enzyme which is not native to the micro-organism.

Preferably, cinnamoyl-CoA is formed in a reaction catalysed by an enzyme in which ATP and CoA are substrates and ADP is a product and suitably cinnamoyl-CoA is formed in a reaction catalysed by a 4-coumarate-CoA ligase (also referred to as 4-coumaroyl-CoA ligase). Known 4-coumarate-CoA ligase enzymes accept either 4-coumaric acid or cinnamic acid as substrates and produce the corresponding CoA derivatives. Generally, such enzymes are known as '4-coumarate-CoA ligase' whether they show higher activity with 4-coumaric acid as substrate or with cinnamic acid as substrate. However, we refer here to enzymes having that substrate preference as 'cinnamate-CoA ligase' enzymes (or cinnamoyl-CoA-ligase). One such enzyme is described for instance in Aneko et al., 2003.

Said 4-coumarate-CoA ligase or cinnamate-CoA ligase may be a 4-coumarate-CoA ligase/cinnamate-CoA ligase (EC 6.2.1.12) from a plant, a micro-organism or a nematode. The plant may belong to the genus of *Abies*, e.g. *A. beshanzuensis*, *B. firma*, *B. holophylla*, a plant belonging to the genus of *Arabidopsis*, e.g. *A. thaliana*, a plant belonging to the genus of *Brassica*, e.g. *B. napus*, *B. rapa*, *B. oleracea*, a plant belonging to the genus of *Citrus*, e.g. *C. sinensis*, a plant belonging to the genus of *Larix*, e.g. *L. decidua*, *L. gmelinii*, *L. griffithiana*, *L. himalaica*, *L. kaempferi*, *L. laricina*, *L. mastersiana*, *L. occidentalis*, *L. potaninii*, *L. sibirica*, *L. speciosa*, a plant belonging to the genus of *Phaseolus*, e.g. *P. acutifolius*, *P. coccineus*, a plant belonging to the genus of *Pinus*, e.g. *P. armandii P. banksiana*, *P. pinaster*, a plant belonging to the genus of *Populus*, e.g. *P. balsamifera*, *P. tomentosa*, *P. tremuloides*, a plant belonging to the genus of *Solanum*, e.g. *S. tuberosum*, a plant belonging to the genus of

*Vitus*, e.g. *Vitus vinifera*, a plant belonging to the genus of *Zea*, e.g. *Z. mays*, or other plant genera e.g. *Agastache, Amorpha, Cathaya, Cedrus, Crocus, Festuca, Glycine, Juglans, Keteleeria, Lithospermum, Lolium, Lotus, Lycopersicon, Malus, Medicago, Mesembryanthemum, Nicotiana, Nothotsuga, Oryza, Pelargonium, Petroselinum, Physcomitrella, Picea, Prunus, Pseudolarix, Pseudotsuga, Rosa, Rubus, Ryza, Saccharum, Suaeda, Thellungiella, Triticum, Tsuga*. The micro-organism might be a filamentous fungi belonging to the genus *Aspergillus*, e.g. *A. flavus, A. nidulans, A. oryzae, A. fumigatus*, a filamentous fungus belonging to the genus *Neurospora*, e.g. *N. crassa*, a fungus belonging to the genus *Yarrowia*, e.g. *Y. lipolytica*, a fungus belonging to the genus of *Mycosphaerella*, e.g. *M. graminicola*, a bacterium belonging to the genus of *Mycobacterium*, e.g. *M. bovis, M. leprae, M. tuberculosis*, a bacterium belonging to the genus of *Neisseria*, e.g. *N. meningitidis*, a bacterium belonging to the genus of *Streptomyces*, e.g. *S. coelicolor*, a bacterium belonging to the genus of *Rhodobacter*, e.g. *R. capsulatus*, a nematode belonging to the genus *Ancylostoma*, e.g. *A. ceylanicum*, a nematode belonging to the genus *Caenorhabditis*, e.g. *C. elegans*, a nematode belonging to the genus *Haemonchus*, e.g. *H. contortus*, a nematode belonging to the genus *Lumbricus*, e.g. *L. rubellus*, a nematode belonging to the genus *Meilodogyne*, e.g. *M. hapla*, a nematode belonging to the genus *Strongyloidus*, e.g. *S. rattii, S. stercoralis*, a nematode belonging to the genus *Pristionchus*, e.g. *P. pacificus*.

Whilst the micro-organism may be naturally occurring, preferably at least one copy of at least one genetic sequence encoding a respective enzyme in said metabolic pathway has been recombinantly introduced into said micro-organism.

Additionally or alternatively to introducing coding sequences coding for a said enzyme, one may provide one or more expression signals, such as promoter sequences, not natively associated with said coding sequence in said organism. Thus, optionally, at least one copy of a genetic sequence encoding a L-phenylalanine ammonia lyase is operatively linked to an expression signal not natively associated with said genetic sequence in said organism.

Expression signals include nucleotide sequences located upstream (5' non-coding sequences), within, or downstream (3' non-coding sequences) of a coding sequence, and which influence the transcription, RNA processing or stability, or translation of the associated coding sequence. Such sequences may include promoters, translation leader sequences, introns, and polyadenylation recognition sequences.

Optionally, at least one copy of a genetic sequence encoding a 4-coumarate-CoA ligase or cinnamate-CoA ligase, whether native or not, is operatively linked to an expression signal not natively associated with said genetic sequence in said organism.

Optionally, at least one copy of a genetic sequence encoding a stilbene synthase, which may be a resveratrol synthase, whether native or not, is operatively linked to an expression signal not natively associated with said genetic sequence in said organism.

Optionally, at least one copy of a genetic sequence encoding a pinosylvin synthase, whether native or not, is operatively linked to an expression signal not natively associated with said genetic sequence in said organism.

In certain aspects the invention provides a metabolically engineered micro-organism of the kind described, having an operative metabolic pathway in which a first metabolite is transformed into a second metabolite in a reaction catalysed by a first enzyme, said reaction step producing ammonia, and in which said second metabolite is transformed into a third metabolite in a reaction catalysed by a second enzyme in which ATP and CoA is a substrate, and ADP is a product, and in which said third metabolite is transformed into a fourth metabolite in a reaction catalysed by a third enzyme in which endogenous malonyl-CoA is a substrate.

The micro-organisms described above include ones containing one or more copies of a heterologous DNA sequence encoding phenylalanine ammonia lyase operatively associated with an expression signal, and containing one or more copies of a heterologous DNA sequence encoding 4-coumarate-CoA-ligase or cinnamate-CoA ligase operatively associated with an expression signal, and containing one or more copies of a heterologous DNA sequence encoding a stilbene synthase, which may be resveratrol synthase, operatively associated with an expression signal.

Alternatively, the micro-organisms described above include ones containing one or more copies of a heterologous DNA sequence encoding phenylalanine ammonia lyase operatively associated with an expression signal, and containing one or more copies of a heterologous DNA sequence encoding 4-coumarate-CoA-ligase or cinnamate-CoA ligase operatively associated with an expression signal, and containing one or more copies of a heterologous DNA sequence encoding pinosylvin synthase operatively associated with an expression signal.

In the present context the term "micro-organism" relates to microscopic organisms, including bacteria, microscopic fungi, including yeast.

More specifically, the micro-organism may be a fungus, and more specifically a filamentous fungus belonging to the genus of *Aspergillus*, e.g. *A. niger, A. awamori, A. oryzae, A. nidulans*, a yeast belonging to the genus of *Saccharomyces*, e.g. *S. cerevisiae, S. kluyveri, S. bayanus, S. exiguus, S. sevazzi, S. uvarum*, a yeast belonging to the genus *Kluyveromyces*, e.g. *K. lactis K. marxianus* var. *marxianus, K. thermotolerans*, a yeast belonging to the genus *Candida*, e.g. *C. utilis C. tropicalis, C. albicans, C. lipolytica, C. versatilis*, a yeast belonging to the genus *Pichia*, e.g. *P. stipidis, P. pastoris, P. sorbitophila*, or other yeast genera, e.g. *Cryptococcus, Debaromryces, Hansenula, Pichia, Yarrowia, Zygosaccharomryces* or *Schizosaccharomryces*. Concerning other micro-organisms a non-exhaustive list of suitable filamentous fungi is supplied: a species belonging to the genus *Penicillium, Rhizopus, Fusariurn, Fusidium, Gibberella, Mucor, Mortierella, Trichoderma*.

Concerning bacteria a non-exhaustive list of suitable bacteria is given as follows: a species belonging to the genus *Bacillus*, a species belonging to the genus *Escherichia*, a species belonging to the genus *Lactobacillus*, a species belonging to the genus *Lactococcus*, a species belonging to the genus *Corynebacterium*, a species belonging to the genus *Acetobacter*, a species belonging to the genus *Acinetobacter*, a species belonging to the genus *Pseudomonas*, etc.

The preferred micro-organisms of the invention may be *S. cerevisiae, A. niger, A. oryzae, E. coli, L. lactis* or *B. subtilis*.

The constructed and engineered micro-organism can be cultivated using commonly known processes, including chemostat, batch, fed-batch cultivations, etc.

Thus, the invention includes a method for producing pinosylvin comprising contacting a micro-organism cell with a carbon substrate in the substantial absence of an external source of cinnamic acid, said cell having the capacity to produce pinosylvin under the conditions, in which the micro-organism may be selected from the group consisting of fungi and bacteria, especially yeast.

Pinosylvin so produced may optionally be isolated or purified and suitable methods include solvent extraction with n-hexane, followed by sequential extraction with 100% ether, acetone, methanol and water, and chromatographic purification on a silicagel column using a n-hexane/ethyl acetate (2/1) system (Suga et al. 1993).

Said carbon substrate is optionally selected from the group of fermentable carbon substrates consisting of monosaccharides, oligosaccharides and polysaccharides, e.g. glucose, fructose, galactose, xylose, arabinose, mannose, sucrose, lactose, erythrose, threose, and/or ribose. Said carbon substrate may additionally or alternatively be selected from the group of non-fermentable carbon substrates including ethanol, acetate, glycerol, and/or lactate. Said non-fermentable carbon substrate may additionally or alternatively be selected from the group of amino acids and may be phenylalanine.

In an alternative aspect, the invention includes a method for producing pinosylvin through heterologous expression of nucleotide sequences encoding phenylalanine ammonia lyase, 4-coumarate-CoA ligase and resveratrol synthase and also a method for producing pinosylvin through heterologous expression of nucleotide sequences encoding phenylalanine ammonia lyase, 4-coumarate-CoA ligase and pinosylvin synthase.

Pinosylvin, including pinosylvin so produced, may be used as a nutraceutical in a food product, e.g. a dairy product or a beverage such as beer or wine. Accordingly, the invention includes a food product containing microbially produced pinosylvin.

The invention further includes a micro-organism composition comprising micro-organism cells and at least 1.5 mg/g pinosylvin on a dry weight basis. For instance, yeast or yeast containing or yeast derived preparations containing pinosylvin, or pinosylvin so produced, may be provided for human or animal consumption, e.g. in dry form, suitably as unit oral dosage forms such as yeast containing tablets or capsules, which may contain for instance at least 0.5 g of said yeast, e.g. 1-3 g.

Any wild type enzyme referred to herein may be substituted by a mutant form thereof, suitably having an amino acid homology relative to the named wild type enzyme of at least 50%, more preferably at least 60%, more preferably at least 70%, more preferably at least 80%, more preferably still at least 90% or at least 95%, whilst of course maintaining the required enzyme activity of the wild type. This may include maintaining any substrate preference of the wild type, e.g. for phenylalanine over tyrosine or for cinnamic acid over coumaric acid or for cinnamoyl-CoA over coumaroyl-CoA. Any wild type coding sequence coding for an enzyme referred to herein may be substituted with a sequence coding for the same enzyme but in which the codon usage is adjusted. This applies both to wild type enzymes mentioned herein and mutant forms as discussed above. Nucleotide sequences coding for mutant forms of wild type enzymes are preferably homologous with the wild type nucleotide sequence of the corresponding wild type enzyme to the extent of at least 50%, more preferably at least 60%, more preferably at least 70%, more preferably at least 80%, more preferably still at least 90% or at least 95%.

Mutant forms of enzymes may have a level of enzyme activity largely unchanged from that of the wild type enzyme or may be selected to have a higher level of activity. Conservative substitutions of amino acids of the wild type enzyme may be made in accordance with known practice. Enzymes having improved activity may be developed by directed evolution techniques as known in the art, random changes in the enzyme being produced by methods such as introducing random genetic changes in the coding for the enzyme in a suitable test organism such as E. coli or S. cerevisiae followed by expression and selection of improved mutants by screening for the desired property, or by imposing self selection conditions under which organisms expressing an improved activity will have a survival advantage.

References herein to the absence or substantial absence or lack of supply of a substance, e.g. of cinnamic acid, include the substantial absence of derivatives thereof such as cinnamic acid esters (including thioesters), e.g. cinnamoyl-CoA, which may be metabolised to the substance or which are immediate products of further metabolism of the substance. In particular, lack of cinnamic acid implies lack of cinnamoyl-CoA.

Pinosylvin produced according to the invention may be cis-pinosylvin or trans-pinosylvin, which are expected to be formed from cis-cinnamic acid and trans-cinnamic acid respectively. Alternatively, cis-pinosylvin may be formed from trans-cinnamic acid by a process including isomerisation. But it is to be expected that the trans-form will normally predominate.

BRIEF DESCRIPTION OF THE DRAWINGS

To assist in the ready understanding of the above description of the invention reference has been made to the accompanying drawings in which.

Figure 1:
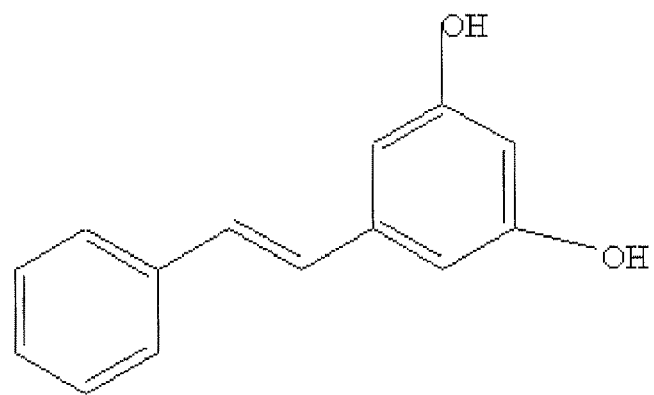
FIG. 1 shows the chemical structure of pinosylvin.
Figure 2:
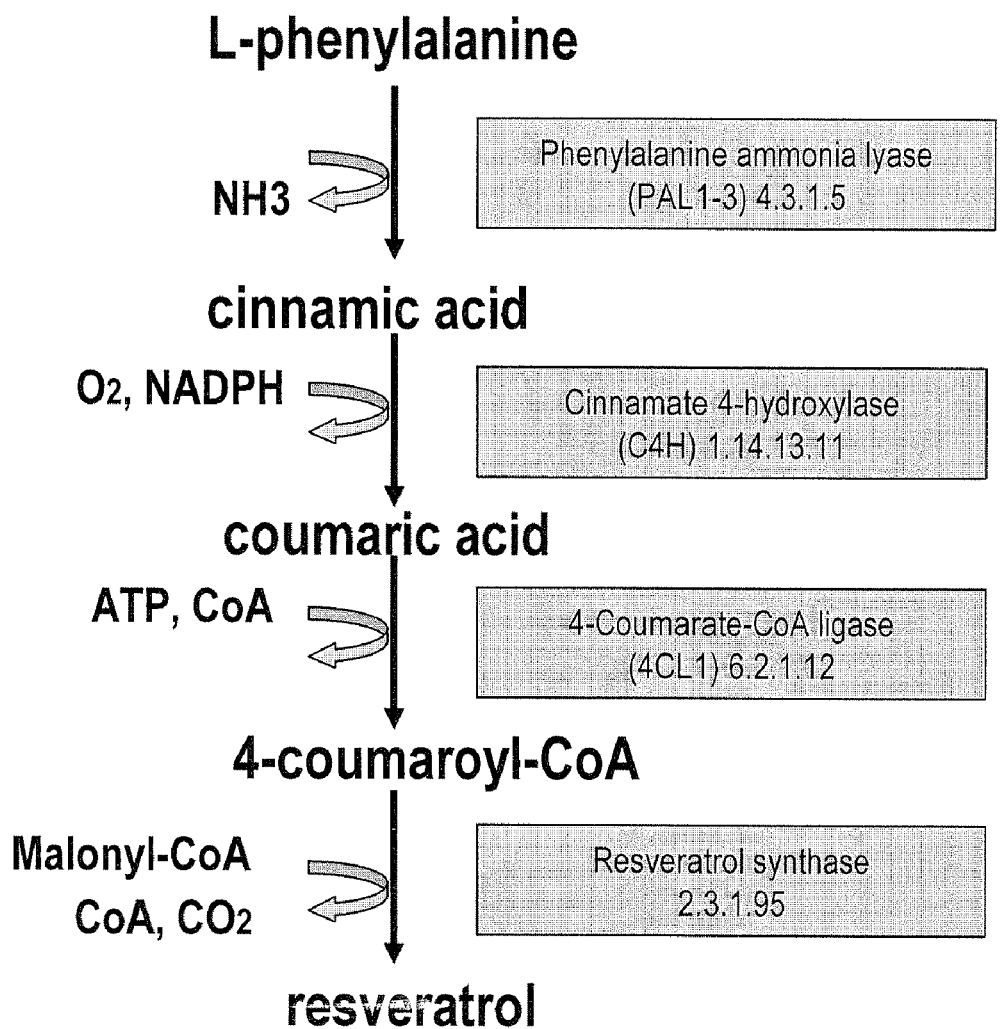
FIG. 2 shows the phenylpropanoid pathway utilising resveratrol synthase acting on coumaroyl-CoA, leading to resveratrol.
Figure 3:
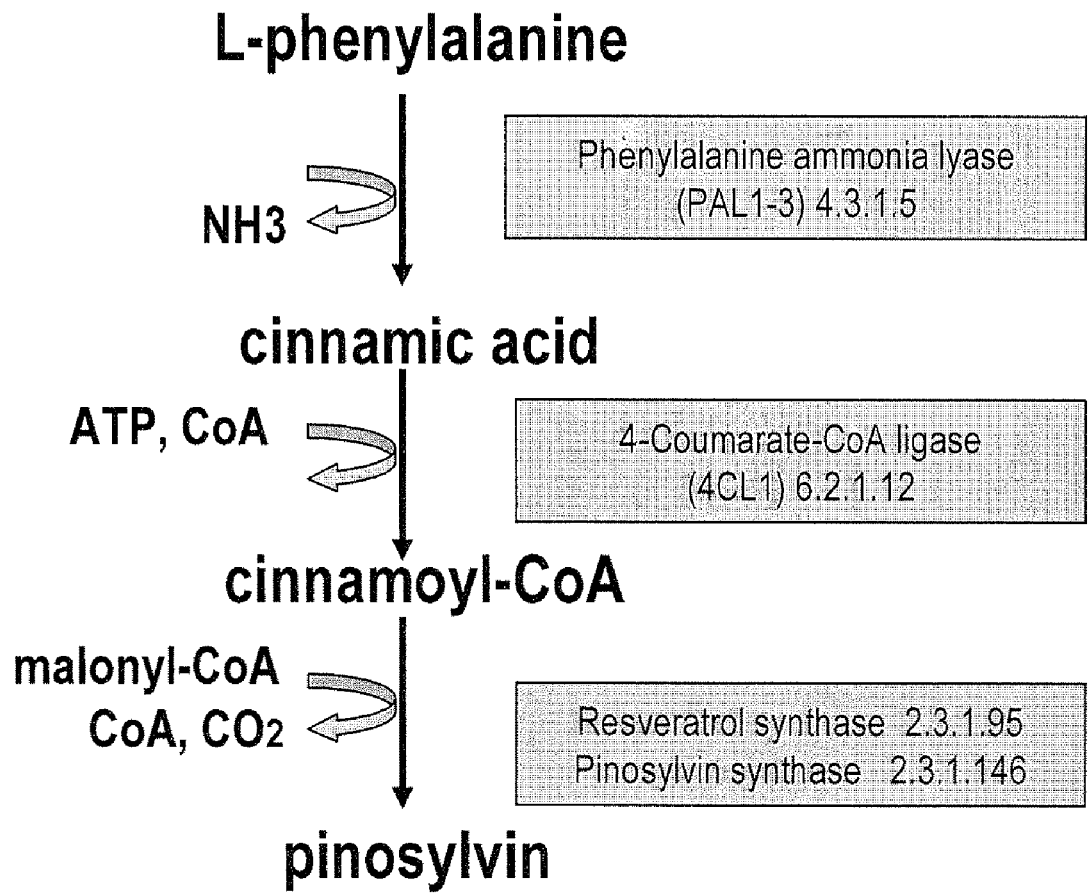
FIG. 3 shows the phenylpropanoid pathway utilising pinosylvin synthase or resveratrol synthase acting on cinnamoyl-CoA, leading to pinosylvin.

The invention will be further described and illustrated by the following non-limiting examples.

EXAMPLES

Example 1

Isolation of Genes Encoding PAL, 4CL, RES and VST1

Phenylalanine ammonia lyase (PAL2) (Cochrane et al., 2004; SEQ ID NO: 1, 2), 4-coumarate:CoenzymeA ligase (4CL1) (Hamberger and Hahlbrock 2004; Ehlting et al., 1999; SEQ ID NO: 3, 4) were isolated via PCR from A. thaliana cDNA (BioCat, Heidelberg, Germany) using the primers in table 1. PAL2 and 4CL1 were chosen amongst several A. thaliana homologues due to favourable kinetic parameters towards cinnamic acid and cinnamoyl-CoA, respectively (Cochrane et al., 2004; Hamberger and Hahlbrock 2004; Ehlting et al., 1999).

The coding sequence of resveratrol synthase (RES) from Rhubarb, *Rheum tataricum* (Samappito et al., 2003; SEQ ID NO: 5, 6) was codon optimized for expression in *S. cerevisiae* using the online service backtranslation tool at www.entelechon.com, yielding sequence SEQ ID NO: 7, 8. Oligos for the synthetic gene assembly were constructed at MWG Biotech and the synthetic gene was assembled by PCR using a slightly modified method protocol of from Martin et al. (2003) described below.

TABLE 1

Primers and restriction sites for the amplification of genes

| Primer for amplification of gene* (Restriction sites are underlined) | Gene | Restriction site: primer | Restriction site: vector |
|---|---|---|---|
| 5'-CGGAATTCTCATGGATCAAATCGAAGCAATGTT | PAL2 | EcoR1 | EcoR1 |
| 5'-CGACTAGTTTAGCAAATCGGAATCGGAGC | PAL2 | Spe1 | Spe1 |
| 5'-GCTCTAGACCT ATGGCGCCACAAGAACAAGCAGTTT | 4CL1 | Xba1 | Spe1 |
| 5'-GCGGATCCCCT TCACAATCCATTTGCTAGTTT TGCC | 4CL1 | BamH1 | BglII |
| 5'-CC GGATCCAAATGGCCCCAGAAGAGAGCAGG | RES | BamH1 | BamH1 |
| 5'-CG CTCGAGTTAAGTGATCAATGGAACCGAAGACAG | RES | Xho1 | Xho1 |

*SEQ ID Nos 11-16

Primers from MWG for the assembly of the synthetic gene were dissolved in MILLI-Q® reagent grade water to a concentration of 100 pmole/μl. An aliquot of 5 μl of each primer was combined in a totalmix and then diluted 10-fold with MILLI-Q® reagent grade water. The gene was assembled via PCR using 5 μl diluted totalmix per 50 μl as template for fusion DNA polymerase (Finnzymes). The PCR programme was as follows: Initial 98° C. for 30 s., and then 30 cycles with 98° C. for 10 s., 40° C. for 1 min, and 72° C. at 1 min./1000 basepairs, and a final 72° C. for 5 min. From the resulting PCR reaction, 20 μl was purified on 1 agarose gel. The result was a PCR smear and the regions around the wanted size were cut out from agarose gel and purified using the QiaQuick Gel Extraction Kit (Qiagen). A final PCR with the outer primers in table 1 rendered the required RES gene. Point mutations were corrected using the Quickchange site directed mutagenesis II kit (Stratagene, La Jolla, Calif.).

The VST1 gene encoding *Vitis vinifera* (grapevine) resveratrol synthase (Hain et al., 1993) was synthesized by GenScript Corporation (Piscataway, N.J.). The amino acid sequence (SEQ ID NO: 10) was used as template to generate a synthetic gene codon optimized for expression in *S. cerevisiae* (SEQ ID NO: 9). The synthetic VST1 gene was delivered inserted in *E. coli* pUC57 vector flanked by BamH1 and Xho1 restriction sites. The synthetic gene was purified from the pUC57 vector by BamH1/Xho1 restriction and purified from agarose gel using the QiaQuick Gel Extraction Kit (Qiagen).

Example 2

Construction of a Yeast Vector for Expression of PAL2

The gene encoding PAL2, isolated as described in example 1, was reamplified by PCR using forward- and reverse primers, with 5' overhangs containing EcoR1 and Spe1 restriction sites (table 1). The amplified PAL2 PCR product was digested with EcoR1/Spe1 and ligated into EcoR1/Spe1 digested pESC-URA vector (Stratagene), resulting in vector pESC-URA-PAL2. The sequence of the gene was verified by sequencing of two different clones.

Example 3

Construction of a Yeast Vector for Expression of 4CL1

The gene encoding 4CL1 was isolated as described in example 1. The amplified 4CL1 PCR-product was digested with Xba1/BamH1 and ligated into Spe1/BglII digested pESC-TRP vector (Stratagene), resulting in vector pESC-TRP-4CL1. Two different clones of pESC-TRP-4CL1 were sequenced to verify the sequence of the cloned gene.

Example 4

Construction of a Yeast Vector for Expression of 4CL1 and RES

The gene encoding RES was isolated as described in example 1. The amplified synthetic RES gene was digested with BamH1/Xho1 and ligated into BamH1/Xho1 digested pESC-TRP-4CL1 (example 3). The resulting plasmid, pESC-TRP-4CL1-RES, contained the genes encoding 4CL1 and RES under the control of the divergent GAL1/GAL10 promoter. The sequence of the gene encoding VST1 was verified by sequencing of two different clones of pESC-TRP-4CL1-VST1.

Example 5

Construction of a Yeast Vector for Expression of 4CL1 and VST1

The gene encoding VST1 was isolated as described in example 1. The purified and digested VST1 gene was ligated into BamH1/Xho1 digested pESC-TRP-4CL1 (example 3). The resulting plasmid, pESC-TRP-4CL1-VST1, contained the genes encoding 4CL1 and VST1 under the control of the divergent GAL1/GAL10 promoter. The sequence of the gene encoding VST1 was verified by sequencing of two different clones of pESC-TRP-4CL1-VST1.

Example 6

Expression of the Pathway to Pinosylvin in the Yeast *S. cerevisiae* Using PAL2, 4CL1 and RES Yeast strains containing the appropriate genetic markers were transformed with the vectors described in examples 2, 3 and 4, separately or in combination. The transformation of the yeast cell was conducted in accordance with methods known in the art by using competent cells, an alternative being for instance, electroporation (see, e.g., Sambrook et al., 1989). Transformants were selected on medium lacking uracil and/or tryptophan and streak purified on the same medium.

*S. cerevisiae* strain FS01267 (MATa trp1 ura3) was co-transformed with pESC-URA-PAL2 (example 2) and pESC-TRP-4CL1-RES (example 4), and the transformed strain was named FSSC-PAL24CL1RES.

Example 7

Expression of the Pathway to Pinosylvin in the Yeast *S. cerevisiae* Using PAL2, 4CL1 and VST1

Yeast strains containing the appropriate genetic markers were transformed with the vectors described in examples 2, 3 and 5, separately or in combination. The transformation of the yeast cell was conducted in accordance with methods known in the art, for instance, by using competent cells or by electroporation (see, e.g., Sambrook et al., 1989). Transformants were selected on medium lacking uracil and/or tryptophan and streak purified on the same medium.

*S. cerevisiae* strain FS01267 (MATa trp1 ura3) was co-transformed with pESC-URA-PAL2 (example 2) and pESC-TRP-4CL1-VST1 (example 5), and the transformed strain was named FSSC-PAL24CL1VST1.

Example 8

Fermentation with Recombinant Yeast Strains in Shake Flasks

The recombinant yeast strains were inoculated from agar plates with a sterile inoculation loop and grown in 100 ml defined mineral medium (Verduyn et al., 1992) that contained vitamins, trace elements, 5 g/l glucose 95 g/l galactose. The 500 ml stoppered shake flasks were incubated for three days at 30° C. and 160 rpm.

Example 9 a) Extraction of Pinosylvin

Cells were harvested by centrifugation 5000 g for 5 minutes. An aliquot of 50 ml of supernatant was extracted once with 20 ml ethyl acetate. The ethyl acetate was freeze dried and the dry product redissolved in 0.7 ml methanol and filtered into HPLC vials.

The cell pellet from 100 ml medium was dissolved in 2 ml water and divided into 3 fastprep tubes and broken with glass beads. The crude extracts from the three tubes were pooled into 10 ml 100% methanol in a 50 ml sartorius tube and extracted on a rotary chamber for 48 hours in a dark cold room at 4° C. After 48 hours the cell debris was removed via centrifugation for 5 min. at 5000 g and the methanol was removed by freeze-drying overnight. The dry residue was redissolved in 0.7 ml methanol and filtered into HPLC vials.

b) Analysis of Pinosylvin

HPLC

For quantitative analysis fo cinnamic acid, coumaric acid, and pinosylvin, samples were subjected to separation by high-performance liquid chromatography (HPLC) Agilent Series 1100 system (Hewlett Packard) prior to uv-diode-array detection at $\lambda=306$ nm. A Phenomenex (Torrance, Calif., USA) Luna 3 micrometer C18 (100×2.00 mm) column was used at 40° C. As mobile phase a gradient of acetonitrile and MILLI-Q® reagent grade water (both containing 50 ppm trifluoroacetic acid) was used at a flow of 0.4 ml/min. The gradient profile was linear from 15% acetonitrile to 100% acetonitrile over 20 min. The elution time was approximately 8.8-8.9 minutes for trans-pinosylvin. Pure pinosylvin standard (>95% pure) was purchased from ArboNova (Turku, Finland).

LC-MS

Samples and standards were analyzed by negative electrospray LC-MS on a Waters (Micromass, Manchester, UK) LCT™ time-of-fight mass spectrometer with a LOCK-SPRPY™ reference probe coupled to an Agilent 1100 HPLC system (Agilent Tecchnologies Walbron, Germany). The separations were done on a 50 mm×2 mm ID Luna C-18 (II) column (Phenomenex, USA) fitted with a 4 mm×2 mm ID SecurityGuard™ pre-column (Phenomenex, USA) using a water-acetonitrile gradient at 0.3 ml/minute. Both eluents contained 20 mM formic acid. The solvent composition was changed from 15%; acetonitrile at injection to 100% acetonitrile in 20 minutes, which was maintained for 5 minutes before the gradient was returned to starting conditions. A 3 µl sample was injected in all cases and the column was maintained at 40° C. All chemicals were of HPLC grade and dissolved into MILLI-Q® reagent grade water.

UV spectra were collected from 200-700 nm at 2 spectra per second with a resolution of 4 nm.

The mass spectrometer was tuned for maximum sensitivity in negative electrospray mode to a resolution better than 5500 FWH on a solution of leucine enkphaline (0.5 µg/ml in 50% acetonitril with 0.5% formic acid). Said solution was also used as mass reference in the LOCKSPPAY™ reference probe in negative ESI at 15 µl/minute. The instrument was calibrated in negative ESI on a carboxylated-PEG mixture in 50% acetonitril. In both cases the calibration had a residual error less than 2 mDa on at least 25 calibration ions. The run conditions were selected for minimal in-source fragmentation.

Mass spectra were collected from 100 to 900 Da/e at a rate of 0.4 seconds per spectrum with 0.1 second interscan time. A reference spectrum was collected from the Lockmass™ probe every 3rd seconds and 10 reference spectra were averaged for internal mass correction.

Narrow ion traces were extracted using +/−25 mDa around the protonated or deprotonated mass of the expected metabolites.

Results

Figure 4:
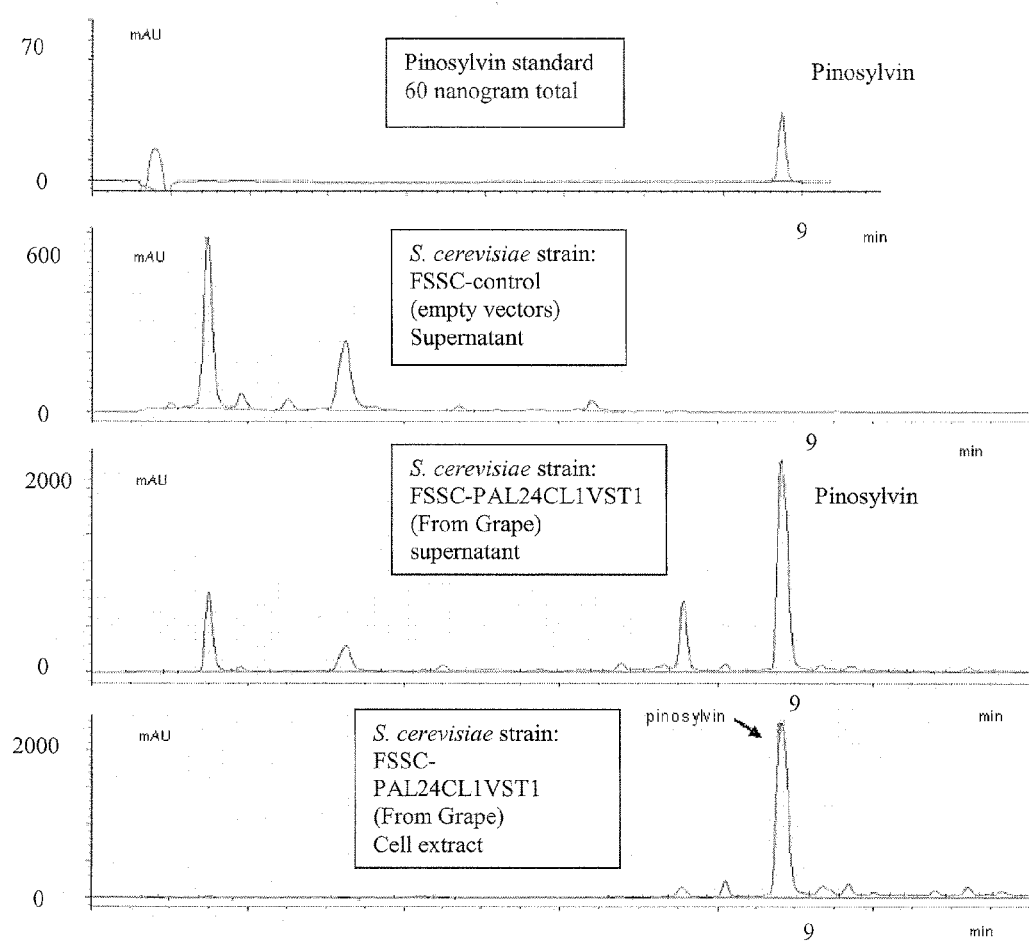
FIG. 4 shows the HPLC-chromatograms of supernatant and cell extract of S. cerevisiae strains FSSC-PAL4CLVST1, grown on 100 g/l galactose. A chromatogram of 60 nanogram of pure pinosylvin is included.
Figure 5:
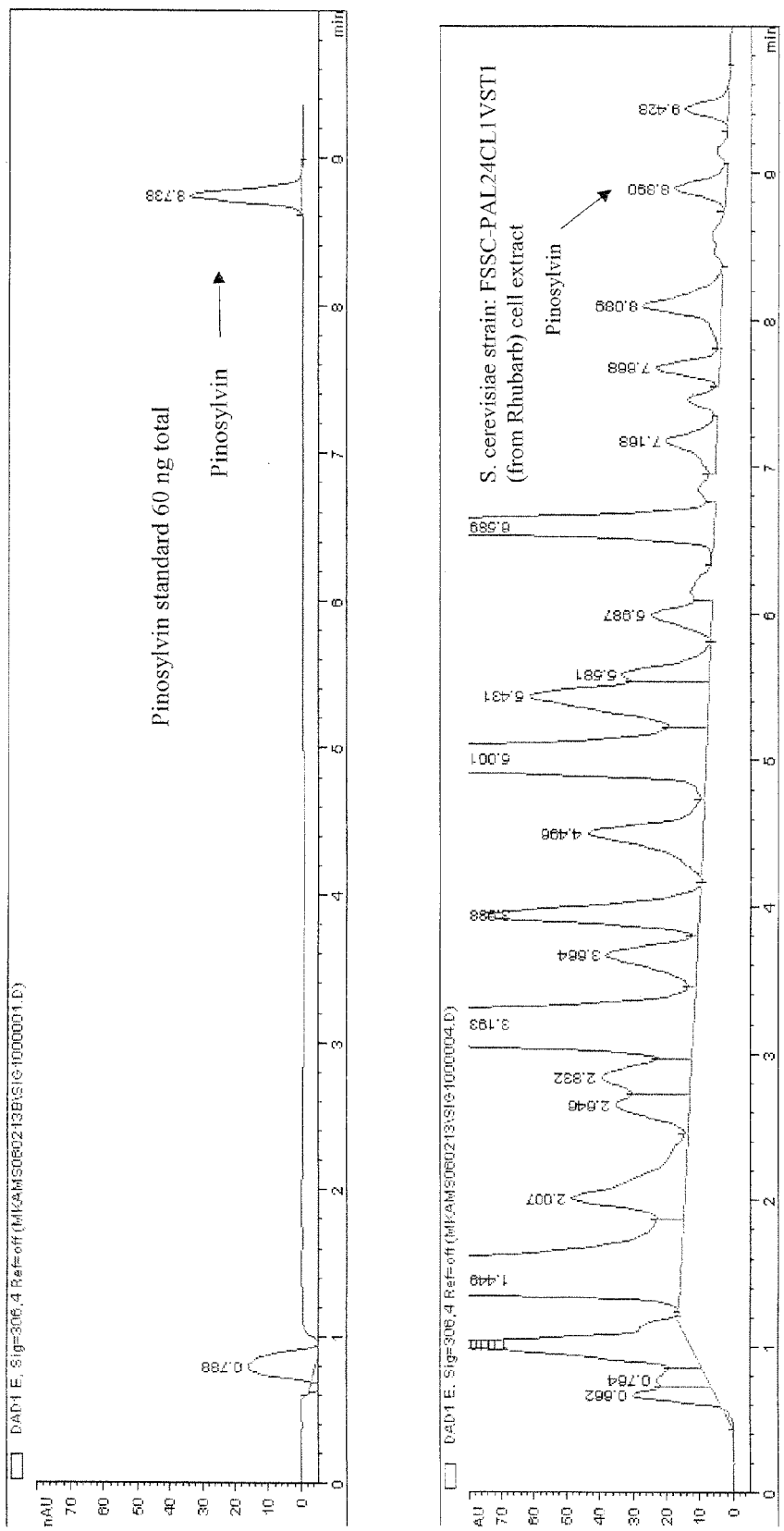
FIG. 5 shows the HPLC-chromatograms of a cell extract of S. cerevisiae strain FSSC-PAL4CLRES, grown on 100 g/l galactose. A chromatogram of 60 nanogram of pure pinosylvin is included.
Figure 6A:
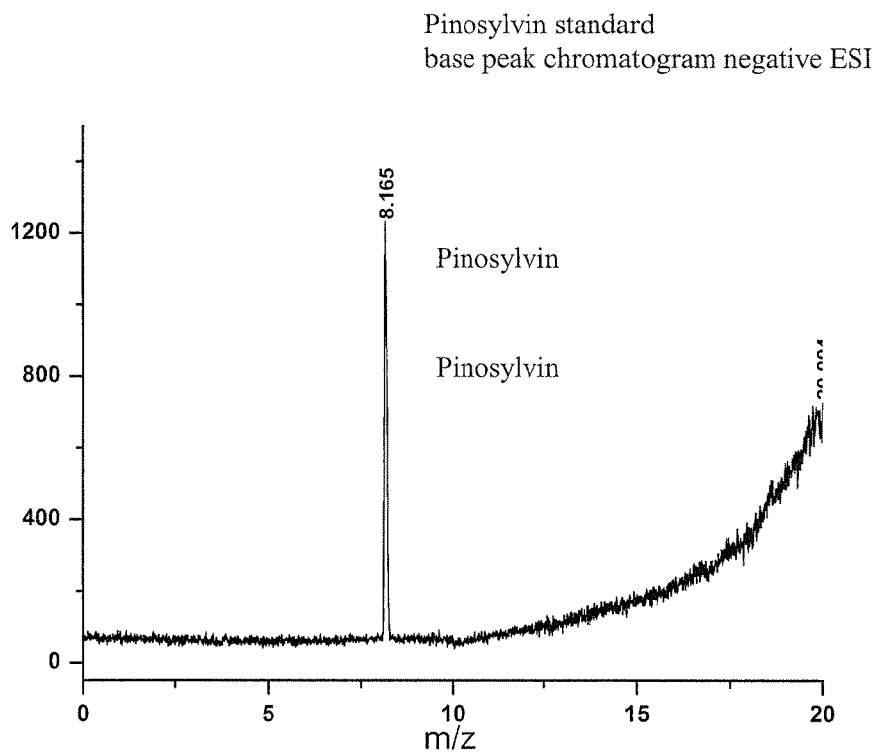
FIG. 6 shows the LC-MS data for pure pinosylvin and pinosylvin produced by S. cerevisiae strain FSSC-PAL4CLVST1, grown on 100 g/l galactose. Both base peak chromatograms, and negative ion-traces at M/Z 211.0759 Da/e are shown.
Figure 6B:
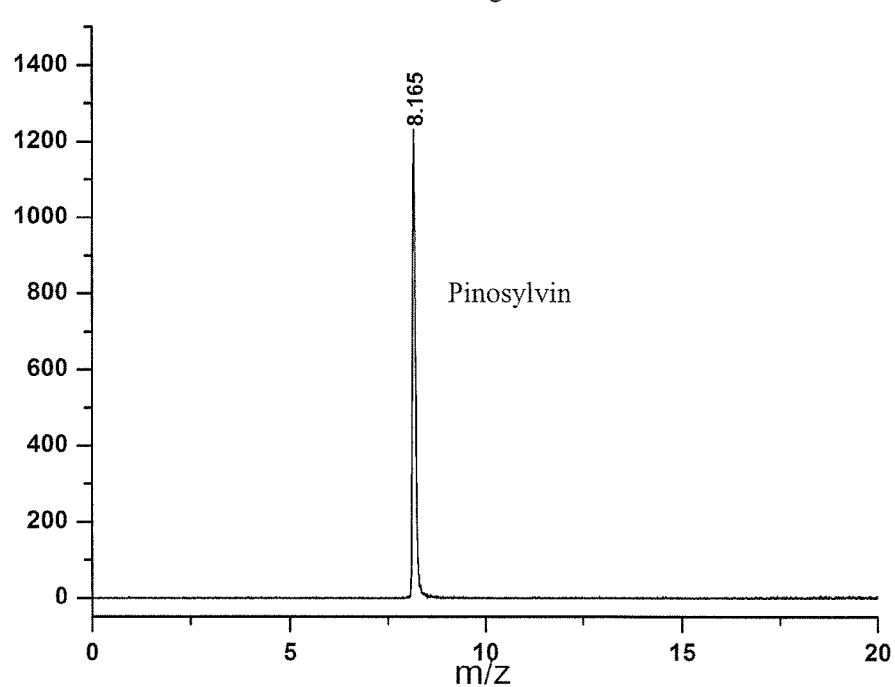
Figure 6C:
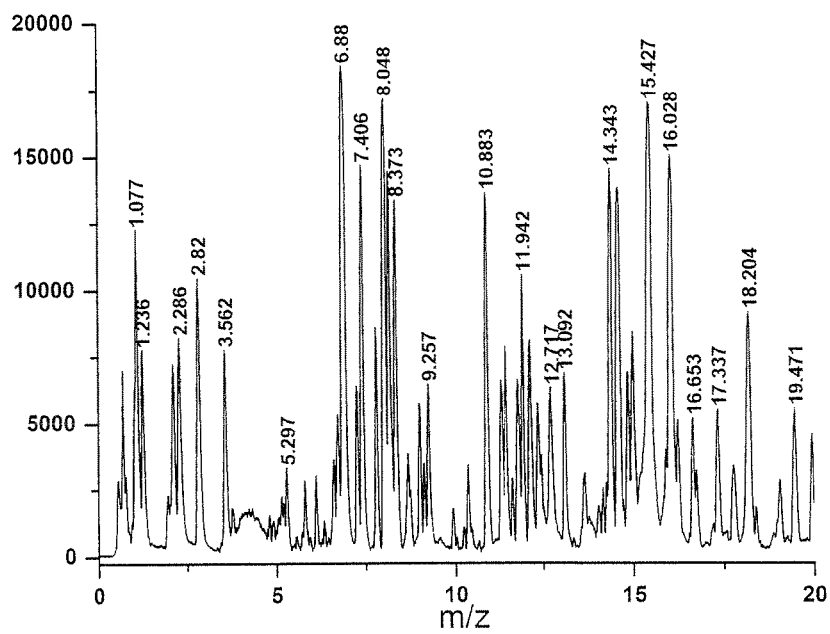
Figure 6D:
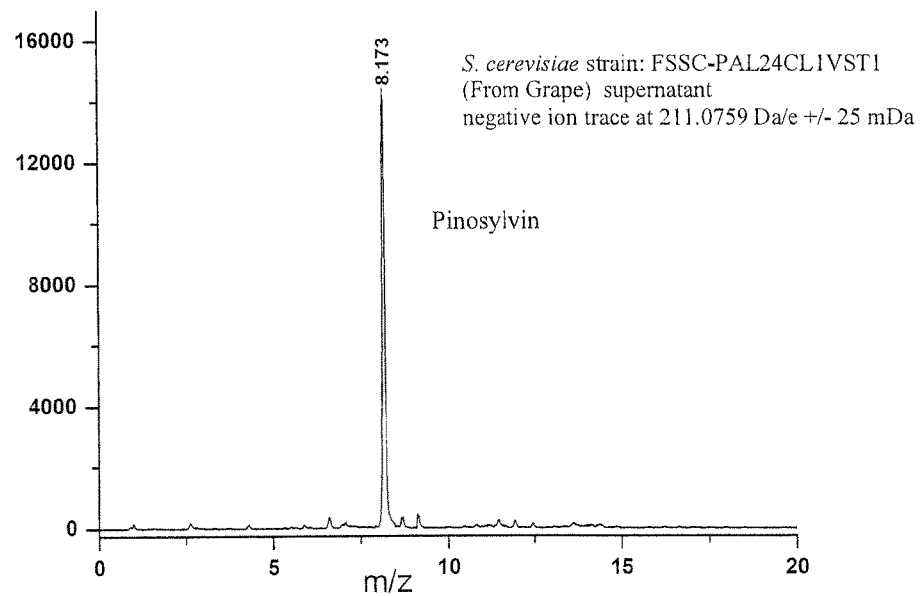

Strains FSSC-PAL24CL1RES and FSSC-PAL24CL1VST1, were cultivated on 100 g/l galactose as described in example 8, and analyzed for their content of pinosylvin. Additionally, a control strain FSSC-control was included that contained the empty vectors only. The HPLC-analysis showed that strains FSSC-PAL24CL1VST1 and FSSC-PAL24CL1RES contained a component with a retention time of 8.8-9.0 min. that was identical to trans-pinosylvin (FIGS. 4 and 5). Said result was confirmed by LC-MS analysis that revealed the presence of a component in the supernatant of strain FSSC-PAL24CL1VST1 with a retention time of 8.2 min., which had a M/Z of 211.0579 Da/e±25 mDA that indeed corresponded to the M/Z of pure pinosylvin in negative ion mode (FIG. 6). In addition the UV absorption spectra were similar to the absorption spectrum of pure trans-pinosylvin (not shown) as well, with a $\lambda_{max}$ of approximately 306 nm.

The results, therefore, demonstrated the presence of an active phenyl-propanoid pathway in *S. cerevisiae* that led to in vivo production of trans-pinosylvin. The production of pinosylvin can most likely be improved by cultivating the strains under well-defined growth conditions in batch- and continuous cultures, and/or optimizing the expression/activities of the individual enzymes

Example 10 a) Construction of a Bacterial Vector for Expression of PAL2 in *Escherichia coli*

The plasmids that were used in the following examples contained one or more marker genes to allow the microorganism that harbour them to be selected from those which do not. The selection system is based upon dominant markers, e.g. resistance against ampicilin and kanamycin. In addition, the plasmids contained promoter- and terminator sequences that allowed the expression of the recombinant genes. Furthermore, the plasmids contained suitable unique restriction sites to facilitate the cloning of DNA fragments and subsequent identification of recombinants. In this example the plasmids contained either the ampicilin resistance gene, designated as pET16b (Novagen), or the kanamycin resistance gene, designated as pET26b (Novagen).

The gene encoding PAL2, isolated as described in example 1, was reamplified by PCR from the plasmid pESC-URA-PAL2 (example 2), using forward- and reverse primers, with 5' overhangs containing suitable restriction sites. The introduction of said restriction sites at the 5' and 3' ends of the gene allowed ligation of the restricted PCR product into a digested pET16B vector that contained the T7 promoter. The resulting plasmid, pET16B-PAL2, contained the gene encoding PAL2 under the control of the T7 promoter.

b) Construction of a Bacterial Vector for Expression of 4CL1 and VST1 in *Escherichia coli*

The gene encoding 4CL1, isolated as described in example 1, was reamplified by PCR from the plasmid pESC-URA-4CL1-VST1 (example 5), using forward- and reverse primers, with 5' overhangs containing suitable restriction sites. The introduction of said restriction sites at the 5' and 3' ends of the gene allowed ligation of the restricted PCR product into a digested pET26B vector. The resulting plasmid, pET26B-4CL1, contained the gene encoding for 4CL1 under the control of the T7 promoter from *Lactobacillus lactis*.

The gene encoding VST1, isolated as described in example 1, was reamplified by PCR from the plasmid pESC-URA-4CL1-VST1 (example 5) using forward- and reverse primers, with 5' overhangs containing suitable restriction sites. The introduction of said restriction sites at the 5' and 3' ends of the gene allowed ligation of the restricted PCR product into a digested pET16B vector. The resulting plasmid, pET16B-VST1, contained the gene encoding VST1 under the control of the T7 promoter. The T7 promoter and the gene encoding VST1 were reamplified as one fragment by PCR from the plasmid pET16B-VST1 using forward and reverse primers, with 5' overhangs containing suitable restriction sites. The introduction of said restriction sites at the 5' and 3' ends of the DNA fragment allowed ligation of the restricted PCR product into the digested plasmid pET26B-4CL1. The resulting plasmid, pET26B-4CL1-VST1, contained the genes encoding 4CL1 and VST1, each under the control of their individual T7 promoter. The sequence of the genes encoding 4CL1 and VST1 was verified by sequencing of two different clones of pET26B-4CL1-VST1.

c) Expression of the Pathway to Pinosylvin in *Escherichia coli*

*Escherichia coli* strains were transformed with the vectors described in (a) and (b), separately or in combination. The transformation of the bacterial cell was conducted in accordance with methods known in the art by using competent cells, an alternative being for instance, electroporation (see, e.g., Sambrook et al., 1989). Transformants were selected on medium containing the antibiotics ampicilin and kanamycin and streak purified on the same medium.

*Escherichia coli* strain BL21 (DE3) was transformed separately with the vector pET16B-PAL2 (a), yielding the strain FSEC-PAL2; and with pET26B-4CL1-VST1 (b), yielding strain FSEC-4CL1VST1. In addition, *Escherichia coli* strain BL21 (DE3) was co-transformed with pET16B-PAL2 (a) and pET26B-4CL1-VST1 (n), and the transformed strain was named FSEC-PAL24CL1VST1.

d) Fermentation with Recombinant *Escherichia coli* Strains in Fermentors

The recombinant yeast strains can be grown in fermentors operated as batch, fed-batch or chemostat cultures. In this instance fermentation was in shake flasks.

Pre-cultures of *Escherichia coli* BL21 (DE3) were grown in glass tubes at 160 rpm and 37° C. in 7 ml of LB medium containing 100 µg/ml ampicillin and 60 µg/ml kanamycin. Exponentially growing precultures were used for inoculation of 500 ml baffled shake flasks that contains 200 ml LB medium supplemented with 50 g/l glucose, 5 g/l $K_2HPO_4$, 80 µg/ml ampicilin and 50 µg/ml kanamycin, which are incubated at 160 rpm and 37° C. After 5 hours, isopropyl β-thiogalactopyranoside (IPTG) was added at a final concentration of 1 mM, as an inducer of the T7 promoter that is in front of each of the three genes PAL2, 4CL1 and VST1. After an incubation period of 48 hours at 37° C., the cells were harvested and subjected to extraction procedures and analysed for the presence of produced pinosylvin.

e) Extraction And Analysis of Pinosylvin in *Escherichia coli*

Extraction and analysis were performed using the methods as described in example 9. Results of HPLC conducted on the extracted materials from the fermentation using the engineered strain described and a control strain containing empty plasmids are shown in FIG. 9, upper and lower panels respectively. Pinosylvin and cinnamic acid production is marked in the figure.

Example 11 a) Construction of a Bacterial Vector for Expression of PAL2 in *Lactococcus lactis*

The plasmid pSH71 and derivatives thereof, which is used in the following examples, is a bifunctional shuttle vector with multiple origins of replication from *Escherichia coli* and *Lactococcus lactis*. With that, the host range specificity traverses *Escherichia coli* and other species of lactic acid bacteria. Though transformations in *Lactoccus lactis* usually proceed without problems, putative difficult transformations in other species of lactic acid bacteria can, therefore, be overcome by using *Escherichia coli* as an intermediate host for the construction of recombinant plasmids. The plasmid contains one or more marker genes to allow the microorganism that harbour them to be selected from those which do not. The selection system that is used for *Lactococcus lactis* is based upon dominant markers, e.g. resistance against erythromycin and chloramphenicol, but systems based upon genes involved in carbohydrate metabolism, peptidases and food grade markers, have also been described. In addition, the plasmid contains promoter- and terminator sequences that allow the expression of the recombinant genes. Suitable promoters are taken from genes of *Lactococcus lactis* e.g. lacA. Furthermore, the plasmid contains suitable unique restriction sites to facilitate the cloning of DNA fragments and subsequent identification of recombinants.

In the procedures below the plasmid contains either the erythromycine resistance gene, designated as pSH71-ERY$^r$, or the chloramphenicol resistance gene, designated as pSH71CM$^r$.

The gene encoding PAL2, isolated as described in example 1, is reamplified by PCR from the plasmid pESC-URA-PAL2 (example 2), using forward- and reverse primers, with 5' overhangs containing suitable restriction sites. The introduction of said restriction sites at the 5' and 3' ends of the gene allows ligation of the restricted PCR product into a digested pSH71-ERY$^r$ vector that contains the lacA promoter from *Lactococcus lactis*. The resulting plasmid, pSH71-ERY$^r$-PAL2, contains the gene encoding PAL2 under the control of the lacA promoter from *Lactococcuss lactis*. The sequence of the gene encoding PAL2 is verified by sequencing of two different clones of pSH71-ERY$^r$-PAL2.

b) Construction of a Bacterial Vector for Expression of 4CL1 and VST1 in *Lactococcus lactis*

The gene encoding 4CL1, isolated as described in example 1, is reamplified by PCR from the plasmid pESC-TRP-4CL1-VST1 (example 5), using forward- and reverse primers, with 5' overhangs containing suitable restriction sites. The introduction of said restriction sites at the 5' and 3' ends of the gene allows ligation of the restricted PCR product into a digested pSH71CM$^r$ vector. The resulting plasmid, pSH71CM$^r$-4CL1, contains the gene encoding for 4CL1 under the control of the lacA promoter from *Lactobacillus lactis*. The gene encoding VST1, isolated as described in example 1, is reamplified by PCR from the plasmid pESC-TRP-4CL1-VST1 (example 5) using forward- and reverse primers, with 5' overhangs containing suitable restriction sites. The introduction of said restriction sites at the 5' and 3' ends of the gene allows ligation of the restricted PCR product into a digested pSH71-ERY$^r$ vector. The resulting plasmid, pSH71-ERY$^r$-VST1, contains the gene encoding VST1 under the control of the lacA promoter from *Lactococcus lactis*. The lacA promoter and the gene encoding VST1 are reamplified as one fragment by PCR from the plasmid pSH71-ERY$^r$-VST1 using forward- and reverse primers, with 5' overhangs containing suitable restriction sites. The introduction of said restriction sites at the 5' and 3' ends of the DNA fragment allows ligation of the restricted PCR product into the digested plasmid pSH71-CM$^r$-4CL1. The resulting plasmid, pSH71-CM$^r$-4CL1-VST1, contains the genes encoding 4CL1 and VST1 that are each under the control of their individual lacA promoter. The sequence of the genes encoding 4CL1 and VST1 is verified by sequencing of two different clones of pSH71-CM$^r$-4CL1-VST1.

c) Expression of the Pathway to Pinosylvin in *Lactococcus lactis*

*Lactococcus lactis* strains are transformed with the vectors described in examples 16 and 17, separately or in combination. The transformation of the bacterial cell is conducted in accordance with methods known in the art, for instance, by using competent cells or by electroporation (see, e.g., Sambrook et al., 1989). Transformants are selected on medium containing the antibiotics erythromycin and chloramphenicol and streak purified on the same medium.

*Lactococcus lactis* strain MG1363 is transformed separately with the vector pSH71-ERY$^r$-PAL2 (example 16), yielding the strain FSLL-PAL2 In addition, *Lactococcus lactis* strain MG1363 is co-transformed with pSH71-ERY$^r$-PAL2 (example 16) and pSH71-CM$^r$-4CL1-VST1 (example 17), and the transformed strain is named FSLL-PAL24CL1VST1.

d) Fermentation with Recombinant *Lactococcus lactis* Strains in Fermentors

The recombinant *lactococcus* strains can be grown in fermenters operated as batch, fed-batch or chemostat cultures.
Batch and Fed-Batch Cultivations The microorganism is grown in a baffled bioreactor with a working volume of 1.5 liters under anaerobic, aerobic or microaerobic conditions. All cultures are incubated at 30° C., at 350 rpm. A constant pH of 6.6 is maintained by automatic addition of 10 M KOH. Cells are grown on lactose in defined MS10 medium supplemented with the following components to allow growth under aerobic conditions: $MnSO_4$ ($1.25 \times 10^{-5}$ g/l), thiamine (1 mg/l), and DL-6,8-thioctic acid (2.5 mg/l). The lactose concentration is, for example 50 g/l. The bioreactors are inoculated with cells from precultures grown at 30° C. in shake flasks on the medium described above buffered with threefold-higher concentrations of $K_2HPO_4$ and $KH_2PO_4$. Anaerobic conditions are ensured by flushing the medium with $N_2$ (99.998% pure) prior to inoculation and by maintaining a constant flow of 50 ml/min of $N_2$ through the headspace of the bioreactor during cultivation. The bioreactors used for microaerobic and aerobic cultivation are equipped with polarographic oxygen sensors that are calibrated with air (DOT, 100%) and $N_2$ (DOT, 0%). Aerobic conditions are obtained by sparging the bioreactor with air at a rate of 1 vvm to ensure that the DOT is more than 80%. During microaerobic experiments the DOT is kept constant 5% by sparging the reactor with gas composed of a mixture of $N_2$ and atmospheric air, at a rate of 0.25 vvm.
Chemostat Cultures In chemostat cultures the cells can be grown in, for example, 1-L working-volume Applikon laboratory fermentors at 30° C. and 350 rpm. The dilution rate (D) can be set at different values, e.g. at 0.050 h$^{-1}$, 0.10 h$^{-1}$, 0.15 h$^{-1}$, or 0.20 h$^{-1}$. The pH is kept constant, e.g at 6.6, by automatic addition of 5 M KOH, using the growth medium described above, supplemented with antifoam (50 µl/l). The concentration of lactose can be set at different values, e.g. is 3.0 g/l 6.0 g/l, 12.0 g/l, 15.0 g/l or 18.0 g/l. The bioreactor is inoculated to an initial biomass concentration of 1 mg/l and the feed pump is turned on at the end of the exponential growth phase.

An anaerobic steady state is obtained by introducing 50 ml/min of $N_2$ (99.998% pure) into the headspace of the bioreactor. Different anoxic steady states can obtained by sparging the reactor with 250 ml/min of gas composed of $N_2$ (99.998% pure) and atmospheric air at various ratios. The oxygen electrode is calibrated by sparging the bioreactor with air (100% DOT) and with $N_2$ (0% DOT).

For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.

Cultivations are considered to be in steady state after at least 5 residence times, and if the concentrations of biomass and fermentation end products remain unchanged (less than 5% relative deviation) over the last two residence times.

e) Extraction and Analysis of Pinosylvin in *Lactococcus lactis*

Extraction and analysis is performed using the methods as described in example 9.

Example 12 a) Construction of a Fungal Vector for Expression of PAL2 in Species Belonging to the Genus *Aspergillus*

The plasmid that is used in this example, is derived from pARp1 that contains the AMA1 initiating replication sequence from *Aspergillus nidulans*, which also sustains autonomous plasmid replication in *A. niger* and *A. oryzae* (Gems et al., 1991). Moreover, the plasmid is a shuttle vector, containing the replication sequence of *Escherichia coli*, and the inherent difficult transformations in *Aspergillus niger* and *Aspergillus oryzae* can therefore overcome by using *Escherichia coli* as an intermediate host for the construction of recombinant plasmids. The plasmid contains one or more marker genes to allow the microorganism that harbour them to be selected from those which do not. The selection system can be either based upon dominant markers e.g. resistance against hygromycin B, phleomycin and bleomycin, or heterologous markers e.g amino acids and the pyrG gene. In addition the plasmid contains promoter- and terminator sequences that allow the expression of the recombinant genes. Suitable promoters are taken from genes of *Aspergillus nidulans* e.g. alcA, glaA, amy, niaD, and gpdA. Furthermore, the plasmid contains suitable unique restriction sites to facilitate the cloning of DNA fragments and subsequent identification of recombinants.

The plasmid contains the strong constitutive gpdA-promoter and auxotropic markers, all originating from *Aspergillus nidulans*; the plasmid containing the gene methG that is involved in methionine biosynthesis, is designated as pAMA1-MET; the plasmid containing the gene hisA that is involved in histidine biosynthesis, is designated as pAMA1-HIS.

The gene encoding for PAL2, isolated as described in example 1, is reamplified by PCR from the plasmid pESC-URA-PAL2 (example 2) using forward- and reverse primers, with 5' overhangs containing suitable restriction sites. The introduction of said restriction sites at the 5' and 3' ends of the gene allows ligation of the restricted PCR product into a digested pAMA1-MET vector. The resulting plasmid, pAMA1-MET-PAL2, contains the gene encoding for PAL2 under the control of the gpdA promoter from *Aspergillus nidulans*. The sequence of the gene encoding for PAL2 is verified by sequencing of two different clones of pAMA1-MET-PAL2.

b) Construction of a Fungal Vector for Expression of 4CL1 and VST1 in Species Belonging to the Genus *Aspergillus*

The gene encoding 4CL1, isolated as described in example 1, is reamplified by PCR from the plasmid pESC-TRP-4CL1-VST1 (example 5), using forward- and reverse primers, with 5' overhangs containing suitable restriction sites. The introduction of said restriction sites at the 5' and 3' ends of the gene allows ligation of the restricted PCR product into a digested pAMA1-HIS vector that contains the gpdA promoter from *Aspergillus nidulans*. The resulting plasmid, pAMA1-HIS-4CL1 contains the gene encoding 4CL1 under the control of the gpdA promoter from *Aspergillus nidulans*. The gene encoding VST1, isolated as described in example 1, is reamplified by PCR from the plasmid pESC-TRP-4CL1-VST1 (example 5) using forward- and reverse primers, with 5' overhangs containing suitable restriction sites. The introduction of said restriction sites at the 5' and 3' ends of the gene allows ligation of the restricted PCR product into a digested pAMA1-MET vector to yield pAMA1-MET-VST1. The gpdA promoter and the gene encoding VST1 are reamplified as one fragment by PCR from the plasmid pAMA1-MET-VST1 using forward- and reverse primers, with 5' overhangs containing suitable restriction sites. The introduction of said restriction sites at the 5' and 3' ends of the DNA fragment allows ligation of the restricted PCR product into the digested plasmid pAMA1-HIS-4CL1. The resulting plasmid, pAMA1-HIS-4CL1-VST1, contains the genes encoding 4CL1 and VST1 that are each under the control of an individual pgdA promoter from *Aspergillus nidulans*. The sequence of the genes encoding 4CL1 and VST1 is verified by sequencing of two different clones of pAMA1-HIS-4CL1-VST1.

c) Expression of the Pathway to Pinosylvin in *Aspergillus niger*

*Aspergillus niger* strains are transformed with the vectors described in (a) and (b), separately or in combination. The transformation of the fungal cell is conducted in accordance with methods known in the art, for instance, by electroporation or by conjugation (see, e.g., Sambrook et al., 1989). Transformants are selected on minimal medium lacking methionine and/or histidine.

A strain of *Aspergillus niger* that is auxotrophic for histidine and methionine, for instance, strain FGSC A919 (see http://www.fgsc.net), is transformed separately with the vector pAMA1-MET-PAL2 (a), yielding the strain FSAN-PAL2 and with pAMA1-HIS-4CL1-VST1 (b), yielding strain FSAN-4CL1VST1. In addition, *Aspergillus niger* strain FGSC A919 is co-transformed with pAMA1-MET-PAL2 (a) and pAMA1-HIS-4CL1-VST1 (b), and the transformed strain is named FSAN-PAL24CL1VST1.

Example 13

Expression of the Pathway to Pinosylvin in *Aspergillus oryzae*

A strain of *Aspergillus oryzae* that contains a native set of genes encoding for PAL2 and 4CL1 (Seshime et al., 2005) and that is auxotrophic for methionine, is transformed with the vector pAMA1-MET-VST1 (example 29), yielding the strain FSAO-VST1. The transformation of the fungal cell is conducted in accordance with methods known in the art, for instance, by electroporation or by conjugation (see, e.g., Sambrook et al., 1989). Transformants are selected on minimal medium lacking methionine.

Example 14

Fermentation with Recombinant Strains of *Aspergillus niger* and *Aspergillus oryzae* in Fermentors The recombinant *Aspergillus* strains can be grown in fermenters operated as batch, fed-batch or chemostat cultures.
Batch and Fed-Batch Cultivations The microorganism is grown in a baffled bioreactor with a working volume of 1.5 liters under aerobic conditions. All cultures are incubated at 30° C., at 500 rpm. A constant pH of 6.0 is maintained by automatic addition of 10 M KOH, and aerobic conditions are obtained by sparging the bioreactor with air at a rate of 1 vvm to ensure that the DOT is more than 80%. Cells are grown on glucose in defined medium consisting of the following components to allow growth in batch cultivations: 7.3 g/l $(NH_4)_2SO_4$, 1.5 g/l $KH_2PO_4$, 1.0 g/l $MgSO_4.7H_2O$, 1.0 g/l NaCl, 0.1 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.7H_2O$. The glucose concentration is, for example, 10-20-, 30-, 40- or 50 g/l. To allow growth in fed-batch cultivations the medium is composed of: 7.3 g/l $(NH_4)_2SO_4$, 4.0 g/l $KH_2PO_4$, 1.9 g/l $MgSO_4.7H_2O$, 1.3 g/l NaCl, 0.10 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.H_2O$ in the batch phase. The reactor is then fed with, for example, 285 g/kg glucose and 42 g/kg $(NH_4)_2SO_4$.

Free mycelium from a pre-batch is used for inoculating the batch- and fed-batch cultures. A spore concentration of $2.10^9$ spores/l is used for inoculation of the pre-batch culture at pH 2.5. Spores are obtained by propagation of freeze-dried spores onto 29 g rice to which the following components are added: 6 ml 15 g/l sucrose, 2.3 g/l $(NH_4)_2SO_4$, 1.0 g/l $KH_2PO_4$, 0.5 g/l $MgSO_4.7H_2O$, 0.50 g/l NaCl, 14.3 mg/l $ZnSO_4.7H_2O$, 2.5 mg/l $CuSO_4.5H_2O$, 0.50 mg/l $NiCl_2.6H_2O$, and 13.8 mg/l $FeSO_4.7H_2O$. The spores are propagated at 30° C. for 7-14 days to yield a black layer of spores on the rice grains and are harvested by adding 100 ml of 0.1% Tween 20 in sterile water. For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.
Chemostat Cultures In chemostat cultures the cells can be grown in, for example, 1.5-L working-volume Biostat B laboratory fermentors at 30° C. and 500 rpm. A constant pH of 6.0 is maintained by automatic addition of 10 M KOH, and aerobic conditions are obtained by sparging the bioreactor with air at a rate of 1 vvm to ensure that the DOT is more than 80%. The dilution rate (D) can be set at different values, e.g. at 0.050 $h^{-1}$, 0.10 $h^{-1}$, 0.15 $h^{-1}$, or 0.20 $h^{-1}$. The pH is kept constant, e.g at 6.6, by automatic addition of 10 M KOH, using a minimal growth medium with the following components: 2.5 g/l $(NH_4)_2SO_4$, 0.75 g/l $KH_2PO_4$, 1.0 g/l $MgSO_4.7H_2O$, 1.0 g/l NaCl, 0.1 g/l $CaCl_2.2H_2O$, 0.1 ml/l Sigma antifoam, 7.2 mg/l $ZnSO_4.7H_2O$, 1.3 mg/l $CuSO_4.5H_2O$, 0.3 mg/l $NiCl_2.6H_2O$, 3.5 mg/l $MnCl_2.4H_2O$ and 6.9 mg/l $FeSO_4.7H_2O$. The concentration of glucose can be set at different values, e.g. is 3.0 g/l 6.0 g/l, 12.0 g/l, 15.0 g/l or 18.0 g/l. The bioreactor is inoculated with free mycelium from a pre-batch culture as described above, and the feed pump is turned on at the end of the exponential growth phase.

For all conditions, the gas is sterile filtered before being introduced into the bioreactor. The off gas is led through a condenser cooled to lower than −8° C. and analyzed for its volumetric content of $CO_2$ and $O_2$ by means of an acoustic gas analyser.

Cultivations are considered to be in steady state after at least 5 residence times, and if the concentrations of biomass glucose and composition of the off-gas remain unchanged (less than 5% relative deviation) over the last two residence times.

Example 15

Extraction and Analysis of Pinosylvin in *Aspergillus niger* and *Aspergillus oryzae*

Extraction and analysis is performed using the methods as described in Example 9.

Example 16

Pinosylvin Production in *Aspergillus nidulans* Ar1

*Aspergillus nidulans* AR1 has deleted the following genes genes argB2, pyrGB9, veA.

a) Construction of a Filamentous Fungal Expression Vector, with argB (Ornithine Carbamoyltransferase) Marker The gene encoding argB including the homologous promoter and terminator sequence was amplified from *Aspergillus nidulans* AR1 genomic DNA using forward primer 5-CG GAATTC ATA CGC GGT TTT TTG GGG TAG TCA-3 (SEQ ID NO: 17) and the reverse primer 5-CG CCCGGG TAT GCC ACC TAC AGC CAT TGC GAA-3 (SEQ ID NO: 18) with the 5' overhang containing the restriction sites EcoRI and XmaI respectively.

The incorporated restriction sites in the PCR product allowed insertion into pUC19 (New England biolabs, Ipswich, Mass.) digested with EcoRI and XmaI giving pUC19-argB.

The trpC (Indole-3-glycerol phosphate synthase) terminator was amplified from *A. nidulans* genomic DNA using forward primer 5-GC GGATCC ATA GGG CGC TTA CAC AGT ACA CGA-3 (SEQ ID NO: 19) and the reverse primer 5-CGGAGAGGGCGCGCCCGTGGCGGCCGC GGA TCC ACT TAA CGT TAC TGA-3 (SEQ ID NO: 20) with the 5' overhang containing the restriction site BamHI and a 27 base pair adaptamer respectively.

The gpdA (glyceraldehyde-3-phosphate dehydrogenase) promoter was amplified from *A. nidulans* AR1 genomic DNA using forward primer 5-GCGGCCGCCACGGGCGCGC-CCTCTCCG GCG GTA GTG ATG TCT GCT CAA-3 (SEQ ID NO: 21) and the reverse primer 5-CG AAGCTT TAT AAT TCC CTT GTA TCT CTA CAC-3 (SEQ ID NO: 22) with the 5' overhang containing a 27 base pair adaptamer and the restriction site HindIII respectively.

The fusion PCR product of fragment trpC and gpdA with the incorporated restriction sites allow insertion into pUC19-argB digested with BamHI and HindIII yielding pAT3.

b) Construction of a Filamentous Fungal Expression Vector With pyrG (Orotidine-5'-Monophosphate Decarboxylase) Marker For Expression of C4H (Cinnamate-4-Hydroxylase) in *A. nidulans* AR1

The gene encoding C4H was reamplified from the yeast plasmid pESC-URA-PAL2-C4H (WO2006089898, example 3) using the forward primer 5-CG G CGCG C ATA ATG GAC CTC CTC TTG CTG GAG-3 (SEQ ID NO: 23) and the reverse primer 5-GG GC GGCC GC TTA TTA ACA GTT CCT TGG TTT CAT AAC G-3 (SEQ ID NO: 24) with the 5' overhang containing the restriction sites BssHII and NotI respectively. The incorporated restriction sites in the PCR product allowed insertion into pAT3 digested with BssHII and NotI giving pAT3-C4H. The construct was verified by restriction enzyme cut and sequencing. The argB marker was removed by using the two following restriction enzymes BsiWI and PciI.

The gene encoding pyrG including the homologous promoter and terminator sequence was reamplified from *Aspergillus fumigatus* genomic DNA using the forward primer 5-CGT GTAC AATA TTA AT TAA CGAGA GCG AT CGC AAT AAC CGT ATT ACC GCC TTT GAG-3 (SEQ ID NO: 25) and reverse primer 5-CGA CATG TAT TCC CGG GAA GAT CTC ATG GTC A-3 (SEQ ID NO: 26) with the 5' overhang containing the restriction sites BsrGI, PacI, AsiSI in the forward primer and PciI in the reverse primer. The incorporated restriction sites in the PCR product allowed insertion into pAT3 digested with BsiWI and PciI giving pAT3-C4H-pyrG. The construct was verified by restriction enzyme cut and sequencing.

c) Construction of a Filamentous Fungal Expression Vector with argB Marker for Expression of 4CL1 (4-Coumarate-CoA Ligase) in *A. nidulans* AR1

The gene encoding 4CL1 was reamplified from the yeast plasmid pESC-TRP-4CL1-VST1 using the forward primer 5-GCGGAGAGGGCGCG ATG GCG CCA CAA GAA CAA GCA-3 (SEQ ID NO: 27) and the reverse primer 5-TG-GATCCGCGGCCGC TCA CAA TCC ATT TGC TAG TTT TGC-3 (SEQ ID NO: 28). The 4CL1 gene was inserted into a pAT3 vector digested with BssHII and NotI using the In-fusion™ PCR cloning Technology (Clontech, Mountain View, Calif.) to yield pAT3-4CL1. The construct was verified by restriction enzyme cut and sequencing.

d) Construction of a Filamentous Fungal Expression Vector with argB Marker for Expression of VST1 (Resveratrol Synthase) in *A. nidulans* AR1

The gene encoding VST1 was reamplified from the yeast plasmid pESC-TRP-4CL1-VST1 (example 5) using the forward primer 5-CG G CGCG C ATA ATG GCA TCC GTA GAG GAG TTC-3 (SEQ ID NO: 29) and the reverse primer 5-GG GC GGCC GC TTA TCA TTA GTT AGT GAC AGT TGG AA-3 (SEQ ID NO: 30) with the 5' overhang containing the restriction sites BssHII and NotI respectively. The incorporated restriction sites in the PCR product allowed insertion into pAT3 digested with BssHII and NotI giving pAT3-VST1. The construct was verified by restriction enzyme cut and sequencing.

e) Expression of the Pathway Leading to Pinosylvin in *A. nidulans* AR1 (the Strain has Deletions (argB2, pyrG89, veA1)) Using C4H, 4CL1 and VST1

The transformation of the *A. nidulans* AR1 fungal cell was conducted in accordance with methods known in the art by protoplastation using cell wall lysing enzymes (glucanex, novozymes) Tilburn et al., 1983. Random integration of C4H, 4CL1 and VST1 was conducted in two steps. Plasmid pAT3-4CL1 and pAT3-VST1 were linearized using restriction enzyme BmrI and integrated in the genome by co-transformation according to Guerra et al., 2006 utilizing the auxotrophic marker argB. A transformant containing a 4CL1 and VST1 expression cassette was isolated and a successive transformation with pAT3-C4H-pyrG, which was linearized with BmrI, gave a recombinant *A. nidulans* strain containing C4H, 4CL1 and VST1.

f) Fermentation with Recombinant *A. nidulans* Strains in Shake Flasks

Precultures of *A. nidulans* were grown for 5 days on agar plates at 37° C. containing 1 g/L glucose, 0.85 g/L $NaNO_3$, 0.1 g/L KCl, 0.1 g/L $MgSO_4.7H_2O$; and 0.3 g/L $KH_2PO_4$, 0.00008 g/L $CuSO_4.5H_2O$, 0.000008 g/L $Na_2B_4O_7.10H_2O$, 0.00016 g/L $FeSO_4.7H_2O$, 0.00016 g/L $MnSO_4.2H_2O$, 0.00016 g/L $Na_2MoO_4.2H_2O$, and 0.0016 g/L $ZnSO_4.7H_2O$. The precultures were used for inoculation of 500 ml baffled shake flasks containing 100 ml Czapek medium (CZ). The shake flasks were incubated at 150 rpm and 30° C. and the initial pH of the medium was 6.2. After an incubation period of 24 hours, the samples were taken and subjected to extraction procedures (see below) and analyzed for the presence of produced pinosylvin.

g) Extraction of Pinosylvin from *A. nidulans* Shake Flask Cultures

Samples consisting of 100 ml cultures (both cells and broth) were withdrawn from the shake flasks. Extraction of metabolites were conducted as follows; the samples were transferred into two 50 ml Sartorius tubes and centrifuged at 4500 rpm for 10 minutes. The supernatant was transferred into a beaker and the biomass was divided into eight aliquots that were transferred to 2 ml Sarstedt micro tubes with cap, containing app. 300 µl glass beads (0.25-0.50 mm). The tubes were inserted into a Fastprep 120 (Thermo Fisher Scientific, Waltham, Mass.) for four cycles at level 6.5 for 30 seconds at a time and kept on ice in between cycles. The crushed cells were divided into two 15-ml Sartorius tubes. The tubes were filled with 10 ml of supernatant and 3 ml of ethyl acetate was added. The tubes were vigorously mixed on a whirly mixer for 2 minutes and put on ice for 5 minutes. The ethyl acetate phase was then separated from the water phase via centrifugation at 4500 rpm for 10 minutes and collected in four 1.5 ml Eppendorf tubes. The ethyl acetate was then freeze dried for 45 min and the dried samples were re-dissolved in 0.3 ml 50% methanol for further HPLC analysis, as described in Example 9b.

h) Shake Flask Results from Recombinant *A. nidulans*

Figure 7:
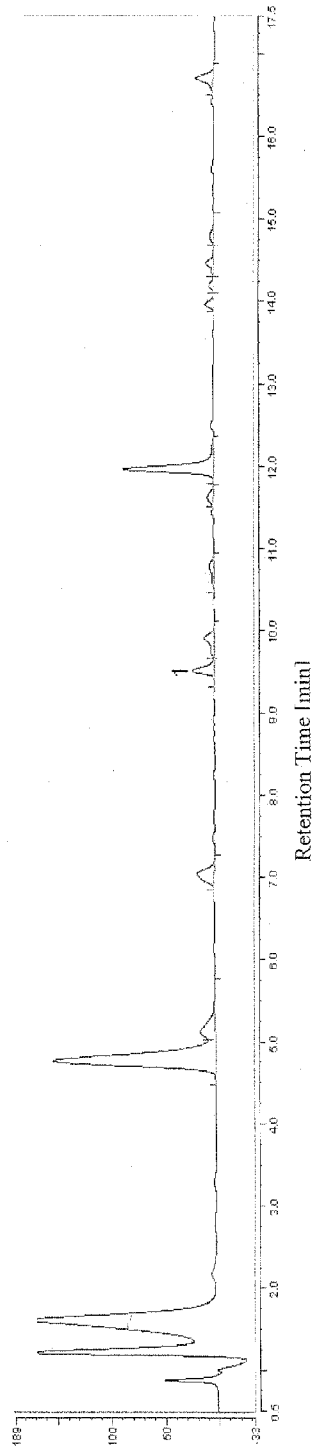
FIG. 7 shows HPLC chromatograms obtained in Example 16.
Figure 7:
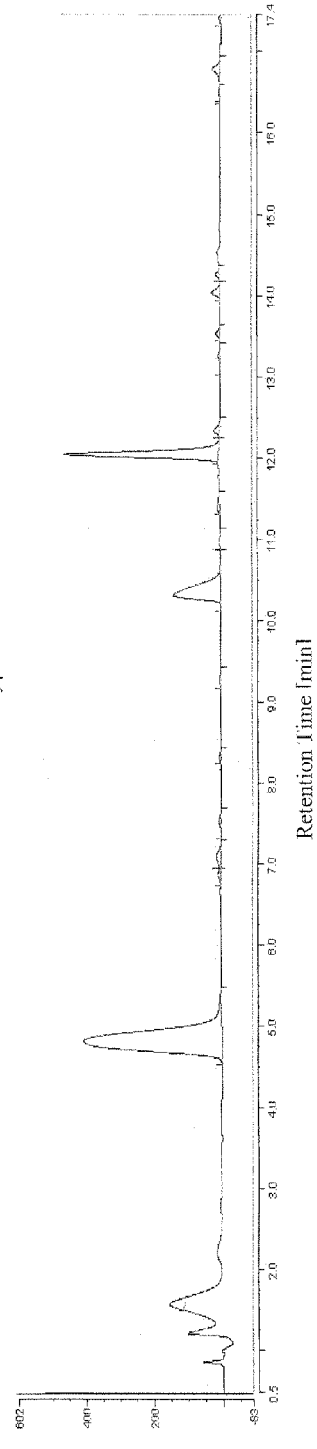

FIG. 7 shows HPLC-chromatograms from a typical shake flask experiment. The upper panel shows results from the engineered strain producing pinosylvin and the lower panel shows the results from the parent wild type control strain. The pinosylvin levels produced by the engineered strain varied between 1.0-2.0 mg/l. The control strain did not show any pinosylvin formation.

Figure 8:
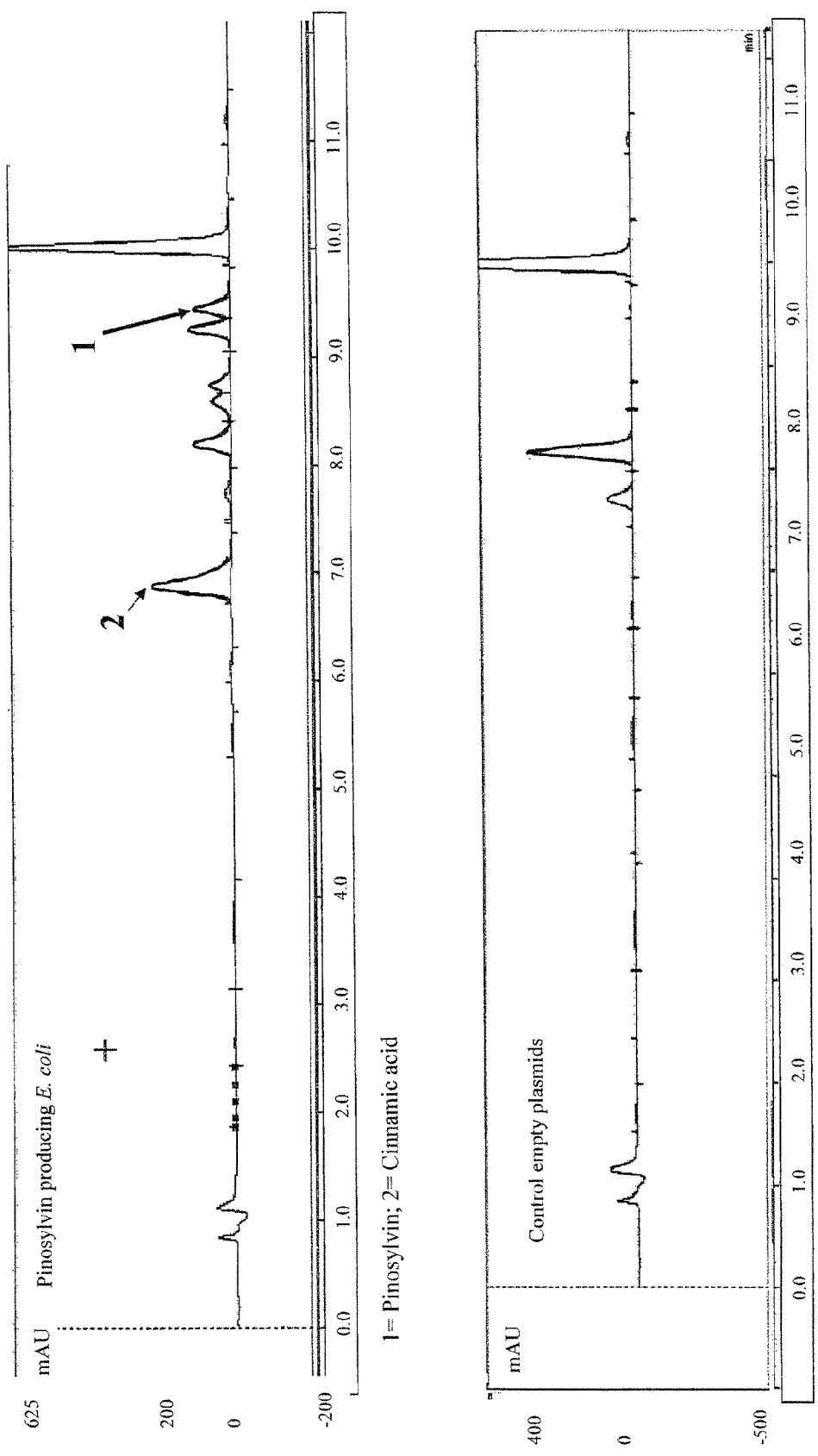
FIG. 8 shows the HPLC analysis of extracted product from the fermentation of a pinosylvin producing strain of E. coli (upper panel) and a control strain (lower panel).

The identity of the pinosylvin peak was further confirmed with diode array UV-spectra by comparison with a pure standard UV-chromatogram (FIG. 8).

Example 17

Determination of Intracellular and Extracellular Levels of Stilbenoids in a Continuous Culture of PALCPR A yeast strain FSSC-PAL2C4H4CL2VST1-pADH1CPR1 with overexpressed CPR, was grown in a carbon-limited continuous culture with a working volume of 1 liter. The culture was fed with a defined medium according to Verduyn et al. (1992), containing: 5.0 g/L $(NH_4)_2SO_4$; 3.0 g/L $KH_2PO_4$; 0.5 g/L $MgSO_4 \cdot 7H_2O$; trace metals and vitamins and 5 g/l glucose and 35 g/l galactose as the growth-limiting nutrients. Antifoam (300 µl/L, Sigma A-8436) was added to avoid foaming. The carbon source was autoclaved separately from the mineral medium and afterwards added to the fermentor. In addition, the vitamin and trace metal solutions were added to the fermentor by sterile filtration following autoclavation and cooling of the medium. The fermentor system was from Sartorius BBI systems and consisted of a baffled 3-liter reactor vessel with 1 liter working volume equipped with Biostat B Plus controller. The reactor vessel was equipped with two Rushton turbines which were rotating at either 1000 rpm, the temperature was kept at 30±1° C., and the pH was kept at 5.5±0.2 by automatic addition of 2M KOH. The gasflow was controlled by a mass flow controller and was set to 1.5 vvm (1.5 l/min). The off-gas was led through a cooled condenser, and was analyzed for $O_2$ and $CO_2$ (Model 1308, Innova, Denmark). An initial batch culture with 35 g/l galactose was started by inoculation of the culture with 10 ml of an expotentional growing shakeflask culture containing 5 g/l glucose and 35 g/l galactose. The batch cultivation was switched to a continuous mode by feeding the same medium continuously to the reactor. The dilution rate was controlled on a constant level basis, aiming at $D=0.050\ h^{-1}$. The continuous culture was regarded to be in steady state when both the dilution rate and off-gas signal had not changed for at least five residence times, and when the metabolite concentrations in two successive samples taken at intervals of 1 residence time, deviated by less than 3%. The dissolved-oxygen concentration, which was continuously monitored, was kept above 60% of air saturation. Under said conditions the strain consumed all the galactose, and mainly produced biomass and $CO_2$, and only minor amounts of ethanol. Moreover, the RQ was close to unity, indicating that metabolism was predominantly in respirative mode.

For the determination of stilbenoids, samples were taken at approximately 300 hrs into fermentation corresponding to 15 residence times. Cells were harvested by centrifugation 5000 g for 5 minutes. For the determination of extracellular levels of stilbenoids, an aliquot of 25 ml of supernatant was extracted once with 10 ml ethyl acetate. The ethyl acetate was freeze dried and the dry product redissolved in 0.6 ml methanol. The samples were than 50-fold diluted in water transferred into HPLC vials, and analyzed by HPLC. Furthermore, to evaluate whether the level of stilbenoids that was produced exceeded the solubility of the medium, or were either bound to the cell-membranes 1 ml aliquots of cell culture, thus including both cells and medium, were mixed with 1 ml of 100% ethanol, and mixed vigorously prior to centrifugation. The supernatant was then transferred into HPLC vials and directly analyzed for the content of stilbenoids. For the determination of intracellular levels of stilbenoids, an aliquot of 50 ml culture was sampled, and cells and medium were separated by centrifugation. The pellet was washed with 50 ml of water to remove any stilbenoids that were cell-bound or trapped into the pellet; after re-centrifugation the pellet was then dissolved in 1 ml water. The resulting cell suspension was distributed into extraction tubes and broken with glass beads using a fast-prep machine. The crude extracts were pooled into 10 ml of 100% methanol, and extracted in a rotary chamber for 24 hours in a dark cold room at 4° C. Thereafter, the cell debris was removed via centrifugation for 5 min. at 5000 g and the remaining methanol was removed by freeze-drying overnight. The dry residue was redissolved in 0.4 ml methanol and 0.1 ml water. The samples were than 50-fold diluted in water and then transferred into HPLC vials, and analyzed by HPLC.

The following table summarizes the results after continuous culture for 300 hrs:

|  | Pinosylvin Intracelullar (a) | Pinosylvin Extracelullar (b) | Pinosylvin Extracellular In EtOH (c) | Pinosylvin Total (a + c) |
|---|---|---|---|---|
| mg/l | 16.45 | 12.55 | 113.57 | 130.02 |
| % of total | 12.65 | 9.65 | 87.35 | 100.00 |
| mg/g dry weight | 1.83 | — | — | — |

Intracellular levels of stilbenoids were expressed in mg per gram biomass (dry weight), according to the calculation explained in the following section. The concentration of pinosylvin in the extract was determined 1646 mg/l; the volume of the extract was 0.5 ml, hence the absolute amount of pinosylvin extracted was 0.5*1646/1000=0.8230 mg respectively. The stilbenoids were extracted from a 50 ml culture-aliquot and hence the intracellular concentrations of pinosylvin expressed per liter culture were 0.8230*(1000/50)=16.46 mg/l. The biomass concentration of said culture was 9 g/l. The intracellular pinosylvin levels expressed per gram dry weight therefore were 16.46/9=1.83 mg/g dry weight.

Example 18

Cloning of Trans-Pinosylvin Pathway in Oleaginous Yeast *Yarrowia lipolytica* a) Isolation of Genes

PAL (phenylalanine ammonialyase), CL (cinnamoyl:CoA ligase) and VST1 genes, where gene is defined as protein coding sequence, are produced as synthetic genes (GenScript Corporation, Piscataway, N.J.) with codon optimization for expression in *Yarrowia lipolytica*. The determination of codon usage in *Y. lioplytica* has been described previously (WO2006125000). PAL and 4CL genes can also be isolated by PCR from *A. thaliana* cDNA (Stratagene). Cinnamoyl:CoA ligase CL can be any hydroxycinnamoyl:CoA ligase accepting cinnamic acid as substrate. For example, the 4-coumaroyl:CoA ligases from *A. thaliana*, encoded by 4CL1 and 4CL2 genes, accept cinnamic acid although the preferred substrate is 4-hydroxycinnamic acid (coumaric acid) (Hamberger and Hahlbrock, 2004; Costa et al, 2005). Most preferably, the CL is a codon optimized ligase specific for cinnamic acid as substrate exemplified by cinnamate:CoA ligase from *Streptomyces coelicolor* (Kaneko et al, 2003). Likewise, VST1 gene can be any codon optimized or non optimized stilbene synthase accepting cinnamoyl:CoA as substrate even though the preferred substrate is usually 4-coumaroyl:CoA in stilbene synthases that produce resveratrol, so called resveratrol synthases. This type of dual substrate acceptance is in the nature of the VST1 gene (seq id: 9) from *Vitis vinifera*. Most preferably a stilbene synthase from the family of *Pinus* specific for cinnamoyl:CoA as substrate is used (Schanz et al, 1992; Kodan et al, 2002).

b) Isolation of Promoters and Terminators

Promoters that can be used for expression of heterologous genes in *Yarrowia lipolytica* are exemplified but not limited to the following promoters: long chain acyl:CoA oxidase POX2, hp4d, isocitrate lyase ICL1, extracellular alkaline protease XPR2, translation elongation factor TEF, ribosomal protein S7 RPS7, glyceraldehyde-3-phosphate dehydrogenase GPD, YAT1, GPAT, FBA1, and FBAIN promoters (Müller et al, 1998: WO2006055322; WO2006125000).

Terminators that can be used for expression of heterologous genes in *Yarrowia lipolytica* are exemplified but not limited to the following terminators: XPR2, LIP2, PEX20, and SQS terminators (Merkulov et al, 2000; WO2006055322; WO2006125000).

Isolation of terminator and promoter DNA fragments can be done via PCR from *Yarrowia lipolytica* genomic DNA prepared from whole cells of *Y. lipolytica* exemplified by but not limited to cells from the America Type Culture Collection, such as ATCC16618, ATCC18943, and ATCC18944, ATCC90811, ATCC90812, and ATCC90903.

c) Generation of an Expression Cassette

The generation of an expression cassette means the assembly of a linear double stranded DNA-fragment consisting of a promoter (constitutive or inducible) fused together with the protein coding sequence of a heterologous gene and a terminator sequence, i.e. 5'-Promoter::Gene::Terminator-3' DNA fragment.

The expression cassette can be generated by a combination of fusion PCR of the different gene fragments; promoter, gene coding sequence and terminal fragment. For example PAL gene can be fused with PCR technology to XPR2 promoter and the resulting XPR2::PAL fragment can be further fused via a second PCR reaction to the terminator to generate the expression cassette XPR2::PAL::terminator.

An alternative way to generate an expression cassette is to clone the protein coding sequence of the heterologous gene (such as PAL) in an existing expression vector, exemplified but not limited to ATCC vector 69355™. This ATCC vector already has a promoter (XPR2) and a terminator region and a multiple cloning site (MCS) with unique restriction sites between the promoter and terminator for introduction of a heterologous gene by standard molecular biology tools. If the number of restriction sites between promoter and terminator region in the target vector are limited the Infusion cloning kit technology can be used (Clontech, CA, USA) since it requires only one restriction site in the vector for gene insertion. By inserting the gene in a vector between a promoter and terminator the expression cassette Promoter::Gene::Terminator is created inside a circular vector and not as a single double stranded DNA-fragment. If a linear DNA expression cassette fragment is needed PCR can be used for amplification of the expression cassette from the expression vector. One of skill in the art would recognize that several expression cassettes can be introduced into the same plasmid or vector resulting in cluster of expression cassettes preferably with genes from a whole metabolic pathway, such as the pinosylvin production pathway (PAL, CL and VST1 genes). The cluster of expression cassettes for the three genes needed for pinosylvin production (PAL, CL and VST1) is defined as pinosylvin pathway expression cluster.

d) Insertion of Heterologous Gene, PAL, CL and VST1 for Pinosylvin Production in *Y. lipolytica*

The pinosylvin pathway genes (PAL, CL, VST1) are assembled as expression cassettes with a promoter and terminator Promoter::Gene:Terminator. The promoters and terminators can be the same or a combination of different promoters and terminators for the different genes, PAL, CL and VST1. One of skill in the art would recognize available cloning techniques, cloning vectors, or cloning tools needed for introduction and expression of the pinosylvin pathway expression cluster (comprising the expression cassettes with the genes PAL, CL and VST1) in *Y. lipolytica*, since these tools have been described in several publications (Le DAll et al, 1994; Pignede et al, 2000; Juretzek et al, 2001; Madzak et al, 2004) and patent applications (WO2006055322; WO2006125000).

In summary, once the expression cassettes suitable for expressing the pinosylvin pathway (PAL, CL and VST1) in *Y. lipolytica* has been obtained, they can be (i) placed in a plasmid vector capable of autonomous replication in a host cell or (ii) directly integrated into the genome of the host cell or a combination thereof in order to establish the pinosylvin pathway expression cluster in the *Y. lipolytica* host. Expression cassettes can be designed to integrate randomly within the host genome or can be targeted to specific locations. In both cases the expression cassette is further constructed to contain surrounding regions of homology to the host genome on both sides of the expression cassette. The regions of homology can be 20-1000 base pairs sufficient to target recombination with the host locus. Single copies can be targeted to any part of the genome which will not lead to deletion of an essential gene. Integration into multiple locations within the *Y. lipolytica* genome can be particularly useful when high expression levels of genes are desired and targets for integration of multiple copies of expression cassettes are exemplified but not limited to ribosomal DNA sequence (rDNA) or retrotransposon-like elements (TY1 elements) (Pignede et al, 2000). When integrating multiple copies of expression cassettes targeted to random positions into the *Y. lipolytica* genome the expression cassette Promoter-Gene-Terminator can actually be made shorter, including only Promoter-Gene since the integration will allow terminators already present in the *Y. lipolytica* genome to serve as the terminator for the expression cassette.

It is also possible to integrate plasmid DNA comprising expression cassettes into alternate loci to reach the desired copy number for the expression cassette, exemplified by but not limited to the URA3 locus (Accession No AJ306421) and the LEU2 locus (Accession No AF260230). The LEU2 integrative vector is exemplified by but not limited to ATCC vector 69355™. This expression vector containing an expression cassette can be used directly for transformation into *Y. lipolytica* cells auxotrophic for leucine for selection of the expression vector that contains *Y. lipolytica* LEU2 marker gene. The expression cassette can also be amplified from the expression vector by PCR technique to be further used for construction of other expression vectors containing appropriate selective antibiotic markers or biosynthetic amino acid markers.

The URA3 integration site can be used repeatedly in combination with 5-fluoroorotic acid (5-FOA) selection. In detail, native URA3 gene is deleted in *Y. lipolytica* host strain to generate a strain having URA-auxotrophic phenotype, wherein selection occurs based on 5-FOA resistance. When URA3 is present 5-FOA is degraded to a toxic compound 5-fluorouracil by the orotidine-5'-phosphate decarboxylase encoded by URA3 gene and only cells lacking URA3 gene will be resistant. Consequently, a cluster of multiple expression cassettes and a new URA3 gene can be integrated in multiple rounds into different locus of the *Yarrowia lipolytica* genome to thereby produce new strain having URA+ prototrophic phenotype. Subsequent integration produces a new URA3-auxotrophic strain, again using 5-FOA selection, when the introduced URA3 gene is autonomously deleted (so called loop-out or pop-out). Thus, URA3 gene in combination with 5-FOA selection can be used as a selection marker in multiple rounds of genetic modifications and integration of expression cassettes.

e) Transformation of *Y. lipolytica*

Standard transformation techniques (Chen et al, 1997; WO2006125000) can be used to introduce the foreign DNA, self replicative vectors, or DNA fragments comprising the expression cassettes into *Y. lipolytica* host, exemplified by but not limited to host cells such as ATCC90811, ATCC90812, and ATCC90903. The selection method used to maintain the introduced foreign DNA in *Y. lipolytica* can be based on amino acid markers (Fickers et al, 2003) or antibiotic markers (Cordero et al, 1996).

Example 19

(a) Batch Cultivations with Recombinant *Escherichia coli* Strains

The recombinant strains of *Escherichia coli* FSEC-PAL24CL1VST1 and BL21 (DE3) (control strain) were grown in baffled bioreactors with a working volume of 1.5 liters, under aerobic conditions. The cultures were incubated at 30° C., at 800 rpm. A constant pH of 7 was maintained by automatic addition of 2N KOH. Aerobic conditions were obtained by sparging the bioreactor with air at a rate of 1 vvm to ensure that the dissolved oxygen density (DOT) was greater than 60%. The air was sterile filtered before being introduced into the bioreactors. The off gas was led through a condenser cooled to lower than 6° C. and analyzed for its volumetric content of $CO_2$ and $O_2$ by means of an acoustic gas analyser. The bioreactors were equipped with polarographic oxygen sensors that were calibrated with air (DOT, 100%) and $N_2$ (DOT, 0%).

Cells were grown on glycerol in semi-defined medium consisting of the following components to allow growth in batch cultivations: 6.0 g/l yeast extract, 27.2 g/l $Na_2HPO_4$ (anhydrous), 12.0 g/l $KH_2PO_4$, 2.0 g/l NaCl, and 4.0 g/l $NH_4Cl$. The glycerol concentration was 20 g/l. The medium was supplemented with 50 mg/l ampicilin and 50 mg/l kanamycin. Antifoam was added to a final concentration of 50 ul/l.

The bioreactors were inoculated with 1 ml of glycerol stock culture of the recombinant strain, leading to a final optical density at 600 nm of approximately 0.03. The glycerol stock cultures were obtained by growing the cells in shake flasks on semi-defined medium, at 30° C. and 150 rpm. The composition of the medium was identical to the one described above, but re-scaled 4-fold lower, i.e.: 5 g/l glycerol, 1.5 g/l yeast extract, 6.8 g/l $Na_2HPO_4$ (anhydrous), 3.0 g/l $KH_2PO_4$, 0.5 g/l NaCl, and 1.0 g/l $NH_4Cl$. The medium was supplemented with 50 mg/l ampicilin and 50 mg/l kanamycin. The cells were harvested during the late exponential phase, collected by centrifugation and resuspended in an appropriate volume of sterile glycerol solution 15% (w/v), such that the final optical density at 600 nm was 30. Aliquots of 1 ml of suspended cells were stored at −80° C.

After the cells started growing in the bioreactors (5.5 h after inoculation), isopropyl β-thiogalactopyranoside (IPTG) was added to a final concentration of 1 mM, as an inducer of the T7 promoter that is in front of each of the three genes PAL2, 4CL1, and VST1.

Samples of cellular broth were taken in the course of the batch cultivations and analysed for the presence of pinosylvin. In addition, the samples were analysed for biomass (in terms of optical density OD600), carbon source (glycerol) and major by-products (ethanol, acetate, pyruvate, succinate).

(b) Extraction of Pinosylvin in *Escherichia coli*

The intracellular pinosylvin was extracted with ethyl acetate. For the purpose, 4 mL of ethyl acetate was added to 8 mL of cell broth. The extraction was enforced by mixing (30 s) and the separation of phases, by centrifugation (4500 rpm for 5 min, at 4° C.). The acetate phase was subjected to freeze-drying (approximately 2 h) and the dry product was redissolved in 0.5 ml methanol and analysed by HPLC. These samples were further diluted in water (1:5) and analysed by HPLC.

(c) Analysis of Pinosylvin

The analysis of pinosylvin in samples from the batch cultivation was performed using the method as described in Example 9b. The sample was previously subjected to the following sample preparation procedures, carried out in parallel: (i) Centrifugation of cell broth (5 min) and analysis of supernatant; (ii) Addition of ethanol (99.9%) to a final concentration of 50% (v/v), vortex (30 s), centrifugation (5 min) and analysis of supernatant; (iii) Extraction with ethyl acetate, according to (b) above, and analysis of dried sample redissolved in methanol.

Results

The recombinant strains of *Escherichia coli* FSEC-PAL24CL1VST1 and BL21 (DE3) (control strain), as described in example 10c, were cultivated on 20 g/L of glycerol in bioreactors in batch mode, as described in (a) above. In the course of the cultivations, the recombinant strains were analysed for their content of pinosylvin according to (c) above.

The HPLC-analysis showed that the strain FSEC-PAL24CL1VST1 contained a component with a retention time identical to the standard of trans-pinosylvin (FIGS. 4 and 5). In addition, the UV absorption spectra were similar to the absorption spectrum of pure trans-pinosylvin (not shown), with a $\lambda_{max}$ of approximately 306 nm.

The maximal concentrations of pinosylvin detected are shown in the following table:

|  | Pinosylvin intracellular (a) | Pinosylvin extracellular (b) | Pinosylvin extracellular In EtOH (c) | Pinosylvin total (a) + (c) |
|---|---|---|---|---|
| mg/l | 0.016 | (*) | (*) | 0.016 |
| % of total | 100 | 0 | 0 | 100 |
| mg/g dry weight | () | () | () | () |

(*) below detection level.
(**) not determined.

No pinosylvin was detected in the samples from the batch cultivation with the control strain.

The results, therefore, demonstrated the presence of an active phenyl-propanoid pathway that led to in vivo production of trans-pinosylvin, in *E. coli* grown in a bioreactor in batch mode.

Example 20

(a) Batch Cultivation with Recombinant *Aspergillus nidulans* Strain

The recombinant strain of *Aspergillus nidulans* containing C4H, 4CL1, and VST1 was grown in a baffled bioreactor with a working volume of 1.5 liters, under aerobic conditions. The cultures were incubated at 30° C., at 700 rpm. A constant pH of 6 was maintained by automatic addition of 2N KOH. Aerobic conditions were obtained by sparging the bioreactor with air at a rate of 1 vvm to ensure that the dissolved oxygen tension (DOT) was greater than 60%. The air was sterile filtered before being introduced into the bioreactors. The off gas was led through a condenser cooled to lower than 6° C. and analyzed for its volumetric content of $CO_2$ and $O_2$ by means of an acoustic gas analyser. The bioreactors were equipped with polarographic oxygen sensors that were calibrated with air (DOT, 100%) and $N_2$ (DOT, 0%). Cells were grown on sucrose in defined medium consisting of the following components: 3.0 g/l $NaNO_3$, 1.0 g/l $KH_2PO_4$, 0.5 g/l KCl, 0.5 g/l $MgSO_4.7H_2O$, 0.5/l g $FeSO_4.7H_2O$. The concentration of sucrose was 30 g/l. Antifoam was added to a final concentration of 50 ul/l.

The bioreactor was inoculated with spores of the *A. nidulans* strain containing C4H, 4CL1, and VST1, previously propagated on solid minimal medium, with the following composition: 1 g/L glucose, 0.85 g/L $NaNO_3$, 0.1 g/L KCl, 0.1 g/L $MgSO_4.7H_2O$; and 0.3 g/L $KH_2PO_4$, 0.00008 g/L $CuSO_4.5H_2O$, 0.000008 g/L $Na_2B_4O_7.10H_2O$, 0.00016 g/L $FeSO_4.7H_2O$, 0.00016 g/L $MnSO_4.2H_2O$, 0.00016 g/L $Na_2MoO_4.2H_2O$, and 0.0016 g/L $ZnSO_4.7H_2O$. The spores were cultivated at 37° C. for 5 days and harvested by adding Tween 80% solution (0.25% (w/v)).

(b) Extraction of Pinosylvin in *Aspergillus nidulans*

The cells were disrupted by homogenization (in a Polytron tissue homogenizer) and the intracellular pinosylvin was extracted with 10 ml ethyl acetate. The extraction was enforced by mixing in a rotary mixer (approximately 15 min) and the separation of phases, by centrifugation (4500 rpm, at 4° C., for 5 min). The acetate phase was subjected to freeze-drying (approximately 2 h) and the dry product was redissolved in 0.5 ml methanol and analysed by HPLC.

(c) Analysis of Pinosylvin

The analysis of pinosylvin in samples from the batch cultivation was performed using the method as described in example 9b.
Results The recombinant strain of *Aspergillus nidulans* containing C4H, 4CL1, and VST1, as described in Example 16e, was cultivated on 30 g/L of sucrose in a bioreactor in batch mode, according to Example HD4. After approximately 48 h of cultivation, the cells were harvested from the bioreactor, disrupted by homogenization and analysed for their intracellular content of pinosylvin according to (b) and (c) above.

The HPLC-analysis showed that the *A. nidulans* strain containing C4H, 4CL1, and VST1 exhibited intracellularly a component with a retention time identical to the standard of trans-pinosylvin (FIGS. 4 and 5). In addition, the UV absorption spectra were similar to the absorption spectrum of pure trans-pinosylvin (not shown) as well, with a $\lambda_{max}$ of approximately 306 nm.

The results, therefore, demonstrated the presence of an active phenyl-propanoid pathway that led to in vivo production of trans-pinosylvin, in *A. nidulans* grown in a bioreactor in batch mode.

REFERENCES

The following publications are all hereby incorporated by reference:

Patent no. ZA200408194
Patent no. EP0309862
Patent no. EP0464461
U.S. Pat. No. 5,391,724
U.S. Pat. No. 5,973,230
Patent application WO2006125000 Method for the production of resveratrol in a recombinant oleaginous microorganism Huamg Lixuan Lisa, Du Pont (US)
Patent application WO2006055322 High arachidonic acid producing strains of *Yarrowia lipolytica* Damude Howard, Du Pont (US)
Abe, I., Watanabe, T. and Noguchi, H. (2004). Enzymatic formation of long-chain polyketide pyrones by plant type III polyketide synthases. Phytochemistry. 6, 2447-2453.
Aggarwal B B, Bhardwaj A, Aggarwal R S, Seeram N P, Shishodia S, Takada Y. (2004). Role of resveratrol in prevention and therapy of cancer: preclinical and clinical studies. Anticancer Res. 24, 2783-840. Review.
Allina, S. M., Pri-Hadash, A., Theilmann, D. A., Ellis, B. E. and Douglas, C. J. (1998) 4-coumarate: Coenzyme A ligase in hybrid poplar. Properties of enzymes, cDNA cloning, and analysis of recombinant clones. Plant Physiol. 116, 743-754.
Becker J V, Armstrong G O, van der Merwe M J, Lambrechts M G, Vivier M A, Pretorius I S. (2003). Metabolic engineering of *Saccharomyces cerevisiae* for the synthesis of the wine-related antioxidant resveratrol. FEMS Yeast Res. 4, 79-85.
Chen D C, Beckerich J M, Gaillardin C. One-step transformation of the dimorphic yeast *Yarrowia lipolytica*. Appl Microbiol Biotechnol. 1997:48:232-5.
Cochrane, F. C., Davin, L. B. and Lewis N. G. (2004). The *Arabidopsis* phenylalanine ammonia lyase gene family: kinetic characterization of the four PAL isoforms. Phytochemistry 65, 1557-1564.
Cordero Otero R. Gaillardin C. Efficient selection of hygromycin-B-resistant *Yarrowia lipolytica* transformants. Appl Microbiol Biotechnol. 1996:46:143-8.
Costa M L, Bedgar D L, Moinuddin S G A, Kim K, Cardenas C L, Cochrane F C, Shockey J M, Helms G L, Amakura Y, Takahashi H et al. Characterization in vitro and in vivo of the putative multigene 4-coumarate:CoA ligase network in *Arabidopsis*: syringyl lignin and sinapate/sinapyl alcohol derivative formation Phytochemistry, 2005:66:2072-2091
Ehlting, J., Büttner, D., Wang, Q., Douglas, C. J., Somssich, I. E. and Kombrink, E. (1999). Three 4-coumarate:coenzyme A ligases in *Arabidopsis thaliana* represents two evolutionary divergent classes in angiosperms. The plant journal. 19, 9-20.
Fickers P, Le Dall M T, Gaillardin C, Thonart P, Nicaud J M. New disruption cassettes for rapid gene disruption and marker rescue in the yeast *Yarrowia lipolytica*. J Microbiol Methods. 2003:55:727-37.

Gehlert, R., Schoppner, A. and Kindl, H. Stilbene synthase from seedlings of *Pinus sylvestris*—purification and induction in response to fungal infection. Mol. Plant-Microbe Interaction 3 (1990) 444-449.

Gems, D., Johnstone, I. L. and Clutterbuck, A. J. (1991). An autonomously replicating plasmid transforms *Aspergillus nidulans* at high frequency. Gene 98, 61-67.

Hain, R., Reif, H. J., Krause, E., Langebartels, R., Kindl, H., Vornam, B., Wiese, W., Schmelzer, E., Schreier, P. H., Stocker, R. H. and Stenzel, K. (1993). Disease resistance results from foreign phytoalexin expression in a novel plant. Nature 361, 153-156.

Hwang E I, Kaneko M, Ohnishi Y, Horinouchi S. (2003). Production of plant-specific flavanones by *Escherichia coli* containing an artificial gene cluster. Appl. Environ. Microbiol. 69, 2699-706.

Hamberger, B. and Hahlbrock, K. (2004). The 4-coumarate:CoA ligase gene family in *Arabidopsis thaliana* comprises one rare, sinapate-activating and three commonly occurring isoenzymes. Proc. Natl. Acad. Sci. USA. 101, 2209-2214.

Hart, J. H. (1981) Role of phytostilbenes in decay and disease resistance. Annu. Rev. Phytopathology 19, 437-458.

Hart, J. H., Shrimpton, D. M. (1979). Role of stilbenes in resistance of wood to decay. Phytopathology 69, 1138-1143.

Hemingway R. W., McGraw, G. W. and Barras, S. J. (1977). Polyphenols in *Ceratocystis minor* infected *Pinus taeda*: Fungal Metabolites, phloem and xylem phenols. J. Agric. Food Chem., 25, 717-722.

Juvvadi, P. R., Seshime, Y., Kitamoto, K. (2005). Genomics reveals traces of fungal phenylpropanoid-flavonoid metabolic pathway in the filamentous fungus *Aspergillus oryzae*. J Microbiol. 43, 475-486.

Juretzek T, Le Dall M, Mauersberger S, Gaillardin C, Barth G, Nicaud J. Vectors for gene expression and amplification in the yeast *Yarrowia lipolytica*. Yeast. 2001:18:97-113.

Kaneko, M., Ohnishi, Y. and Horinouchi, S. Cinnamate:Coenzyme (2003). A ligase from the Filamentous Bacteria *Streptomyces coelicolor* A3 (2), J. Bact. 185, 20-27.

Kindl, H. (1985) Biosynthesis of stilbenes. In Higuchi T, ed, Biosynthesis and Biodegradation of Wood Components. Academic Press, London, pp 349-377.

Kodan, A., Kuroda, H. and Sakai, F. (2002). A stilbene synthase from Japanese red pine (*Pinus densiflora*): Implications for phytoalexin accumulation and down-regulation of flavonoid biosynthesis. Proc. Natl. Acad. Sci. 99, 3335-3339.

Le Dall M T, Nicaud J M, Gaillardin C. Multiple-copy integration in the yeast *Yarrowia lipolytica*. Curr Genet. 1994: 26:38-44.

Lieutier, F., Sauvard, D., Brignolas, F., Picron, V., Yart, A., Bastien, C. and Jay-Allemand, C. (1996) Changes in phenolic metabolites of Scots pine phloem induced by *Ophiostoma brunneo-ciliatum*, a bark beetle-associated fungus. Eur. J. For Pathol. 26, 145-158

Lindberg L E, Willfor S M, Holmbom B R. (2004) Antibacterial effects of knotwood extractives on paper mill bacteria. J Ind Microbiol Biotechnol. 31, 137-147.

Madzak C, Gaillardin C, Beckerich J M. Heterologous protein expression and secretion in the non-conventional yeast *Yarrowia lipolytica*: a review. J Biotechnol. 2004:109:63-81.

Martin, V. J. J., Pitera, D. J., Withers, S. T., Newman, J. D. and Keasling, J. D. (2003). Engineering a mevalonate pathway in *Escherichia coli* for production of terpenoids. Nature biotechnology 21, 796-802.

Melchior F, Kindl H (1991). Coordinate and elicitor dependent expression of stilbene synthase and phenylalanine ammonialyase genes in *Vitis cv. Optima*. Arch. Biochem. Biophys 288, 552-557.

Mellanen, P., Petanen, T., Lehtimaki, J., Makela, S., Bylund, G., Holmbom, B., Mannila, E., Oikari, A. and Santti, R. (1996). Wood-derived estrogens: studies in vitro with breast cancer cell lines and in vivo in trout. Toxicol. App. Pharm. 136, 381-388.

Merkulov S, van Assema F, Springer J, Fernandez Del Carmen A, Mooibroek H. Cloning and characterization of the *Yarrowia lipolytica* squalene synthase (SQS1) gene and functional complementation of the *Saccharomyces cerevisiae* erg9 mutation. Yeast. 2000:16:197-206.

Mizutani M and Ohta D et al, 1998 Two Isoforms of NADPH: Cytochrome P450 Reductase in *Arabidopsis thaliana*. Gene Structure, Heterologous Expression in Insect Cells, and Differential Regulation Plant Physiol. 116, 357-367

Morita, H., Noguchi, H., Schröder, J. and Abe, I. (2001). Novel polyketides synthesized with a higher plant stilbene synthase. Eur. J. Biochem. 268, 3759-3766.

Müller S, Sandal T, Kamp-Hansen P, Dalbøge H. Comparison of expression systems in the yeasts *Saccharomyces cerevisiae*, *Hansenula polymorpha*, *Klyveromyces lactis*, *Schizosaccharomyces pombe* and *Yarrowia lipolytica*. Cloning of two novel promoters from *Yarrowia lipolytica*. Yeast. 1998:14:1267-83.

Nicaud J M, Madzak C, van den Broek P, Gysler C, Duboc P, Niederberger P, Gaillardin C. Protein expression and secretion in the yeast *Yarrowia lipolytica*. FEMS Yeast Res. 2002:2:371-9.

Pignède G, Wang H J, Fudalej F, Seman M, Gaillardin C, Nicaud J M. Autocloning and amplification of LIP2 in *Yarrowia lipolytica*. Appl Environ Microbiol. 2000:66:3283-9.

Preisig-Muller, R., Schwekendiek, A., Brehm, I., Reif, H. J. and Kindl, H. (1999). Characterization of a pine multigene family containing elicitor-responsive stilbene synthase genes. Plant Mol. Biol. 1999 39, 221-229.

Pacher T, Seger C, Engelmeier D, Vajrodaya S, Hofer O, Greger H. (2002). Antifungal stilbenoids from *Stemona collinsae*. J Nat. Prod. 65, 820-827.

Raiber S, Schröder G, Schröder J. (1995). Molecular and enzymatic characterization of two stilbene synthases from Eastern white pine (*Pinus strobus*). A single Arg/His difference determines the activity and the pH dependence of the enzymes. FEBS Lett. 361, 299-302.

Richter, C., Wild, A. (1992). Phenolic compounds in needles of Norway spruce trees in relation to novel forest decline: I. Studies on trees from site of the Northern Black Forest. Biochem. Biophys. Pflanz 188, 305-320.

Ro D. K., Douglas C. J. (2004). Reconstitution of the entry point of plant phenylpropanoid metabolism in yeast (*Saccharomyces cerevisiae*): implications for control of metabolic flux into the phenylpropanoid pathway. J. Biol. Chem. 279, 2600-2607.

Rosemann, D., Heller, W. and Sandermann, H. (1991). Biochemical Plant Responses to Ozone. II. Induction of Stilbene Biosynthesis in Scots Pine (*Pinus sylvestris* L.) Seedlings. Jr. Plant Physiol. 97, 1280-1286.

Roupe, K. A., Fukuda, C., Halls, S., Yáñez, J. A. and Davies N. M. (2005) Pinosylvin: Method of Analysis, Anti-Cancer Activity and Metabolism. American Association of Pharmaceutical Scientists Annual Meeting. November. Accepted.

Roupe, K. A., Remsberg, C. M., Yáñez. J. A. and Davies, N. M. (2006). Pharmacometrics of Stilbenes: Seguing Towards the Clinic. Curr. Clin. Pharmac. 1, 81-101.

Samappito, S., Page, J. E., Schmidt, J., De-Eknamkul, W. and Kutchan, T. M. (2003). Aromatic and pyrone polyketides synthesized by a stilbene synthase from *Rheum tataricum*. Phytochemistry 62, 313-323.

Sambrook, J., Fritsch, E. F. and Maniatis, T. (1989). Molecular Cloning, A Laboratory Manual, 2d edition, Cold Spring Harbor, N.Y.

Schanz, S., Schröder, G. and Schröder, J. (1992). Stilbene synthase from Scot's pine (*Pinus sylvestris*) FEBS Lett. 313, 71-74.

Schöppner, A. and Kindl, H. (1984) Purification and properties of a stilbene synthase from induced cell suspension cultures of peanut. J. Biol. Chem. 259, 6806-6811.

Schröder G, Brown J W S, Schröder J. (1988). Molecular analysis of resveratrol synthase. cDNA clones and relationship with chalcone synthase. Eur J Biochem 172, 161-169.

Seshime, Y., Juvvadi, P. R., Fujii, I. and Kitamoto, K. (2005). Genomic evidences for the existence of a phenylpropanoid metabolic pathway in *Aspergillus oryzae*. Biochem. Biophys. Res Commun. 337, 747-51.

Skinnider, L. and Stoessl A. (1986). The effect of the phytoalexins, lubimin, (-)-maackiain, pinosylvin, and the related compounds dehydroloroglossol and hordatine M on human lymphoblastoid cell lines. Experientia 42, 568-570.

Stojanovic, S., Sprinz, H. and Brede, O. (2001). Efficiency and mechanism of the anti-oxidant action of trans-resveratrol and its analogues in the radical liposome oxidation. Arch. Biochem. Biophys. 391, 79-89.

Suga T., Ohta S., Munesada K., Ide N., Kurokawa M., Shimizu M., Ohta E. (1993). Endogenous pine wood nematicidal substances in pines, *Pinus massoniana*, *P. strobus* and *P. palustris*. Phytochemistry 33, 1395-1401.

Tropf, S., Karcher, B., Schröder, G. and Schröder, J. (1995). Reaction mechanisms of homodimeric plant polyketide synthase (stilbenes and chalcone synthase). A single active site for the condensing reaction is sufficient for synthesis of stilbenes, chalcones, and 6'-deoxychalcones. J. Biol. Chem. 270, 7922-7928.

Urban P, Werck-Reichhart D, Teutsch H G, Durst F, Regnier S, Kazmaier M, Pompon D (1994) Characterization of recombinant plant cinnamate 4-hydroxylase produced in yeast. Kinetic and spectral properties of the major plant P450 of the phenylpropanoid pathway. Eur J. Biochem. 222:843-50

Verduyn C, Postma E, Scheffers W A, Van Dijken J P. (1992). Effect of benzoic acid on metabolic fluxes in yeasts: a continuous-culture study on the regulation of respiration and alcoholic fermentation. Yeast. 8, 501-517.

Watts et al; Watts K T, Mijts B N, Lee P C, Manning A J, Schmidt-Dannert C. (2006). Discovery of a substrate selectivity switch in tyrosine ammonia-lyase, a member of the aromatic amino acid lyase family. Chem. Biol. 13:1317-26.

Wiese W, Vornam B, Krause E, Kindl H (1994). Structural organization and differential expression of three stilbene synthase genes located on a 13 kb grapevine DNA fragment. Plant Mol Biol 26, 667-677.

The following is a summary of the nucleotide and amino acid sequences appearing herein:

SEQ ID NO: 1 is a nucleotide sequence from *Arabidopsis thaliana* encoding a phenylalanine ammonia lyase (PAL2).

SEQ ID NO: 2 is the amino acid sequence encoded by SEQ ID NO: 1.

SEQ ID NO: 3 is a nucleotide sequence from *Arabidopsis thaliana* encoding a 4-coumarate:CoenzymeA ligase (4CL1).

SEQ ID NO: 4 is the amino acid sequence encoded by SEQ ID NO: 3.

SEQ ID NO: 5 is a nucleotide sequence from *Rheum tataricum* encoding a resveratrol synthase (RES).

SEQ ID NO: 6 is the amino acid sequence encoded by SEQ ID NO: 5.

SEQ ID NO: 7 is a nucleotide sequence from *Rheum tataricum* encoding a resveratrol synthase (RES), which is codon-optimized for expression in *S. cerevisiae*.

SEQ ID NO: 8 is the amino acid sequence encoded by SEQ ID NO: 7.

SEQ ID NO: 9 is a nucleotide sequence from *Vitis vinifera* encoding a resveratrol synthase (VST1), which is codon-optimized for expression in *S. cerevisiae*.

SEQ ID NO: 10 is the amino acid sequence encoded by SEQ ID NO: 9.

SEQ ID NOs 11-16 are primer sequences appearing in Table 1, Example 1.

SEQ ID Nos 17 to 22 are primer sequences used in Example 16a.

PS SEQ ID Nos 23 to 26 are primer sequences used in Example 16b.

SEQ ID Nos 27 to 30 are primer sequences used in Example 16c.

The invention claimed is:

1. A method for producing pinosylvin by expression in a micro-organism, said method comprising culturing said micro-organism under pinosylvin producing conditions, wherein said micro-organism has an operative metabolic pathway comprising at least one enzyme activity, said pathway producing pinosylvin from cinnamic acid.

2. The method of claim 1, comprising culturing a micro-organism cell having a pinosylvin producing metabolic pathway under pinosylvin producing conditions, wherein said pathway comprises a phenylalanine ammonia lyase (PAL) accepting phenylalanine as a substrate and producing cinammic acid therefrom, said PAL being such that if the PAL also accepts tyrosine as a substrate and forms coumaric acid therefrom, the ratio Km(phenylalanine)/Km(tyrosine) for said PAL is less than 1:1, and wherein if said micro-organism produces a cinammate-4-hydroxylase enzyme (C4H), the ratio Kcat(PAL)/Kcat(C4H) is at least 2:1.

3. The method of claim 2, wherein said pinosylvin is produced from cinnamoyl-CoA by a stilbene synthase expressed in said micro-organism from nucleic acid coding for said enzyme which is not native to the micro-organism and wherein said stilbene synthase is a pinosylvin synthase (EC 2.3.1.146) from a plant belonging to the genus of *Pinus*, e.g. *P. sylvestris*, P. strobes, P. densiflora, *P. taeda*, a plant belonging to the genus *Picea*, or any one of the genus *Eucalyptus* or is a resveratrol synthase (EC 2.3.1.95) from a plant belonging to the genus of *Arachis*, a plant belonging to the genus of *Rheum*, or a plant belonging to the genus of *Vitus* or any one of the genera *Pinus, Picea, Lilium, Eucalyptus, Parthenocissus, Cissus, Calochortus, Polygonum, Gnetum, Artocarpus, Nothofagus, Phoenix, Festuca, Carex, Veratrum, Bauhinia* or *Pterolobium*.

4. The method of claim 2, wherein said micro-organism produces an L-phenylalanine ammonia lyase (EC 4.3.1.5) by expression therein of a gene native to a plant belonging to the genus of *Arabidopsis*, a plant belonging to the genus of *Brassica*, a plant belonging to the genus of *Citrus*, a plant belonging to the genus of *Phaseolus*, a plant belonging to the genus of *Pinus*, a plant belonging to the genus of *Populus*, a plant belonging to the genus of *Solanum*, a plant belonging to the genus of *Prunus*, a plant belonging to the genus of *Vitus*, a plant belonging to the genus of *Zea*, or a plant belonging to any one of the genera *Agastache, Ananas, Asparagus, Bromheadia, Bambusa, Beta, Betula, Cucumis, Camellia, Capsicum, Cassia, Catharanthus, Cicer, Citrullus, Coffea, Cucurbita, Cynodon, Daucus, Dendrobium, Dianthus, Digitalis, Dioscorea, Eucalyptus, Gallus, Ginkgo, Glycine, Hordeum, Helianthus, Ipomoea, Lactuca, Lithospermum, Lotus, Lycopersicon, Medicago, Malus, Manihot, Medicago, Mesembryanthemum, Nicotiana, Olea, Oryza, Pisum, Persea, Petroselinum, Phalaenopsis, Phyllostachys, Physcomitrella, Picea, Pyrus, Quercus, Raphanus, Rehmannia, Rubus, Sorghum, Sphenostylis, Stellaria, Stylosanthes, Triticum, Trifolium, Triticum, Vaccinium, Vigna*, or *Zinnia*, or from a filamentous fungus belonging to the genus *Aspergillus*, whereby said cinnamic acid is formed from L-phenylalanine by the action of said L-phenylalanine lyase in said metabolic pathway.

5. The method of claim 2, wherein cinnamoyl-CoA is formed in said pathway in a reaction catalysed by an enzyme in which ATP and CoA are substrates and ADP is a product catalysed by a 4-coumarate-CoA ligase or a cinnamoyl-CoA ligase.

6. The method of claim 5, wherein said 4-coumarate-CoA ligase or cinnamate-CoA ligase is 4-coumarate-CoA ligase/cinnamate-CoA ligase (EC 6.2.1.12) from a plant belonging to the genus of *Abies*, a plant belonging to the genus of *Arabidopsis*, a plant belonging to the genus of *Brassica*, a plant belonging to the genus of *Citrus*, a plant belonging to the genus of *Larix*, a plant belonging to the genus of *Phaseolus*, a plant belonging to the genus of *Pinus*, a plant belonging to the genus of *Populus*, a plant belonging to the genus of *Solanum*, a plant belonging to the genus of *Vitus*, a plant belonging to the genus of *Zea*, or a plant belonging to any one of the genera *Agastache, Amorpha, Cathaya, Cedrus, Crocus, Festuca, Glycine, Juglans, Keteleeria, Lithospermum, Lolium, Lotus, Lycopersicon, Malus, Medicago, Mesembryanthemum, Nicotiana, Nothotsuga, Oryza, Pelargonium, Petroselinum, Physcomitrella, Picea, Prunus, Pseudolarix, Pseudotsuga, Rosa, Rubus, Ryza, Saccharum, Suaeda, Thellungiella, Triticum,* or *Tsuga,* from a filamentous fungus belonging to the genus *Aspergillus,* a filamentous fungus belonging to the genus *Neurospora,* a fungus belonging to the genus *Yarrowia,* a fungus belonging to the genus of *Mycosphaerella,* from a bacterium belonging to the genus of *Mycobacterium,* a bacterium belonging to the genus of *Neisseria,* a bacterium belonging to the genus of *Streptomyces,* a bacterium belonging to the genus of *Rhodobacter,* or from a nematode belonging to the genus *Ancylostoma,* a nematode belonging to the genus *Caenorhabditis,* a nematode belonging to the genus *Haemonchus,* a nematode belonging to the genus *Lumbricus,* a nematode belonging to the genus *Meilodogyne,* a nematode belonging to the genus *Strongyloidus,* or a nematode belonging to the genus *Pristionchus.*

7. The method of claim 2, wherein at least one copy of a genetic sequence encoding a 4-coumarate-CoA ligase or cinnamate-CoA ligase is operatively linked to an expression signal not natively associated with said genetic sequence in said organism.

8. The method of claim 2, wherein at least one copy of a genetic sequence encoding a resveratrol synthase is operatively linked to an expression signal not natively associated with said genetic sequence in said organism and/or at least one copy of a genetic sequence encoding a pinosylvin synthase is operatively linked to an expression signal not natively associated with said genetic sequence in said organism.

9. The method of claim 2, wherein the micro-organism is a yeast belonging to the genus *Saccharomyces, Klyuveromyces, Candida, Pichia, Debaromyces, Hansenula, Yarrowia, Zygosaccharomyces* or *Schizosaccharomyces.*

10. The method of claim 2, wherein the micro-organism is a filamentous fungi belonging to the genus *Aspergillus.*

11. The method of claim 2, wherein the micro-organism is a bacterium belonging to the genus *Escherichia* or *Lactococcus.*

12. The method of claim 1, further including isolating pinosylvin thereby produced.

13. The method of claim 2, wherein said culturing is conducted in the absence of an external source of cinnamic acid or esters thereof.

14. The method of claim 2, wherein said micro-organism cell lacks both exogenous and endogenous production of C4H.

15. The method of claim 2, wherein said culturing is conducted in the presence of a carbon substrate selected from the group of fermentable carbon substrates consisting of monosaccharides, oligosaccharides and polysaccharides.

16. The method of claim 2, wherein said culturing is conducted in the presence of a carbon substrate selected from the group of fermentable carbon substrates consisting of monosaccharides, oligosaccharides and polysaccharides.

17. The method of claim 16, wherein said fermentable carbon substrate is glucose, fructose, galactose, xylose, arabinose, mannose, sucrose, lactose, erythrose, threose or ribose.

18. The method of claim 1, further including incorporation of said produced pinosylvin as a nutraceutical into a food or feed product.

19. A micro-organism having an operative metabolic pathway producing cinnamoyl-CoA from cinnamic acid and producing pinosylvin from cinnamoyl-CoA by the action of a stilbene synthase which has a higher turnover rate with cinnamoyl-CoA as substrate than with 4-coumaroyl-CoA as substrate.

20. A micro-organism composition comprising micro-organism cells according to claim 19 and at least 1.5 mg/g pinosylvin on a dry weight basis, wherein said micro-organism is of the genus *Saccharomyces* and/or wherein said pinosylvin is at least partially contained within the cells of said micro-organism.

21. The method of claim 1 wherein under said pinosylvin producing conditions, the microorganism produces cinnamayl-CoA from said cinnamic acid, and pinosylvin from said cinnamoyl-CoA, said pinosylvin is produced from said cinnamoyl-CoA by a stilbene synthase expressed in said microorganism, and said stilbene synthase has a higher turnover rate with cinnamoyl-CoA as a substrate than with 4-coumaroyl-CoA as a substrate.

22. The method of claim 1 wherein said microorganism is of the genus *Saccharomyces.*

23. The method of claim 22 wherein said microorganism is of the species *Saccharomyces cerevisiae.*

24. The method of claim 3 in which said stilbene synthase is that of *Vitis vinifera.*

25. The method of claim 4 in which said L-phenylalanine lyase is that of *Arabidopsis thaliana.*

26. The method of claim 6 in which said 4-coumarate-CoA ligase and cinnamate-CoA ligase is that of *Arabidopsis thaliana.*

27. The method of claim 23 wherein the *Saccharomyces cerevisiae* expresses the stilbene synthase of *Vitus vinifera* and the L-phenylalanine lyase, 4-coumarate-CoA ligase and cinnamate-CoA ligase of *Arabidopsis thaliana.*

* * * * *